(12) United States Patent
Haffner et al.

(10) Patent No.: US 7,132,443 B2
(45) Date of Patent: Nov. 7, 2006

(54) FLUOROPYRROLIDINES AS DIPEPTIDYL PEPTIDASE INHIBITORS

(75) Inventors: Curt Dale Haffner, Durham, NC (US); Darryl Lynn McDougald, Durham, NC (US); Amarjit Sab Randhawa, Durham, NC (US); Steven Michael Reister, Durham, NC (US); James Martin Lenhard, Durham, NC (US)

(73) Assignee: SmithKlineBeecham Corporation, Philadelphia, PA (US)

( * ) Notice: Subject to any disclaimer, the term of this patent is extended or adjusted under 35 U.S.C. 154(b) by 347 days.

(21) Appl. No.: 10/481,293

(22) PCT Filed: Jun. 26, 2002

(86) PCT No.: PCT/US02/20471

§ 371 (c)(1),
(2), (4) Date: Dec. 19, 2003

(87) PCT Pub. No.: WO03/002531

PCT Pub. Date: Jan. 9, 2003

(65) Prior Publication Data

US 2004/0171848 A1 Sep. 2, 2004

Related U.S. Application Data

(60) Provisional application No. 60/376,015, filed on Apr. 26, 2002, provisional application No. 60/301,333, filed on Jun. 27, 2001.

(51) Int. Cl.
A61K 31/40 (2006.01)
C07D 207/00 (2006.01)

(52) U.S. Cl. .................. 514/423; 548/530; 548/540

(58) Field of Classification Search .............. 548/530, 548/540; 514/423
See application file for complete search history.

(56) References Cited

U.S. PATENT DOCUMENTS

| | | |
|---|---|---|
| 4,766,109 A | 8/1988 | Czarniecki |
| 5,198,548 A | 3/1993 | Beylin |
| 5,554,753 A | 9/1996 | O'Donnell |
| 5,623,087 A | 4/1997 | Sibi |
| 5,939,554 A | 8/1999 | Sibi |
| 5,939,560 A | 8/1999 | Jenkins |
| 6,011,155 A | 1/2000 | Villhauer |
| 6,090,786 A | 7/2000 | Augustyns et al. |
| 6,107,317 A | 8/2000 | Villhauer |
| 6,110,949 A | 8/2000 | Villhauer |
| 6,124,305 A | 9/2000 | Villhauer |
| 6,166,063 A | 12/2000 | Villhauer |
| 6,172,081 B1 | 1/2001 | Damon |
| 6,201,132 B1 | 3/2001 | Jenkins |
| 6,303,661 B1 | 10/2001 | Demuth |
| 6,432,969 B1 | 8/2002 | Villhauer |
| 6,500,804 B1 | 12/2002 | Demuth |
| 6,881,564 B1 | 4/2005 | Abbott |
| 2002/0006899 A1 | 1/2002 | Pospisilik |
| 2002/0019411 A1 | 2/2002 | Robl et al. |
| 2002/0049164 A1 | 4/2002 | Demuth |
| 2002/0110560 A1 | 8/2002 | Demuth |
| 2003/0153509 A1 | 8/2003 | Bachovchin |
| 2003/0176357 A1 | 9/2003 | Pospisilik |
| 2004/0058876 A1 | 3/2004 | Hoffman |
| 2004/0072892 A1 | 4/2004 | Fukushima et al. |
| 2004/0077901 A1 | 4/2004 | Ikemoto |
| 2004/0176307 A1 | 9/2004 | Bachovchin |
| 2004/0259843 A1 | 12/2004 | Madar |
| 2004/0259902 A1 | 12/2004 | Boehringer |
| 2004/0259903 A1 | 12/2004 | Boehringer |
| 2005/0014703 A1 | 1/2005 | Demuth |
| 2005/0043292 A1 | 2/2005 | Parker |
| 2005/0065144 A1 | 3/2005 | Feng |

FOREIGN PATENT DOCUMENTS

| | | |
|---|---|---|
| DE | 10309005 | 9/2004 |
| EP | 1 245 568 | 3/2002 |
| EP | 1258480 | 11/2002 |
| EP | 1 333 025 | 8/2003 |
| EP | 1338595 | 8/2003 |
| EP | 1422293 | 5/2004 |
| EP | 1506967 | 2/2005 |
| EP | 154148 | 6/2005 |
| EP | 1541143 | 6/2005 |
| JP | 2002-265439 | 9/2002 |
| JP | 2004-26820 | 1/2004 |
| JP | 2005-139107 | 6/2005 |
| WO | 93/08259 | 4/1993 |
| WO | 95/06029 | 3/1995 |
| WO | 95/29691 | 11/1995 |
| WO | 95/29190 | 12/1995 |
| WO | 97/40832 | 11/1997 |
| WO | 98/19998 | 5/1998 |

(Continued)

OTHER PUBLICATIONS

Demange, Luc et al., "Practical synthesis of Boc and Fmoc protected 4-fluoro and 4-difluoroprolines from trans-4-hydroxyproline," *Tetrahedron Letters*, 1998, Vo. 39, No. 10, pp. 1169-1172.

(Continued)

*Primary Examiner*—Kamal A. Saeed
*Assistant Examiner*—Robert Shiao
(74) *Attorney, Agent, or Firm*—Amy H. Fix

(57) ABSTRACT

The present invention relates to novel compounds, their use for inhibiting serine proteases, such as dipeptidyl peptidases, such as dipeptidyl peptidase IV (DPP-IV) and to methods for their production and their therapeutic utility.

18 Claims, No Drawings

FOREIGN PATENT DOCUMENTS

| | | |
|---|---|---|
| WO | 99/33081 | 7/1999 |
| WO | 99/38501 | 8/1999 |
| WO | 99/61431 | 12/1999 |
| WO | 99/67278 | 12/1999 |
| WO | 99/67279 | 12/1999 |
| WO | 00/34241 | 6/2000 |
| WO | 00/56296 | 9/2000 |
| WO | 00/69868 | 11/2000 |
| WO | 01/00206 | 1/2001 |
| WO | 01/14318 | 3/2001 |
| WO | 01/34594 | 5/2001 |
| WO | 01/40180 | 6/2001 |
| WO | 01/52825 | 7/2001 |
| WO | 01/55105 | 8/2001 |
| WO | 01/62266 | 8/2001 |
| WO | 01/68603 | 9/2001 |
| WO | 01/72290 | 10/2001 |
| WO | 01/81304 | 11/2001 |
| WO | 01/81337 | 11/2001 |
| WO | 01/96295 | 12/2001 |
| WO | 01/97808 | 12/2001 |
| WO | 02/000206 | 1/2002 |
| WO | 02/02560 | 1/2002 |
| WO | 02/30890 | 4/2002 |
| WO | 02/30891 | 4/2002 |
| WO | 02/34243 | 5/2002 |
| WO | 02/38541 | 5/2002 |
| WO | 02/51836 | 7/2002 |
| WO | 02/62764 | 8/2002 |
| WO | 02/076450 | 10/2002 |
| WO | 02/83109 | 10/2002 |
| WO | 02/83128 | 10/2002 |
| WO | 03/000180 | 1/2003 |
| WO | 03/00181 | 1/2003 |
| WO | 03/000250 | 1/2003 |
| WO | 03/02595 | 1/2003 |
| WO | 03/04496 | 1/2003 |
| WO | 03/04498 | 1/2003 |
| WO | 03/15775 | 2/2003 |
| WO | 03/24942 | 3/2003 |
| WO | 03/24965 | 3/2003 |
| WO | 03/35037 | 5/2003 |
| WO | 03/35067 | 5/2003 |
| WO | 03/37327 | 5/2003 |
| WO | 03/57144 | 7/2003 |
| WO | 03/57666 | 7/2003 |
| WO | 03/68748 | 8/2003 |
| WO | 03/68757 | 8/2003 |
| WO | 03/95425 | 11/2003 |
| WO | 03/101958 | 12/2003 |
| WO | 03/106456 | 12/2003 |
| WO | 04/07446 | 1/2004 |
| WO | 04/07468 | 1/2004 |
| WO | 04/09544 | 1/2004 |
| WO | 04/14860 | 2/2004 |
| WO | 04/17989 | 3/2004 |
| WO | 04/20407 | 3/2004 |
| WO | 04/32836 | 4/2004 |
| WO | 05/32590 | 4/2004 |
| WO | 04/37169 | 5/2004 |
| WO | 04/37181 | 5/2004 |
| WO | 04/43940 | 5/2004 |
| WO | 04/99134 | 5/2004 |
| WO | 04/50022 | 6/2004 |
| WO | 04/52362 | 6/2004 |
| WO | 04/52850 | 6/2004 |
| WO | 04/58266 | 7/2004 |
| WO | 04/64778 | 8/2004 |
| WO | 04/80958 | 9/2004 |
| WO | 04/83212 | 9/2004 |
| WO | 04/85661 | 10/2004 |
| WO | 04/87053 | 10/2004 |
| WO | 04/87650 | 10/2004 |
| WO | 04/89362 | 10/2004 |
| WO | 04/99185 | 11/2004 |
| WO | 04/101514 | 11/2004 |
| WO | 04/103276 | 12/2004 |
| WO | 04/103993 | 12/2004 |
| WO | 04/108730 | 12/2004 |
| WO | 04/110436 | 12/2004 |
| WO | 04/111041 | 12/2004 |
| WO | 04/111051 | 12/2004 |
| WO | 04/112701 | 12/2004 |
| WO | 05/03135 | 1/2005 |
| WO | 05/11581 | 2/2005 |
| WO | 05/12312 | 2/2005 |
| WO | 05/21536 | 3/2005 |
| WO | 05/21550 | 3/2005 |
| WO | 05/23762 | 3/2005 |
| WO | 05/25554 | 3/2005 |
| WO | 05/26148 | 3/2005 |
| WO | 05/33099 | 4/2005 |
| WO | 05/33106 | 4/2005 |
| WO | 05/34940 | 4/2005 |

OTHER PUBLICATIONS

Ashton, et al., "Diastereoselective synthesis and configuration-dependent activity of (3-substituted-cycloalkyl)glycine pyrrolidides and thiazolidides as dipeptidyl peptidase IV inhibitors," *Bioorg. & Med Chem Lett.*, 2004, V14, pp. 859-863.

Demange et al., Synthesis of optically pure N-Boc-protected (2R,3R)-and (2R,3S)-3-fluoroprolines, *Tetrahedron Letters*, 2001, V42, pp. 651-653.

Augustyns, K. et al., "The Unique Properties of Didpeptidyl-Peptidase IV (DPP IV/CD26) and the Therapeutic Potential of DPP IV Inhibitors," *Current Medicinal Chemistry*, 199, vol. 6, No. 4, pp. 311-327.

Augustyns, K. et al., "Pyrrolidides: Synthesis and Structure-activity relationship as inhibitors of dipeptidyl peptidase IV," *European Journal of Medicinal Chemistry*, 1997, vol. 32, No. 4, pp. 301-309.

Ashworth, D.M. et al., "4-Cyanothiazolidides as very potent, stable inhibitors of dipeptidyl peptidase IV," *Bioorganic & Medicinal Chemistry Letters*, Nov. 19, 1996, vol. 6, No. 22, pp. 2745-2748.

FLUOROPYRROLIDINES AS DIPEPTIDYL PEPTIDASE INHIBITORS

This application is filed pursuant to 35 U.S.C. § 371 as a United States National Phase Application of International Application No. PCT/US02/20471 filed Jun. 26, 2002, which claims priority from U.S. 60/301,333 filed Jun. 27, 2001 and 60/376,015 filed Apr. 26, 2002.

FIELD OF INVENTION

The present invention relates to compounds inhibiting dipeptidyl peptidases, such as II (DPP-II) and IV (DPP-IV), to methods for their production, and to their therapeutic utility.

BACKGROUND OF THE INVENTION

Dipeptidyl peptidase IV (DPP-IV) is a post-proline/alanine cleaving serine protease found in various tissues of the body including kidney, liver, and intestine. DPP-IV is thought to regulate the activity of multiple physiogically important peptides, including, but not limited to, GLP1, GIP, GLP2, GRP, vasoactive intestinal peptide, peptide histidine methionine, PYY, substance P, beta-casomorphine, NPY, PACAP38, prolactin, chorionic gonadotropin, aprotinin, corticotropin-like intermediate lobe peptide, pituitary adenylyl cyclase-activating peptide, (Tyr)melanostatin, LD78beta (3–70), RANTES, eotaxin procolipase, enterostatin, vasostatin 1, endomorphin, morphiceptin, stromal cell derived factor, macrophage-derived chemokine, granulocyte chemotactic protein-2, and GHRH/GRF. As examples of the therapeutic value of DPP-IV, DPP-IV is believed to be involved in a variety of metabolic, gastrointestinal, viral, and inflammatory diseases, including, but not limited to, diabetes, obesity, hyperlipidemia, dermatological or mucous membrane disorders, psoriasis, intestinal distress, constipation, autoimmune disorders such as encephalomyelitis, complement mediated disorders such as glomerulonepritis, lipodystrophy, and tissue tissue damage, psychosomatic, depressive, and neuropsychiatric disease such as anxiety, depression, insomnia, schizophrenia, epilepsy, spasm, and chronic pain, HIV infection, allergies, inflammation, arthritis, transplant rejection, high blood pressure, congestive heart failure, tumors, and stress-induced abortions, for example cytokine-mediated murine abortions. For example, DPP-IV, also known as CD26, mediates T-cell activation and HIV infection (Ohtsuki et al., 2000). T-cells expressing DPP-IV/CD26 are preferentially infected and depleted in HIV-infected individuals (Ohtsuki et al., 2000). DPP-IV inhibitors have demonstrated anti-inflammatory effects in animal models of arthritis Tanaka et al, 1997). Additionally, DPP-IV inhibition has been shown to prolong cardiac transplant survival (Korom et al., 1997). In vitro studies suggest that DPP-IV/CD26 expression correlate with tumor progression of malignant melanomas of the skin (Van den Oord, 1998). Furthermore, DPP-IV is thought to regulate metabolism by cleaving the penultimate proline/alanine at the amino-terminus of polypeptides (Mentlein, 1999), such as glucagon-like peptides (GLP) and neuropeptide Y (NPY).

More specifically, GLPs help metabolize glucose and, thus, regulation of GLPs likely should be beneficial in the treatment of metabolic disorders such as diabetes. Diabetes, for example type 2 (also called noninsulin-dependent diabetes mellitus (NIDDM) or maturity-onset) diabetes, results in elevated blood sugar levels due to absolute or relative insufficiencies of insulin. Type 2 diabetes is the more common form of diabetes, accounting for 90% of cases, or about 16 million Americans. Most type 2 diabetics produce variable, sometimes normal, amounts of insulin, but they have abnormalities in liver and muscle cells that resist its actions. Insulin attaches to the receptors of cells, but glucose does not get inside, a condition known as insulin resistance. Many type 2 diabetics seem to be incapable of secreting enough insulin to overcome insulin resistance. GLP-1 enhances insulin secretion. Thus, regulation of GLP-1 correlates to a regulation of insulin secretion. Moreover, GLP-1 decreases hepatic glucose production, gastric emptying, and food intake (Deacon et al., 1995). Further, GLP-2 maintains the integrity of the intestinal mucosal epithelium via effects on gastric motility, nutrient absorption, crypt cell proliferation and apoptosis, and intestinal permeability (Drucker, 2001).

DPP-IV inhibitors preserve GLP-1 function for a longer time (Balka, 1999). Thus, DPP-IV inhibitors may promote satiety, weight loss, and the antidiabetic effects of GLP-1 (Deacon et al., 1995; Hoist and Deacon, 1998). For example, inhibition of DPP-IV with the known compound NVP-DPP728 increases plasma GLP-1 (2–36 amide) concentrations and improves oral glucose tolerance in obese Zucker rats. See, Diabetologia 42: 1324–1331. Both subcutaneously and intravenously administered GLP-1 is rapidly degraded from the $NH_2$-terminus in type II diabetic patients and in healthy subjects. See, Diabetes 44:1126, 1995.

Moreover, DPP-IV inhibitors preserve GLP-2 for longer periods of time and, thus, may be useful for treating intestinal insufficiencies and mucous membrane disorders (Hartmann B et al., 2000).

While DPP-IV is the predominate protease regulating GLP turnover, similar substrate or inhibitor specificity may be observed for related proteases. Related serine proteases include, but are not limited to, dipeptidyl peptidase-II (DPP-II), dipeptidyl peptidase IV beta, dipeptidyl peptidase 8, dipeptidyl peptidase 9, aminopeptidase P, fibroblast activating protein alpha (seprase), prolyl tripeptidyl peptidase, prolyl oligopeptidase (endoproteinase Pro-C), attractin (soluble dipeptidyl-aminopeptidase), acylaminoacyl-peptidase (N-acylpeptide hydrolase; fMet aminopeptidase) and lysosomal Pro-X carboxypeptidase (angiotensinase C, prolyl carboxypeptidase). Proline-cleaving metallopeptidases that may share similar substrate or inhibitor specificity to DPP-IV include membrane Pro-X carboxypeptidase (carboxypeptidase P), angiotensin-converting enzyme (Peptidyl-dipeptidase A multipeptidase), collagenase 1 (interstitial collagenase; matrix metalloproteinase 1; MMP-1; Mcol-A), ADAM 10 (alpha-secretase, myelin-associated disintegrin metalloproteinase), neprilysin (atriopeptidase; CALLA; CD10; endopeptidase 24.11; enkephalinase), Macrophage elastase (metalloelastase; matrix metalloproteinase 12; MMP-12), Matrilysin (matrix metalloproteinase 7; MMP-7), and neurolysin (endopeptidase 24.16; microsomal endopeptidase; mitochondrial oligopeptidase). See http://merops.iapc.bbsrc.ac.uk/.

Furthermore, beyond mammalian serine peptidases and proline-cleaving metallopeptidases, other non-mammalian proteases may share similar substrate or inhibitor specificity to DPP-IV. Non-limiting examples of such non-mammalian serine proteases include prolyl aminopeptidase (prolyl iminopeptidase), IgA1-specific serine type prolyl endopeptidase (IgA protease, *Neisseria, Haemophilus*), dipeptidyl aminopeptidase A (STE13) (*Saccharomyces cerevisiae*), dipeptidyl aminopeptidase B (fungus), prolyl oligopeptidase homologue (*Pyrococcus* sp.), oligopeptidase B (*Escherichia coli* alkaline proteinase II; protease II), dipeptidyl aminopeptidase Bi (*Pseudomonas* sp.), dipeptidyl-peptidase IV (bacteria), dipeptidyl aminopeptidase (*Aureobacterium*), dipeptidyl-peptidase IV (insect), dipeptidyl-peptidase V, allergen Tri t 4 (*Trichophyton tonsurans*), secreted alanyl DPP (*Aspergillus oryzae*), peptidase II-mes (*Prosopis velutina*), and bamboo serine proteinase (*Pleioblastus hindsii*). Non-limiting examples of such non-mammalian proline-cleaving metallopeptidases include penicillolysin (fungal acid metalloendopeptidase), proline-specific peptidyl-dipeptidase (*Streptomyces*), coccolysin (gelatinase, *Enterococcus faecalis*), aminopeptidase Ey, (hen egg yolk) (apdE g.p.; *Gallus gallus domesticus*), gametolysin (Chlamydomonas cell wall degrading protease), and snake venom proline-cleaving metalloproteases as well. See http://merops.iapc.bbsrc.ac.uk/ for further reference.

Dipeptidyl peptidase II (DPP II) is a serine protease localized to lysosomes in cells and believed to be involved in lysosomal degradation and protein turnover. The order of expression of DPP-II is kidney>>testis>or=heart>brain>or=lung>spleen>skeletal muscle>or=liver (Araki H et al., J Biochem (Tokyo) 2001, 129:279–88). This expression suggests possible utility in kidney or lysosomal-related disorders. Substrate specificity studies indicated that purified DPP-II hydrolyzes specifically alanine or proline residues at acidic pH (4.5–5.5). DPP-II has significant sequence homology and substrate specificity to quiescent cell proline dipeptidase and prolyl carboxypeptidase, suggesting possible overlapping functions between these proteases (Araki H et al., J Biochem (Tokyo) 2001, 129:279–88).

The present invention includes novel DPP-II and/or DPP-IV inhibitors, as well as methods of their therapeutic use and methods of their production. While not being limited thereby, the compounds of the present invention are believed useful for the treatment of a variety of metabolic, gastrointestinal, viral, and inflammatory diseases, including, but not limited to, diabetes, obesity, hyperlipidemia, dermatological or mucous membrane disorders, psoriasis, intestinal distress, constipation, autoimmune disorders such as encephalomyelitis, complement mediated disorders such as glomerulonepritis, lipodystrophy, and tissue damage, psychosomatic, depressive, and neuropsychiatric disease such as anxiety, depression, insomnia, schizophrenia, epilepsy, spasm, and chronic pain, HIV infection, allergies, inflammation, arthritis, transplant rejection, high blood pressure, congestive heart failure, tumors, and stress-induced abortions, for example cytokine-mediated murine abortions.

As compared to other di peptidyl peptidase inhibitors, the compounds of the present invention provide improved stability, potency, duration of action, and/or safety/toxicity profiles.

SUMMARY OF THE INVENTION

The present invention includes compounds of formula (I):

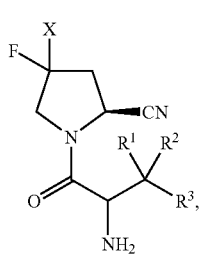

(I)

including salts, solvates, and pharmaceutically functional derivatives thereof, wherein X is F or H; $R^1$ and $R^2$ each are either H; alkyl; optionally substituted aryl or heteroaryl; or combine to form a 3 to 14 membered ring sytem, optionally containing one or more heteroatoms, and optionally containing one or more degrees of unsaturation. When $R^1$ and $R^2$ are optionally substituted aryl or heteroaryl, then $R^3$ is H or alkyl. Otherwise, $R^3$ is

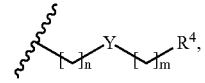

where n is 0–5; m is 0–12; Y is $S(O)_p$, O, alkylene, alkenylene, alkynylene, or a bond; p is 0–2; $R^4$ is $R^5$ when Y is S, O, alkylene, alkenylene, alkynylene, or a bond, where $R^5$ is optionally substituted alkyl, alkenyl, alkynyl, aryl, cycloalkyl, heteroaryl, or heterocyclyl; and $R^4$ is $R^5$ when Y is S(O) or $S(O)_2$, where $R^5$ is optionally substituted alkyl, aryl, cycloalkyl, heteroaryl, amino, alkylamino, arylamino, heteroarylamino, cycloalkylamino, or hydroxy.

Although not limiting, preferred optional substitutents include one or more of alkyl, alkoxy, aryloxy, halogen, haloalkyl, cyano, alkylsulfonyl, or aryl. More preferably, optional substituents includes one or more of $C_1$–$C_6$ alkyl, $C_1$–$C_6$ alkoxy, phenoxy, benzoxy, fluorine, chlorine, $C_1$–$C_6$ haloalkyl, cyano, $C_1$–$C_6$ alkylsulfonyl, phenyl, or benzyl.

In one embodiment, $R^1$ and $R^2$ are each aryl, and $R^3$ is H. Preferably, each aryl is phenyl. More preferably each phenyl is substituted with halogen. More preferably each halogen is fluorine, more preferabyl 4-fluorine.

In another embodiment, $R^1$ and $R^2$ are each alkyl and $R^3$ is

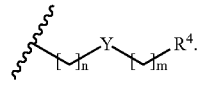

Preferably each of alkyl is $C_1$–$C_6$ alkyl. More preferably each alkyl is methyl. Preferably n is 0, m is 1, and Y is $S(O)_p$. In one preferred embodiment, p is 0, $R^4$ is $R^5$, and $R^5$ is optionally substituted aryl. Preferably $R^5$ is phenyl substituted with alkoxy. More preferably the alkoxy is methoxy. In another preferred embodiment, p is 1 or 2, $R^4$ is $R^6$, and $R^6$ is optionally substitued aryl. Preferably $R^6$ is phenyl substituted with alkoxy. More preferably the alkoxy is methoxy. More preferably p is 2.

In one embodiment, preferably the depicted $NH_2$ group is cis to the depicted nitrile warhead. In another embodiment preferably the depicted $NH_2$ group is trans to the depicted nitrile warhead.

Preferably X is H. Preferably the depicted F is cis to the depicted nitrile.

Particularly preferred compounds of the present invention include compounds of formula (I):

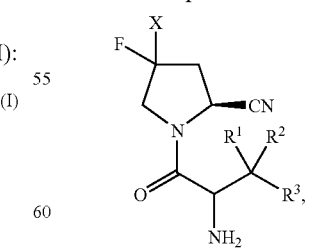

(I)

including salts, solvates, and pharmaceutically functional derivatives thereof, wherein X is F or H; $R^1$ and $R^2$ each are optionally substituted aryl or heteroaryl; and $R^3$ is H or alkyl.

Particularly preferred compounds of the present invention include compounds of formula (I):

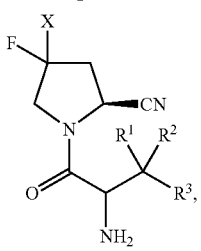

including salts, solvates, and pharmaceutically functional derivatives thereof, wherein X is F or H; $R^1$ and $R^2$ each are either (i) alkyl; or (ii) combine to form a 3 to 14 membered ring sytem, optionally containing one or more heteroatoms, and optionally containing one or more degrees of unsaturation;

$R^3$ is

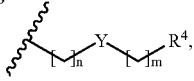

where n is 0–5; m is 0–12; Y is $S(O)_p$, O, alkylene, alkenylene, or alkynylene; p is 0–2; $R^4$ is $R^5$ when Y is S, O, alkylene, alkenylene, or alkynylene, where $R^5$ is optionally substituted alkyl, alkenyl, alkynyl, aryl, cycloalkyl, heteroaryl, or heterocyclyl; and $R^4$ is $R^6$ when Y is S(O) or $S(O)_2$, where $R^6$ is optionally substituted alkyl, aryl, cycloalkyl, heteroaryl, amino, alkylamino, arylamino, heteroarylamino, cycloalkylamino, or hydroxy.

Preferably p is 1 or 2. More preferably p is 2. Preferably $R^1$ and $R^2$ each are alkyl. More preferably $R^1$ and $R^2$ are each $C_1$–$C_6$ alkyl. More preferably $R^1$ and $R^2$ are each methyl.

Particularly preferred compounds of the present invention include:

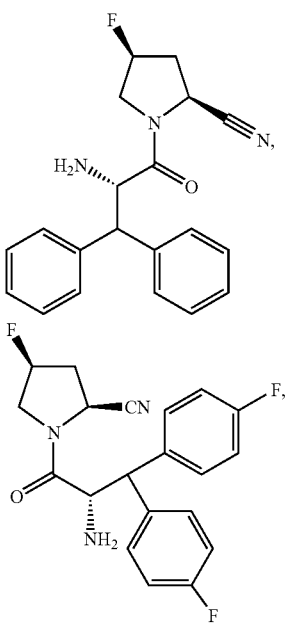

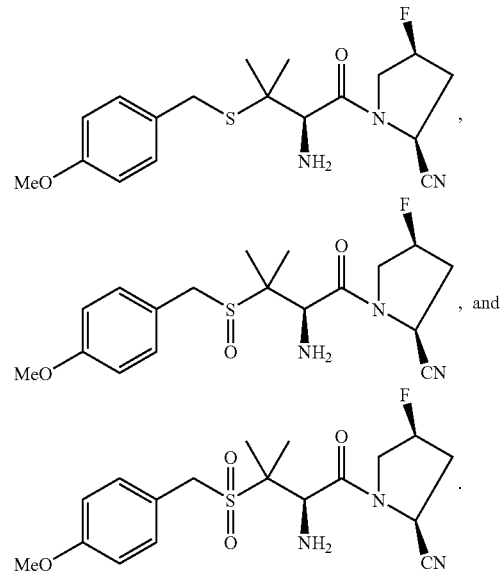

Particularly preferred compounds are selected from:

(2S,4S)-1-[(2S)-2-Amino-3,3-diphenylpropanoyl]-4-fluoropyrrolidine-2-carbonitrile hydrochloride;

(2S,4S)-1-[(2S)-2-Amino-3,3-bis(4-fluorophenyl)propanoyl]-4-fluoropyrrolidine-2-carbonitrile hydrochloride;

(2S,4S)-1-[(2S)-2-Amino-5-(4-fluorophenyl)-3,3-dimethylpentanoyl]-4-fluoro-2-pyrrolidinecarbonitrile hydrochloride;

(2S,4R)-1-[(2S)-2-Amino-4-(4-fluorophenyl)-3,3-dimethylbutanoyl]-4-fluoropyrrrolidine-2-carbonitrile hydrochloride;

(2S,4S)-1-{(2R)-2-Amino-3-[(4-methoxybenzyl)thio]-3-methylbutanoyl}-4-fluoropyrrolidine-2-carbonitrile hydrochloride;

(2S,4S)-1-{(2R)-2-Amino-3-methyl-3-[(3-phenylpropyl)thio]butanoyl}-4-fluoropyrrolidine-2-carbonitrile hydrochloride;

(2S,4S)-1-{(2R)-2-Amino-3-methyl-3-[(2-phenylethyl)thio]butanoyl}-4-fluoropyrrolidine-2-carbonitrile hydrochloride;

(2S,4S)-1-((2R)-2-Amino-3-{[3-(4-fluorophenyl)propyl]thio}-3-methylbutanoyl)-4-fluoropyrrolidine-2-carbonitrile hydrochloride;

(2S,4S)-1-{(2R)-2-Amino-3-[(4-methoxybenzyl)sulfonyl]-3-methylbutanoyl}-4-fluoropyrrolidine-2-carbonitrile hydrochloride;

(2S,4S)-1-{(2R)-2-Amino-3-[(4-methoxybenzyl)sulfinyl]-3-methylbutanoyl}-4-fluoropyrrolidine-2-carbonitrile hydrochloride;

(2S,4S)-1-((2R)-2-Amino-3-methyl-3-{[4-(trifluoromethyl)benzyl]thio}butanoyl)-4-fluoropyrrolidine-2-carbonitrile hydrochloride;

(2S,4S)-1-[(2S)-2-Amino-2-(1-vinylcyclopentyl)ethanoyl]-4-fluoropyrrolidine-2-carbonitrile hydrochloride;

(2S,4S)-1-[(2S)-2-Amino-(4-methoxyphenyl)-3,3-dimethylpentanoyl]-4-fluoropyrrolidine-2-carbonitrile hydrochloride;

(2S,4S)-1-{(2R)-2-Amino-3-methyl-3-[(3-phenylpropyl)sulfonyl]butanoyl}-4-fluoropyrrolidine-2-carbonitrile;

(2S,4S)-1-{(2R)-2-Amino-3-methyl-3-[(4-methylbenzyl)sulfonyl]butanoyl}-4-fluoropyrrolidine-2-carbonitrile;

(2S,4S)-1-((2R)-2-amino-3-{[4-(benzyloxy)benzyl]sulfonyl}-3-methylbutanoyl)-4-fluoropyrrolidine-2-carbonitrile;

(2S,4S)-1-{(2R)-2-amino-3-[(4-cyanobenzyl)sulfonyl]-3-methylbutanoyl}-4-fluoropyrrolidine-2-carbonitrile;

(2S,4S)-1-((2R)-2-amino-3-methyl-3-{[4-(methylsulfonyl)benzyl]sulfonyl}butanoyl)-4-fluoropyrrolidine-2-carbonitrile;

(2S,4S)-1-{(2S)-2-Amino-2-[1-(4-fluorobenzyl)cyclopentyl]ethanoyl}-4-fluoropyrrolidine-2-carbonitrile hydrochloride;

(2S,4S)-1-((2S)-2-Amino-2-{1-[4-(trifluoromethyl)phenyl]cyclopentyl}ethanoyl)-4-fluoropyrrolidine-2-carbonitrile hydrochloride;

(2S,4S)-1-{(2S)-2-Amino-2-[1-(4-fluorobenzyl)cyclopropyl]ethanoyl}-4-fluoropyrrolidine-2-carbonitrile hydrochloride;

(2S,4S)-1-[(2R)-2-Amino-3-(benzylsulfonyl)-3-methylbutanoyl]-4-fluoropyrrolidine-2-carbonitrile hydrochloride;

(2S,4S)-1-{(2R)-2-amino-3-[(3-methoxybenzyl)sulfonyl]-3-methylbutanoyl}-4-fluoropyrrolidine-2-carbonitrile hydrochloride;

(2S,4S)-1-{(2R)-2-Amino-3-[(1,1'-biphenyl-4-yl methyl)sulfonyl]-3-methylbutanoyl}-4-fluoropyrrolidine-2-carbonitrile hydrochloride;

(2S,4S)-1-{(2R)-2-Amino-3-[(2-methoxybenzyl)sulfonyl]-3-methylbutanoyl}-4-fluoropyrrolidine-2-carbonitrile hydrochloride;

(2S,4S)-1-{(2R)-2-Amino-3-methyl-3-[(pyridin-3-ylmethyl)thio]butanoyl}-4-fluoropyrrolidine-2-carbonitrile;

(2S,4S)-1-{(2R)-2-Amino-3-methyl-3-[(pyridin-2-ylmethyl)thio]butanoyl}-4-fluoropyrrolidine-2-carbonitrile hydrochloride;

(2S,4S)-1-{(2R)-2-amino-3-methyl-3-[(pyridin-4-ylmethyl)thio]butanoyl}-4-fluoropyrrolidine-2-carbonitrile hydrochloride;

(2S,4S)-1-{(2R)-2-amino-3-[(4-fluorobenzyl)sulfonyl]-3-methylbutanoyl}-4-fluoropyrrolidine-2-carbonitrile hydrochloride;

(2S,4S)-1-{(2R)-2-amino-3-methyl-3-[(3-phenoxybenzyl)sulfonyl]butanoyl}-fluoropyrrolidine-2-carbonitrile hydrochloride;

(2S,4S)-1-{(2R)-2-amino-3-methyl-3-[(3-phenoxybenzyl)thio]butanoyl}-4-fluoropyrrolidine-2-carbonitrile hydrochloride;

(2S,4S)-1-((2R)-2-Amino-3-{[(5-chloro-1,1-dioxido-1-benzothien-3-yl)methyl]sulfonyl}-3-methylbutanoyl)-4-fluoropyrrolidine-2-carbonitrile hydrochloride;

(2S,4S)-1-{(2R)-2-Amino-3-[(2,1,3-benzoxadiazol-5-yl methyl)thio]-3-methylbutanoyl}-4-fluoropyrrolidine-2-carbonitrile hydrochloride;

(2S,4S)-1-{(2R)-2-Amino-3-methyl-3-[(pyridin-4-yl methyl)sulfonyl]butanoyl}-4-fluoropyrrolidine-2-carbonitrile hydrochloride;

(2S,4S)-1-[(2S)-2-Amino-3-pyridin-4-yl propanoyl]-4-fluoropyrrolidine-2-carbonitrile hydrochloride;

(2S,4S)-1-[(2S)-2-Amino-3-pyridin-3-ylpropanoyl]-4-fluoropyrrolidine-2-carbonitrile hydrochloride;

(2S,4S)-1-[(2S)-2-Amino-3-piperidin-4-ylpropanoyl]-4-fluoropyrrolidine-2-carbonitrile dihydrochloride;

(2S,4S)-1-[(2S)-2-Amino-3-piperidin-3-ylpropanoyl]-fluoropyrrolidine-2-carbonitrile dihydrochloride;

(2S,4S)-1-[(2S)-2-Amino-3-piperidin-2-ylpropanoyl]-4-fluoropyrrolidine-2-carbonitrile dihydrochloride;

(2S,4S-1-{(2S)-2-Amino-3-[1-(isopropylsulfonyl)piperidin-4-yl]propanoyl}-4-fluoropyrrolidine-2-carbonitrilehydrochloride;

(2S,4S)-1-{(2S)-2-Amino-3-[1-(4-methylphenylsulfonyl)piperidin-4-yl]propanoyl}-4-fluoropyrrolidine-2-carbonitrile hydrochloride;

(2S,4S)-1-{(2S)-2-Amino-3-[1-(isopropylsulfonyl)piperidin-3-yl]propanoyl}-4-fluoropyrrolidine-2-carbonitrile hydrochloride;

(2S,4S)-1-{(2S)-2-Amino-3-[1-(4-methylphenylsulfonyl)piperidin-3-yl]propanoyl}-4-fluoropyrrolidine-2-carbonitrile hydrochloride;

(2S,4S)-1-[(2S)-2-Amino-3-(1-benzothien-3-yl)propanoyl]-4-fluoropyrrolidine-2-carbonitrile hydrochloride;

(2S,4S)-1-{(2S)-2-Amino-3-methyl-3-[4-(trifluoromethyl)phenyl]butanoyl}-4-fluoropyrrolidine-2-carbonitrile hydrochloride; and (3R)-3-Amino-4-[(2S,4S)-2-cyano-4-fluoropyrrolidin-1-yl]-2-methyl-4-oxobutane-2-sulfonic acid.

Another aspect of the present invention includes pharmaceutical formulations that include a compound of the present invention. Preferably the pharmaceutical formulation further includes a pharmaceutically acceptable carrier.

Another aspect of the present invention includes a method of inhibiting a post proline/analine cleaving protease through administration of a compound of the present invention. Preferably the post proline/analine cleaving protease is a serine protease. More preferably the serine protease is a dipeptidyl peptidase. More preferably the dipeptidyl peptidase is DPP-II or DPP-IV.

Another aspect of the present invention includes a method for the treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonepritis, lipodystrophy, tissue damage, psychosomatic, depressive, and neuropsychiatric disorders, HIV infection, allergies, inflammation, arthritis, transplant rejection, high blood pressure, congestive heart failure, tumors, and stress-induced abortions through the administration of a compound of the present invention. Preferably the administration is for the treatment or prophylaxis of diabetes.

Another aspect of the present invention includes the use of a compound of the present invention in the manufacture of a medicament for the inhibition of a post proline/analine cleaving protease. Preferably the post proline/analine cleaving protease is a serine protease. More preferably the serine protease is a dipeptidyl peptidase. More preferably the dipeptidyl peptidase is DPP-II or DPP-IV.

Another aspect of the present invention includes the use of a compound of the present invention in the manufacture of a medicament for the treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonepritis, lipodystrophy, tissue damage, psychosomatic, depressive, and neuropsychiatric disorders, HIV infection, allergies, inflammation, arthritis, transplant rejection, high blood pressure, congestive heart failure, tumors, and stress-induced abortions.

Another aspect of the present invention includes a compound of the present invention for use as an active therapeutic substance. In addtion a compound of the present invention may be used in the manufacture of a medicament for the inhibition of serine protease. Preferably such use is for the manufacture of a medicament for the treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonepritis, lipodystrophy, tissue damage, psychosomatic, depressive, and neuropsychiatric disorders, HIV infection, allergies, inflammation, arthritis, transplant rejection, high blood pressure, congestive heart failure, tumors, and stress-induced abortions.

DETAILED DESCRIPTION OF THE PREFERRED EMBODIMENT

The term "alkyl" refers to a straight or branched chain saturated aliphatic hydrocarbon that may be optionally substituted, with multiple degrees of substitution being allowed. Examples of "alkyl" include, but are not limited to methyl, ethyl, n-propyl, isopropyl, n-butyl, t-butyl, n-pentyl, isobutyl, and the like.

As used throughout this specification, the preferred number of carbon atoms will be represented by, for example, the phrase "$C_x$–$C_y$ alkyl" which refers to an alkyl group, as herein defined, containing the specified number of carbon atoms. Similar terminology will apply for other preferred ranges as well.

The term "alkylene" refers to a divalent straight or branched chain aliphatic hydrocarbon radical that may be optionally substituted, with multiple degrees of substitution being allowed. An example of "alkylene" includes, without limitation, methylene, namely —$CH_2$—.

The term "alkenyl" refers to a straight or branched chain aliphatic hydrocarbon, containing one or more carbon-to-carbon double bonds that may be optionally substituted, with multiple degrees of substitution being allowed. Examples include, but are not limited to, vinyl and the like.

As used herein the term "alkenylene" refers to a divalent straight or branched chain aliphatic hydrocarbon radical, containing one or more carbon-to-carbon double bonds, which may be optionally substituted, with multiple degrees of substitution being allowed. An example of "alkenylene" includes, without limitation, vinylene, namely, —CH=CH—.

As used herein the term "alkynyl" refers to a straight or branched aliphatic hydrocarbon containing one or more triple bond, which may optionally be substituted, with multuiple degrees of substitution being allowed. Examples of "alkynyl" as used herein include, but are not limited to, ethynyl and the like.

As used herein the term "alkynylene" refers to a divalent straight or branched chain aliphatic hydrocarbon radical, containing at least one carbon-to-carbon triple bond, that may be further substituted, with multiple degrees of substitution being allowed. An example of "alkynylene" includes, without limitation, ethynylene, namely —C≡C—.

The term "aryl" refers to an aromatic ring system, such as an optionally substituted benzene ring system, such as phenyl. The term encompasses fused systems where one or more optionally substituted benzene rings form, for example, anthracene, phenanthrene, or naphthalene ring systems. The term includes ring(s) optionally substituted, with multiple degrees of substitution being allowed, and also includes an optional alkylene linker, such as $C_1$–$C_6$ alkylene, through which the aryl group may be attached. Examples of "aryl" groups include, but are not limited to phenyl, benzyl, 2-naphthyl, 1-naphthyl, biphenyl, as well as substituted derivatives thereof.

The term "heteroaryl" refers to a monocyclic aromatic ring system, or to a fused bicyclic aromatic ring system comprising two or more aromatic rings. These heteroaryl rings contain one or more nitrogen, sulfur, and/or oxygen atoms, where N-oxides, sulfur oxides, and dioxides are permissible heteroatom substitutions and the rings may be optionally substituted, with multiple degrees of substitution being allowed. The term includes ring(s) optionally substituted, with multiple degrees of substitution being allowed, and also includes an optional alkylene linker, such as $C_1$–$C_6$ alkylene, through which the heteroaryl group may be attached. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "cycloalkyl" refers to a mono- or bi-cyclic hydrocarbon ring system, which may be further substituted with multiple degrees of substitution being allowed, and which optionally includes an alkylene linker through which the cycloalkyl may be attached. Exemplary "cycloalkyl" groups include, but are not limited to, cyclopropyl, cyclobutyl, cyclopentyl, cyclohexyl, and cycloheptyl. When substituted, one preferred substituent location for cycloalkyl groups of the present invention is at the "1-position." To illustrate, without limitation, a preferred location for a substituent is represented below with the substituent referred to as "R":

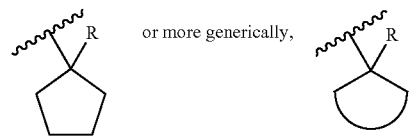

The term "cycloalkyl" includes bridged or fused ring systems, as well, such as hydrindane, decalin, or adamantyl. For ease of reference, also included within the term are cycloalkyl/aryl fused systems where, for example, a cycloalkyl, such as cyclohexyl, is fused with an aromatic ring, such as a benzene ring, to form groups such as

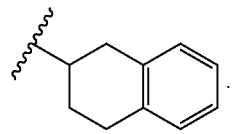

As used herein, the term "heterocyclic" or the term "heterocyclyl" refers to a heterocyclic ring, preferably three to twelve-membered, that is either saturated or has one or more degrees of unsaturation. These heterocyclic rings contain one or more heteroatom, such as nitrogen, sulfur, and/or oxygen atoms, where N-oxides, sulfur oxides, and dioxides are permissible heteroatom substitutions. As used herein heterocyclic groups optionally may be substituted, with multiple degrees of substitution being allowed, and also includes an optional alkylene linker, such as $C_1$–$C_6$ alkylene, through which the heterocyclyl group may be attached. Such a ring may be optionally fused to one or more of another "heterocyclic" ring(s), aryl ring(s), or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

The term "halogen" refers to fluorine, chlorine, bromine, or iodine.

The term "haloalkyl" refers to an alkyl group, as defined herein that is substituted with at least one halogen. Non-limiting examples of "haloalkyl" groups include methyl, ethyl, propyl, isopropyl, n-butyl, and t-butyl substituted independently with one or more halogens, e.g., fluoro, chloro, bromo, and/or iodo. The term "haloalkyl" should be interpreted to include such substituents as perfluoroalkyl, for example, trifluoromethyl, $CF_3$, and the like.

As used herein, the term "haloalkoxy" refers to the group $—OR_a$, where $R_a$ is haloalkyl as herein defined.

As used herein, the term "alkoxy" refers to the group $—OR_a$, where $R_a$ is alkyl as herein defined.

As used herein, the term "aryloxy" refers to the group $—OR_b$, where $R_b$ is aryl as herein defined.

As an example, and to be applied throughout the specification, since the term "aryl" includes optionally substituted aryl groups, the term "aryloxy" includes optionally substituted aryloxy groups. The optional substitution applies for all applicable terms herein defined. Further, as defined above, the term "aryl" includes alkylene-linked aryl groups. Thus, terms such as "aryloxy" and the like should be considered to include alkylene-linked aryl groups. As an example and not meant as limiting, one aryloxy group may be $—OR_b$, where $R_b$ is benzyl.

As used herein, the term "heteroaryloxy" refers to the group $—OR_b$, where $R_b$ is heteroaryl as herein defined.

As used herein, the term "alkoxycarbonyl" refers to the group $—C(O)OR_a$, where $R_a$ is alkyl as herein defined.

As used herein, the term "aryloxycarbonyl" refers to the group $—C(O)OR_a$, where $R_a$ is aryl as herein defined.

As used herein, the term "heteroaryloxycarbonyl" refers to the group $—C(O)OR_a$, where $R_a$ is heteroaryl as herein defined.

As used herein, the term "alkoxythiocarbonyl" refers to the group $—C(S)OR_a$, where $R_a$ is alkyl as herein defined.

As used herein, the term "aryloxythiocarbonyl" refers to the group $—C(S)OR_a$, where $R_a$ is aryl as herein defined.

As used herein, the term "heteroaryloxythiocarbonyl" refers to the group $—C(S)OR_a$, where $R_a$ is heteroaryl as herein defined.

As used herein, the term "oxo" refers to the group $=O$.

As used herein, the term "mercapto" refers to the group $—SH$.

As used herein, the term "thio" shall refer to the group $—S—$.

As used herein, the term "sulfinyl" shall refer to the group $—S(O)—$.

As used herein, the term "sulfonyl" shall refer to the group $—S(O)_2—$.

As used herein, the term "alkylthio" refers to the group $—SR_a$, where $R_a$ is alkyl as herein defined.

As used herein, the term "arylthio" refers to the group $—SR_b$, where $R_b$ is aryl as herein defined.

As used herein, the term "heteroarylthio" refers to the group $—SR_b$, where $R_b$ is heteroaryl as herein defined.

As used herein, the term "alkylsulfinyl" refers to the group $—S(O)R_a$, where $R_a$ is alkyl as herein defined.

As used herein, the term "arylsulfinyl" refers to the group $—S(O)R_b$, where $R_b$ is aryl as herein defined.

As used herein, the term "heteroarylsulfinyl" refers to the group $—S(O)R_b$, where $R_b$ is heteroaryl as herein defined.

As used herein, the term "alkylsulfonyl" refers to the group $—S(O)_2R_a$, where $R_a$ is alkyl as herein defined.

As used herein, the term "cycloalkylsulfonyl" refers to the group $—S(O)_2R_a$, where $R_a$ is cycloalkyl as herein defined.

As used herein the term "arylsulfonyl" refers to the group $—S(O)_2R_b$, where $R_b$ is aryl as herein defined.

As used herein the term "heteroarylsulfonyl" refers to the group $—S(O)_2R_b$, where $R_b$ is heteroaryl as herein defined.

As used herein, the term "aminosulfonyl" refers to the group $—S(O)_2NH_2$.

As used herein, the term "cyano" refers to the group $—CN$.

As used herein the term "cyanoalkyl" refers to the group $—R_aCN$ wherein $R_a$ is an alkylene as herein defined.

As used herein, the term "carboxy" refers to the group $—COOH$.

As used herein, the term "carbamoyl" refers to the group $—C(O)NH_2$.

As used herein, the term "alkylcarbamoyl" refers to the group $—C(O)N(R_a)_2$, where one $R_a$ is alkyl and the other $R_a$ is independently H or alkyl.

As used herein, the term "arylcarbamoyl" refers to the group $—C(O)N(R_a)_2$, where one $R_a$ is aryl and the other $R_a$ is independently H or aryl, as herein defined.

As used herein, the term "heteroarylcarbamoyl" refers to the group $—C(O)N(R_a)_2$, where one $R_a$ is heteroaryl and the other $R_a$ is independently H or heteroaryl, as herein defined.

As used herein, the term "thiocarbamoyl" refers to the group $—C(S)NH_2$.

As used herein, the term "alkylthiocarbamoyl" refers to the group $—C(S)N(R_a)_2$, where one $R_a$ is alkyl and the other $R_a$ is independently H or alkyl.

As used herein, the term "arylthiocarbamoyl" refers to the group $—C(S)N(R_a)_2$, where one $R_a$ is aryl and the other $R_a$ is independently H or aryl, as herein defined.

As used herein, the term "heteroarylthiocarbamoyl" refers to the group $—C(S)N(R_a)_2$ where one $R_a$ is heteroaryl and the other $R_a$ is independently H or heteroaryl, as herein defined.

As used herein, the term "amino" refers to the group $—NH_2$.

As used herein, the term "alkylamino" refers to the group $—N(R_a)_2$, where one $R_a$ is alkyl and the other $R_a$ independently is H or alkyl, as herein defined.

As used herein, the term "cycloalkylamino" refers to the group $—N(R_a)_2$, where one $R_a$ is cycloalkyl and the other $R_a$ independently is H or cycloalkyl, as herein defined.

As used herein, the term "arylamino" refers to the group $—N(R_a)_2$ where one $R_a$ is aryl and the other $R_a$ independently is H or aryl, as herein defined.

As used herein, the term "heteroarylamino" refers to the group $—N(R_a)_2$, where one $R_a$ is heteroaryl and the other $R_a$ independently is H or heteroaryl, as herein defined.

As used herein, the term "acyl" refers to the group $—C(O)R_a$, where $R_a$ is alkyl, aryl, heteroaryl, cycloalkyl, or heterocyclyl, each as herein defined.

As used herein, the term "thioacyl" refers to the group $—C(S)R_a$, where $R_a$ is alkyl, aryl, heteroaryl, cycloalkyl, or heterocyclyl, each as herein defined.

As used herein, the term "hydroxy" refers to the group $—OH$.

As used herein the term "hydroxyalkyl" refers to the group $—R_aOH$ wherein $R_a$ is an alkylene as herein defined.

Also, as used herein throughout the present specification, the phrase "optionally substituted" denotes an optional substitution, one or more times, with, as the terms are herein defined, acyl; alkyl; alkenyl; alkynyl; alkylsulfonyl; alkoxy;

cyano; halogen; haloalkyl; hydroxy; nitro; aryl, which may be further substituted with acyl, alkoxy, alkyl, alkenyl, alkynyl, alkylsulfonyl, cyano, halogen, haloalkyl, hydroxy, or nitro; heteroaryl, which may be further substituted with acyl, alkoxy, alkyl, alkenyl, alkynyl, alkylsulfonyl, cyano, halogen, haloalkyl, hydroxy, or nitro; arylsulfonyl, which may be further substituted with acyl, alkoxy, alkyl, alkenyl, alkynyl, alkylsulfonyl, cyano, halogen, haloalkyl, hydroxy, or nitro; heteroarylsulfonyl, which may be further substituted with acyl, alkoxy, alkyl, alkenyl, alkynyl, alkylsulfonyl, cyano, halogen, haloalkyl, hydroxy, or nitro; aryloxy, which may be further substituted with acyl, alkoxy, alkyl, alkenyl, alkynyl, alkylsulfonyl, cyano, halogen, haloalkyl, hydroxy, or nitro; heteroaryloxy, which may be further substituted with acyl, alkoxy, alkyl, alkenyl, alkynyl, alkylsulfonyl, cyano, halogen, haloalkyl, hydroxy, or nitro; —R'OR'R$^4$; or —NR$^4$R$^5$; where for each occurrence R' is alkylene, alkenylene, or alkynylene, and R$^4$ and R$^5$ are each independently selected from H, alkyl, alkenyl, alkynyl, cycloalkyl, heterocyclyl, aryl, heteroaryl, alkylsulfonyl, arylsulfonyl, or heteroarylsulfonyl, where each occurrence of such aryl or heteroaryl may be substituted with one or more acyl, alkoxy, alkyl, alkenyl, alkylsulfonyl, cyano, halogen, haloalkyl, hydroxy, or nitro, or R$^4$ and R$^5$ may combine to form a ring, optionally having additional heteroatoms, optionally having one or more degrees of unsaturation, and optionally being further substituted with acyl, alkoxy, alkyl, alkenyl, alkynyl, alkylsulfonyl, cyano, halogen, haloalkyl, hydroxy, or nitro.

The compounds of the present invention may have the ability to crystallize in more than one form, a characteristic known as polymorphism. All polymorphic forms ("polymorphs") are within the scope of the present invention. Polymorphism generally can occur as a response to changes in temperature or pressure, or both, and can also result from variations in the crystallization process. Polymorphs can be distinguished by various physical characteristics that are known in the art such as x-ray diffraction patterns, solubility, and melting point.

Certain of the compounds described herein contain one or more chiral centers, or may otherwise be capable of existing as multiple stereoisomers. The scope of the present invention includes pure stereoisomers as well as mixtures of stereoisomers, such as purified enantiomers/diastereomers or enantiomerically/diastereomerically enriched mixtures. Also included within the scope of the invention are the individual isomers of the compounds per se, as well as any wholly or partially equilibrated mixtures thereof. The present invention covers the individual isomers of the compounds represented by the formulas above as mixtures with isomers thereof in which one or more chiral centers are inverted.

As noted above, the present invention includes salts, solvates, and pharmaceutically functional derivatives of the compounds of the present invention. Salts include addition salts, metal salts, or optionally alkylated ammonium salts. Examples of such salts include hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methane sulphonic, ethane sulphonic, picric, and the like. Further salts include lithium, sodium, potassium, magnesium, and the like. Still further salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, laurate, malate, mandelate, mesylate, methylbromide, methylnitrate, methylsulfate, monopotassium maleate, mucate, napsylate, nitrate, N-methylglucamine, pamoate (embonate), palmitate, pantothenate, phosphate/diphosphate, polygalacturonate, potassium, salicylate, sodium, stearate, subacetate, tannate, tartrate, teoclate, tosylate, triethiodide, trimethylammonium, and valerate salts. Reference is also made to Journal of Pharmaceutical Science, 1997, 66, 2, incorporated herein by reference, as relevant to salts.

As used herein, the term "solvate" refers to a complex of variable stoichiometry formed by a solute or a salt or pharmaceutically functional derivative thereof and a solvent. Such solvents for the purpose of the invention should not interfere with the biological activity of the solute. Examples of solvents include, but are not limited to water, methanol, ethanol, and acetic acid. Preferably the solvent used is a pharmaceutically acceptable solvent. Examples of pharmaceutically acceptable solvents include water, ethanol, and acetic acid.

The term "pharmaceutically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are recognizable to those skilled in the art, without undue experimentation. Nevertheless reference is made to the teaching of Burger's Medicinal Chemistry and Drug Discovery, 5$^{th}$ Edition, Vol 1: Principles and Practice, which is incorporated herein by reference to the extent of teaching pharmaceutically functional derivatives. While compounds of the present invention may be administered as the raw chemical, preferably the compounds of the present invention are presented as an active ingredient within a pharmaceutical formulation as known in the art. Accordingly, the present invention further includes a pharmaceutical formulation comprising a compound of the present invention, or salt, solvate, or pharmaceutically functional derivative thereof together with one or more pharmaceutically acceptable carriers. Optionally, other therapeutic and/or prophylactic ("active") ingredients may be included in the pharmaceutical formulation as well. For example, the compounds of the present invention may be combined with other anti-diabetic agents, such as one or more of the following agents: insulin, α-glucosidase inhibitors, biguanides, insulin secretagogue, or insulin sensitizers. Non-limiting examples of α-glucosidase inhibitors include acarbose, emiglitate, miglitol, and voglibose. Non-limiting examples of biguanides include metformin, buformin, and phenformin. Non-limiting examples of insulin secretagogues include sulphonylureas. Non-limiting examples of insulin sensitizers include peroxisome proliferator activated receptor (PPAR) ligands, such as PPAR-γ agonists, for example Actos™ and Avandia™.

Formulations of the present invention include those especially formulated for oral, buccal, parental, transdermal, inhalation, intranasal, transmucosal, implant, or rectal administration. Among the variety of administrations, oral administration typically is preferred. For oral administration tablets, capsules, and caplets may contain conventional excipients such as binding agents, fillers, lubricants, disintegrants, and/or wetting agents. Non-limiting examples of binding agents include syrup, acacia, gelatin, sorbitol, tragacanth, mucilage of starch, or polyvinylpyrrolidone (PVP). Non-limiting examples of fillers include, for example, lactose, sugar, microcrystalline cellulose, maize-starch, calcium phosphate or sorbitol. Non-limiting examples of lubricants include, for example, magnesium sterate, stearic acid, talc, polyethylene glycol or silica. Non-limiting examples of disintegrants include, for example, potato starch or sodium starch glycollate. A non-limiting example of a wetting agent includes sodium lauryl sulfate. The tablets additionally may be coated according to methods known in the art Alternatively, the compounds of the present invention may be incorporated into oral liquid preparations such as aqueous or oily suspensions, solutions, emulsions, syrups, or elixirs. Moreover, formulations containing these compounds may be presented as a dry product for constitution with water or other suitable vehicle before use. Liquid preparations may contain conventional additives. Non-limiting examples of such additives include suspending agents such as sorbitol syrup, methyl cellulose, glucose/sugar syrup, gelatin, hydroxyethylcellulose, carboxymethyl cellulose, aluminum sterate gel or hydrogenated edible fats. Additionally, emulsifying agents such as lecithin, sorbitan monooleate or acacia; non-aqueous vehicles (which may include edible oils) such as almond oil, fractionated coconut oil, oily esters, propylene glycol or ethyl alcohol my be included. Further, preservatives such as methyl or propyl p-hydroxybenzoates or sorbic acid, may be incorporated into the preparation. Such preparations may also be formulated as suppositories, for example, containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, for example, sterile, pyrogen-free water, before use.

The formulations according to the invention may also be formulated as a depot preparation. Such long acting formulations may be administered by implantation, for example, subcutaneously or intramuscularly, or by intramuscular injection. Accordingly, the compounds of the invention may be formulated with suitable polymeric or hydrophobic materials, such as an emulsion in an acceptable oil, ion exchange resins, or as sparingly soluble derivatives, such as a sparingly soluble salt.

Pharmaceutical formulations may be presented in unit dose forms containing a predetermined amount of active ingredient per unit dose. Such a unit may contain certain amounts of a compound of the present invention depending on the condition being treated, the route of administration, and the age, weight and condition of the patient. Examples of such amounts include the formulation containing about 0.1 to about 99.9% active ingredient. Preferred unit dosage formulations are those containing a predetermined dose, such as a daily dose, or an appropriate fraction thereof, of an active ingredient. Such pharmaceutical formulations may be prepared by any of the methods well known in the pharmacy art.

As used herein, the term "effective amount" means that amount of a drug or pharmaceutical agent that will elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The therapeutically effective amount of a compound of the present invention will depend upon a number of factors including, for example, the age and weight of the animal, the precise condition requiring treatment and its severity, the nature of the formulation, and the route of administration. Therapeutic effectiveness ultimately will be at the discretion of the attendant physician or veterinarian. An effective amount of a salt or solvate, or pharmaceutically functional derivative thereof, may be determined as a proportion of the effective amount of a compound of the present invention per se. Dosages may vary, depending upon the appropriate inhibition of DPP-IV for purposes of treatment or prophylaxis of a variety of metabolic, gastrointestinal, viral, and inflammatory diseases, including, but not limited to, diabetes, obesity, hyperlipidemia, dermatological or mucous membrane disorders, psoriasis, intestinal distress, constipation, autoimmune disorders such as encephalomyelitis, complement mediated disorders such as glomerulonephritis, lipodystrophy, and tissue damage, psychosomatic, depressive, and neuropsychiatric disorders, HIV infection, allergies, inflammation, arthritis, transplant rejection, high blood pressure, congestive heart failure, tumors, and stress-induced abortions, for example cytokine-mediated murine abortions.

No toxicological effects are indicated/expected when a compound of the present invention is administered in the above mentioned dosage range.

The following examples illustrate aspects of this invention, but should not be construed as limitations. As used herein the symbols and conventions used in these processes, schemes and examples are consistent with those used in the contemporary scientific literature, for example, the Journal of the American Chemical Society or the Journal of Biological Chemistry. Unless otherwise noted, all starting materials were obtained from commercial suppliers and used without further purification.

$^1$H NMR spectra were recorded on a Varian VXR-300, a Varian Unity-300, a Varian Unity-400 instrument, or a General Electric QE-300. Chemical shifts are expressed in parts per, million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCI EX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230–400 mesh, Merck). Optical rotations were obtained using a Perkin Elmer Model 241 Polarimeter. Melting points were determined using a Mel-Temp II apparatus and are uncorrected.

IUPAC names are included to further identify particular compounds of the present invention. The IUPAC names stated herein should in no way limit the scope of the present invention.

EXPERIMENTALS

In accordance with the present invention and as below, one embodiment of the compounds of the present invention can be prepared by reacting a compound of formula II with an α- or β-amino carboxylate or with an α- or β-amino activated carboxylate, both designated herein generally as aminocarboxylates, under standard coupling conditions, for example, with HATU, DMF, Hunigs base.

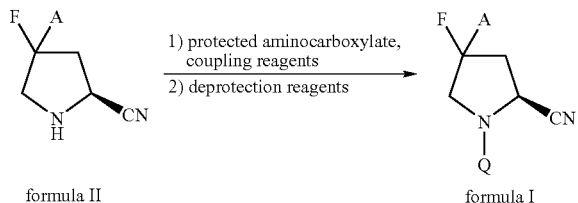

More specifically, a compound of formula II may be reacted with an amino carboxylate, where the amino carboxylate is suitably protected, for example on the α-nitrogen, with an appropriate protecting group such as, for example, a t-butyl carboxy protecting group.

In an alternate embodiment, a compound of formula II may be reacted with an amino activated carboxylate, such as, for example, N-hydroxysuccinimide ester or acid chloride, where the amino activated carboxylate is suitably protected, for example, on the α-nitrogen with an appropriate protecting group such as, for example, a t-butyl carboxy protecting group. Removal of the protecting group under suitable conditions, such as, for example, trifluoroacetic acid for the removal of the t-butyl carboxy, then generates compounds of formula (I).

For further detail regarding the preparation of amino carboxylates for use in preparing the compounds of the present invention, reference may be had to WO 95/15309 and WO 98/19998, each herein incorporated by reference as related to the preparation of such reactants.

Intermediate Example 1

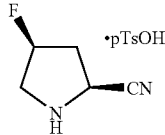

(2S, 4S)-4-Fluoro-2-pyrrolidinecarbonitrile 4-methylbenzenesulfonate

A. Methyl (2S, 4R)-4-hydroxy-2-pyrrolidinecarboxylate hydrochloride

To a MeOH solution (420 mL) containing L-hydroxyproline (62.67 g, 478 mmol) cooled in an ice water bath was added thionyl chloride (58.6 g, 492.3 mmol) dropwise. Upon complete addition the suspension was stirred at RT for 2 h. The mixture was then heated to reflux for 6 h at which time it was cooled to RT and the solvent removed in vacuo. The residual solid was pumped on under high vacuum yielding 86.03 g (474 mmol, 99% yield) of compound A as a white solid.

$^1$H NMR (d$_4$-MeOH) 400 MHz δ 4.62–4.57 (m, 2H), 3.85 (s, 3H), 3.43 (dd, 1H, J=12.2, 3.7 Hz), 3.30 (m, 1H), 2.41 (dd, 1H, J=13.6, 7.6 Hz), 2.19 (m, 1H) ppm.

B. 1-Tert-butyl-2-methyl (2S, 4R)-4-hydroxy-1,2-pyrrolidinedicarboxylate.

To a CH$_2$Cl$_2$ solution (1.4 L) containing compound A (88.67 g, 0.49 mol) and di-t-butyldicarbonate (109.8 g, 0.50 mol) was added, at 0° C., triethylamine (123.6 g, 1.22 mol) dropwise over 1.5 h. The resulting solution was then slowly allowed to warm to RT overnight. The solvent was then removed in vacuo and Et$_2$O was added to the residual solid. The solid was collected via vacuum filtration and washed thoroughly with Et$_2$O. The filtrate then had the solvent removed in vacuo and was dissolved in CH$_2$Cl$_2$. The organics were washed with sat. NaCl and sat NaHCO$_3$ followed by drying over MgSO$_4$. Filtration and removal of the solvent in vacuo yielded a light yellow oil which, after pumping on under high vacuum for ~15 min., solidified. The resulting solid had 500 mL of hexanes added to it and then stirred overnight. The solid was collected via vacuum filtration and pumped on under high vacuum yielding 104.5 g (0.43 mol, 87% yield) compound B as a white solid.

$^1$H NMR (d$_4$-MeOH) 400 MHz δ 4.37–4.32 (m, 2H), 3.72–3.71 (m, 3H), 3.51 (m, 1H), 3.43 (m, 1H), 2.23 (m, 1H), 2.02 (m, 1H), 1.42 (m, 9H) ppm.

C. 1-Tert-butyl 2-methyl (2S, 4S)-4-fluoro-1,2-pyrrolidinedicarboxylate.

To a 2 L flask containing compound B (124.25 g, 0.51 mol), in 1.25 L of 1,2-dichloroethane cooled to –30° C., was added DAST neat (125 g 0.78 mol). The reaction slowly warmed to –10° C. over 1 hr at which time the cold bath was removed. Stirring continued at RT for 24 hr when the dark solution was poured into two 2 L flasks that contained crushed ice and solid NaHCO$_3$. The flasks were periodically swirled and stirred until no CO$_2$ evolution was observed (note: additional solid NaHCO$_3$ was periodically added). The organic layer was separated and the aqueous layer extracted with CH$_2$Cl$_2$. After drying over MgSO$_4$ the solvent was removed in vacuo and the residual dark oil was dissolved in 200 mL of EtOAc and then 800 mL of hexanes was added. To this solution was added 100 g of SiO$_2$. After stirring for 30 min the solution was filtered with the SiO$_2$ being washed with hexanes/EtOAc (4:1, ~500 mL). Removal of the solvent in vacuo and pumping on under high vacuum overnight yielded 121.81 g (0.40 mol, 97% yield) of compound C as a dark oil.

$^1$H NMR (CDCl$_3$) 400 MHz δ 5.18 (d(br), 1H, J=53 Hz), 4.53 (d, 1/2H, J=9.7 Hz), 4.40 (d, ½H, J=9.4 Hz), 3.87–3.59 (m, 2H), 3.73 (s, 3H), 2.51–2.28 (m, 2H), 1.46 (s, 3H, rotomer), 1.41 (s, 6H, rotomer) ppm.

D. (2S, 4S)-1-(Tert-butoxycarbonyl)-4-fluoro-2-pyrrolidinecarboxylic acid.

To a 2 L flask containing compound C (121.8 g, 0.49 mol), in 1.1 L of dioxane, was added 380 mL of H$_2$O followed by lithium hydroxide hydrate (103.6 g, 2.46 mol) at RT. The resulting solution stirred for 23 hr (note: by TLC the reaction appeared to be done after 5 hr) at which time the bulk of the dioxane was removed in vacuo. The residual material was dissolved in additional H$_2$O and then charcoal was added. After stirring for 15 min., the solution was filtered through a bed of celite. The filtrate had solid NaCl added to it until it didn't dissolve any further. It was then cooled in an ice water bath and was acidified with concentrated HCl to pH 3 whilst maintaining the solution temperature between 5–10° C. The product began to precipitate out at pH 4 and upon reaching pH 3 the tan solid was collected via vacuum filtration. After pumping on under high vacuum overnight the solid was dissolved in CH$_3$CN (1.5 L) and dried over MgSO₄. Removal of the solvent in vacuo and drying under high vacuum yielded 92.7 g (0.40 mol, 81% yield) of compound as a tan solid.

$^1$H NMR (d$_6$-DMSO) 400 MHz δ 12.5 (s(br), 1H), 5.22 (d(br), 1H, J=54 Hz), 4.25 (m, 1H), 3.60–3.43 (m, 2H), 2.45 (m, 1H), 2.20 (m, 1H), 1.33 (m, 9H) ppm.

E. Tert-butyl (2S, 4S)-2-(aminocarbonyl)-4-fluoro-1-pyrrolidinecarboxylate.

To a 2 L, 3-neck flask equipped with an air-driven stirrer was added compound D (92.7 g, 0.40 mol), CH₃CN (1.1 L), di-t-butyldicarbonate (130 g, 0.60 mol), and pyridine (32.4 g, 0.41 mol) at RT. After stirring for 20 min., ammonium hydrogen carbonate (47.2 g, 0.60 mol) was added. The reaction stirred for 23 hr at which time the bulk of the CH₃CN was removed in vacuo. The residue was then dissolved in CH₂Cl₂ and washed with a 1:1 1M HCl/sat. NaCl solution. The aqueous layer was then extracted 2× with CH₂Cl₂. The combined organic layers were dried (MgSO₄) and the solvent removed in vacuo. The tan solid was triturated with hexanes (~0.5 L) and collected via vacuum filtration. After pumping under high vacuum, 68.75 g (0.30 mol, 74% yield) compound E was obtained as a light tan solid. The filtrate after removal of the solvent in vacuo gave a dark oil that also appeared to contain additional product by $^1$H NMR.

$^1$H NMR (d$_6$-DMSO) 400 MHz δ 7.21 (s(br), ½H), 7.14 (s(br), ½H), 6.94 (s(br), 1H), 5.19 (d(br), 1H, J=54 Hz), 4.11 (m, 1H), 3.63–3.47 (m, 2H), 2.38 (m, 1H), 2.11 (m, 1H), 1.39 (s, 3H, rotomer), 1.34 (s, 6H, rotomer) ppm.

F. Tert-butyl (2S, 4S)-2-cyano-4-fluoro-1-pyrrolidinecarboxylate.

To a flask containing imidazole (2.93 g, 43.1 mmol), was added pyridine (75 g, 0.9 mol, 15 volumes by weight to the amide). The solution was then cooled to 0° C. and after stirring for 10 min., BOC-4-fluoroproline carboxamide (5.0 g, 21.6 mmol) was added in one portion. The solution was then cooled to −30° C. (note: going below this temperature may lead to a heterogeneous solution) and POCl₃ (13.2 g, 86.4 mmol) was added dropwise over 5 minutes. Upon complete addition the dry-ice acetone bath was replaced with an ice water bath and stirring continued at 0° C. for 1 hr at which time it was poured into a crushed ice, solid NaCl and EtOAc mixture. The organic layer was separated and the aqueous layer was extracted with EtOAc (2×). The solvent was removed in vacuo (note: keep rotovap bath <35° C.) and the residue dissolved in EtOAc. The organics were washed with sat NaCl and 1 M HCl (2×). After drying over MgSO₄ the solvent was removed in vacuo yielding 4.0 g (18.6 mmol, 86% yield) of compound F as a light tan solid.

$^1$H NMR (d$_4$-MeOH) 400 MHz δ 5.32 (d(br), 1H, J=52 Hz), 4.78 (m, 1H), 3.74–3.48 (m, 2H), 2.55–2.40 (m, 2H), 1.52–1.43 (m, 9H) ppm.

G. (2S, 4S)-4-Fluoro-2-pyrrolidinecarbonitrile 4-methylbenzenesulfonate.

To a CH₃CN solution (1 L) containing compound F (56.62 g, 0.26 mol), was added p-toluenesulfonic acid hydrate (75.4 g, 0.40 mol) at RT. After 24 hr the CH₃CN was removed in vacuo and then the residual brown oil was dissolved in 500 mL of EtOAc. Within 1 min a solid precipitated out and the solution was cooled in an ice-water bath and after stirring for 1 hr the solid was collected via vacuum filtration. The collected solid was rinsed with cold (−20° C.) EtOAc (~500 mL) and then pumped on under high vacuum overnight yielding 60.94 g (0.21 mol, 82% yield) of compound G as a light tan solid.

$^1$H NMR (d$_4$-MeOH) 400 MHz δ 7.69 (d, 2H, J=8.1 Hz), 7.23 (d, 2H, J=8.0 Hz), 5.52 (dd, 1H, J=51, 3.4 Hz), 4.96 (dd, 1H, J=9.8, 3.6 Hz), 3.78 (m, 1H), 3.55 (m, 1H), 2.84–2.63 (m, 2H), 2.36 (s, 3H) ppm.

Alternative Route for Intermediate Example 1

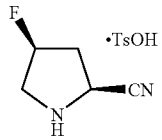

(2S, 4S)-4-Fluoro-2-pyrrolidinecarbonitrile 4-methylbenzenesulfonate

Tert-butyl (2S,4R)-2-(aminocarbonyl)-4-hydroxypyrrolidine-1-carboxylate

To a THF solution (420 mL) containing BOC-L-hydroxyproline (30.0 g, 129 mmol) and triethylamine (14.4 g, 141.9 mmol) cooled to −15° C. was added ethyl chloroformate (15.4 g, 141.9 mmol) dropwise. The resulting solution stirred for 10 min when 80 mL of 28% NH₄OH was added. The reaction was allowed to slowly warm to 5° C. over 2 hr at which time sat NH₄Cl was added until the entire white solid had dissolved. The THF was separated and the aqueous layer extracted with THF. The combined organic layers were dried (MgSO₄) and the solvent removed in vacuo. The residual oil was treated with Et₂O and a small amount of CH₂Cl₂ and MeOH. After storing in the freezer for 1 hr the resulting white solid was collected via vacuum filtration yielding 22.0 g (95.6 mmol, 74% yield) of compound A.

$^1$H NMR (d$_6$-DMSO) 400 MHz δ 7.33–7.29 (d(br), 1H, rotomers), 6.88–6.80 (d(br), 1H, rotomers), 4.94 (s(br), 1H), 4.18 (s(br), 1H), 4.04 (m, 1H), 3.35 (m, 1H), 3.21 (m, 1H), 1.99 (m, 1H), 1.77 (m, 1H), 1.36–1.31 (d, 9H, rotomers) ppm.

B. Tert-butyl (2S,4R)-2-cyano-4-hydroxypyrrolidine-1-carboxylate.

To a pyridine solution (180 mL) containing compound A (17.89 g, 77.8 mmol) cooled to −20° C. was added trifluoroacetic anhydride (40.8 g, 194.4 mmol) dropwise. Upon complete addition the reaction was allowed to warm to RT. After 6 hr the reaction was quenched with H₂O and then poured into EtOAc (ca 500 mL). The organics were washed with sat. NaCl, 1.0 M HCl and 2.0 M NaOH followed by drying over MgSO₄. The filtrate had charcoal added to it and after stirring for 10 min the solution was filtered through a bed of celite. The solvent was removed in vacuo (the rotovap temperature was at 34° C.) yielding 13.21 g (62.3 mmol, 80% yield) of compound B as an orange oil.

$^1$H NMR (d$_4$-MeOH) 400 MHz δ 4.60 (m, 1H), 4.40 (s(br), 1H), 3.49–3.41 (m, 2H), 2.36–2.34 (m, 2H), 1.51–1.48 (m, 9H, rotomers)

C. Tert-butyl (2S, 4S)-2-cyano-4-fluoro-1-pyrrolidinecarboxylate.

To a 1,2-dichloroethane solution (300 mL) containing compound B (13.21 g, 62.3 mmol) cooled to −30° C. was added DAST (15.1 g, 93.4 mmol). After 30 min the cold bath was removed and stirring continued for 24 hr at which time the reaction was quenched carefully with sat. NaHCO₃. The solution was then poured onto crushed ice and the organics extracted with CH₂Cl₂ (2×). After a final washing with sat. NaHSO₄ the organics were dried (MgSO₄) and the solvent removed in vacuo yielding 10.86 g (50.7 mmol, 81% yield) of compound C as a brown semi-solid.

$^1$H NMR (d$_4$-MeOH) 400 MHz δ 5.32 (d(br), 1H, J=52 Hz), 4.78 (m, 1H), 3.74–3.48 (m, 2H), 2.55–2.40 (m, 2H), 1.52–1.43 (m, 9H) ppm.

D. (2S, 4S)-4-Fluoro-2-pyrrolidinecarbonitrile 4-methylbenzenesulfonate.

To an CH$_3$CN solution (200 mL) containing compound C (10.86 g 50.7 mmol) was added p-toluenesulfonic acid (14.8 g, 78 mmol) at RT. The resulting solution stirred for 24 hr at which time the CH$_3$CN was removed in vacuo. The residual brown oil was dissolved in EtOAc (300 mL) and within 1 min a solid precipitated out. The solution was cooled in an ice-bath for 2 hr and then the solid collected via vacuum filtration. It was then washed with 300 mL of cold (−20° C.) EtOAc yielding 10.07 g (35.2 mmol, 69% yield) of compound D.

$^1$H NMR (d$_4$-MeOH) 400 MHz δ 7.69 (d, 2H, J=8.1 Hz), 7.23 (d, 2H, J=8.0 Hz), 5.52 (dd, 1H, J=51, 3.4 Hz), 4.96 (dd, 1H, J=9.8, 3.6 Hz), 3.78 (m, 1H), 3.55 (m, 1H), 2.84–2.63 (m, 2H), 2.36 (s, 3H) ppm.

Intermediate Example 2

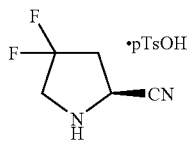

(2S)-4,4-Difluoro-2-pyrrolidinecarbonitrile 4-methylbenzenesulfonate

A. Tert-butyl (2S, 4S)-2-(aminocarbonyl)-4-hydroxy-1-pyrrolidinecarboxylate.

To a THF solution (420 mL) containing BOC-L-hydroxyproline (30.0 g, 129 mmol) and Et$_3$N (14.4 g, 141.9 mmol) cooled to −15° C. was added ethyl chloroformate (15.4 g, 141.9 mmol) dropwise. The resulting white solution stirred at −15° C. for 30 min when 80 mL of a 28% NH$_4$OH solution was added via syringe. Upon complete addition the cold bath was removed and stirring continued for 19 hr. The homogeneous solution was poured into sat. NH$_4$Cl and the organic layer separated. The aqueous layer was extracted with THF and then the combined organic layers dried (MgSO$_4$). The solvent was removed in vacuo and the semisolid pumped under high vacuum for 2 hr. The resulting white solid was collected via vacuum filtration with Et$_2$O yielding 15.86 g (68.9 mmol, 53% yield) of compound A.

$^1$H NMR (d$_6$-DMSO) 400 MHz δ 7.34 (s(br), 1H, rotomer), 7.31 (s(br), 1H, rotomer), 6.90 (s(br), 1H, rotomer), 6.82 (s(br), 1H, rotomer), 4.95 (d, 1H, J=3.1 Hz), 4.05 (m, 1H), 3.36 (m, 1H), 3.22 (m, 1H), 2.03 (m, 1H), 1.78 (m, 1H), 1.37 (s, 3H, rotomer), 1.32 (s, 6H, rotomer) ppm.

B. Tert-butyl (2S)-2-(aminocarbonyl)-4-oxo-1-pyrrolidinecarboxylate.

To a CH$_2$Cl$_2$ solution (12 mL) containing oxalyl chloride (607 mg, 4.78 mmol) cooled to −78° C. was added a CH$_2$Cl$_2$ solution (3 mL) containing DMSO. After 5 min tert-butyl (2S, 4S)-2-(aminocarbonyl)-4-hydroxy-1-pyrrolidinecarboxylate (1.0 g, 4.35 mmol, as described in step E above) in a CH$_2$Cl$_2$/THF solution (20 mL/15 mL) was added dropwise. Upon complete addition the reaction stirred for 20 min when Et$_3$N (2.20 g, 21.7 mmol) was added. After 10 min the cold bath was removed and stirring continued for 1 hr. The solution was poured into sat. NaHCO$_3$ and the organics extracted with CH$_2$Cl$_2$. After drying over MgSO$_4$ the solvent was removed in vacuo and the residual yellow oil purified via column chromatography (CH$_2$Cl$_2$/MeOH (15:1)) yielding 560 mg (2.45 mmol, 56% yield) of compound B as a white solid.

$^1$H NMR (d$_6$-DMSO) 400 MHz δ 7.58 (s(br), 1H), 7.15 (s(br), 1H, rotomer), 7.09 (s(br), 1H, rotomer), 4.51 (d, 1H, J=9.7 Hz, rotomer), 4.46 (d, 1H, J=8.8 Hz, rotomer), 3.76–3.64 (m, 2H), 3.02 (m, 1H), 2.28 (m, 1H), 1.39 (s, 3H, rotomer), 1.37 (s, 6H, rotomer) ppm.

C. Tert-butyl (2S)-2-(aminocarbonyl)-4,4-difluoro-1-pyrrolidinecarboxylate.

To a CH$_2$Cl$_2$ solution (10 mL) containing compound B (423 mg, 1.85 mmol) cooled to −70° C. was added DAST (889 mg, 5.50 mmol). The resulting solution stirred at −70° C. for 30 min and then at RT for 2 hr. The reaction was quenched with sat. NaHCO$_3$ and the organics extracted with CH$_2$Cl$_2$. After drying over MgSO$_4$ the residual yellow solid was purified via column chromatography (CH$_2$Cl$_2$/MeOH (15:1)) yielding 211 mg (0.84 mmol, 46% yield) of compound C.

$^1$H NMR (d$_4$-MeOH) 400 MHz δ 4.38 (m, 1H), 3.84–3.75 (m, 2H), 2.76 (m, 1H), 2.41 (m, 1H), 1.44 (s(br), 9H) ppm.

D. Tert-butyl (2S)-2-cyano-4,4-difluoro-1-pyrrolidinecarboxylate.

To a pyridine solution (20 mL) containing compound C (658 mg, 2.63 mmol) and imidazole (358 mg, 5.26 mmol) cooled to −35° C. was added POCl$_3$ (1.61 g, 10.5 mmol). The resulting slurry stirred for 1.5 hr at which time it had warmed to 10° C. The solution was diluted with EtOAc and them washed 3× with 1 M HCl. After drying over MgSO$_4$ the solvent was removed in vacuo yielding 610 mg (2.63 mmol, 100% yield) of compound D which was taken directly on to E (below).

$^1$H NMR (d$_4$-MeOH) 400 MHz δ 4.88 (s(br), 1H), 3.79–3.72 (m, 2H), 2.87 (m, 1H), 2.69 (m, 1H), 1.50 (s, 9H) ppm.

E. (2S)-4,4-Difluoro-2-pyrrolidinecarbonitrile 4-methylbenzenesulfonate.

To a CH$_3$CN solution (15 mL) containing compound D (512 mg, 2.21 mmol) was added p-toluenesulfonic acid hydrate (839 mg, 4.42 mmol) at RT. The resulting solution stirred for 2 hr at which time the CH$_3$CN was removed in vacuo. To the residual oil was added EtOAc (~10 mL) and this was then removed in vacuo. The resulting solid was triterated with Et$_2$O followed by addition of EtOAc. The solid was collected via vacuum filtration yielding 375 mg (1.23 mmol, 56% yield) of compound E as a white solid.

$^1$H NMR (d$_4$-MeOH) δ 400 MHz δ 7.70 (d, 2H, J=8.2 Hz), 7.23 (d, 2H, J=7.9 Hz), 5.12 (t, 1H, J=7.9 Hz), 3.91–3.78 (m, 2H), 3.08–2.89 (m, 2H), 2.89 (s, 3H), 2.36 (s, 9H) ppm.

EXAMPLES

Example 1

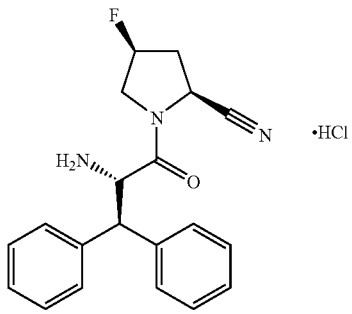

(2S,4S)-1-[(2S)-2-Amino-3,3-diphenylpropanoyl]-4-fluoropyrrolidine-2-carbonitrile hydrochloride A. (2S,4S)-1-[(2S)-2-Amino-3,3-diphenylpropanoyl]-4-fluoropyrrolidine-2-carbonitrile hydrochloride.

To dry DMF (25 mL) was added (2S)-2-[(tert-butoxycarbonyl)amino]-3,3-diphenylpropanoic acid (1.96 g, 6.0 mmol), HATU (2.28 g, 6.0 mmol) and N,N-diisopropylethylamine (1.05 mL, 6.0 mmol). After stirring at RT for 30 min (2S, 4S)-4-fluoro-2-pyrrolidinecarbonitrile 4-methylbenzenesulfonate (1.31 g, 4.5 mmol) and additional N,N-diisopropylethylamine (0.783 mL, 4.5 mmol) were added. This solution was allowed to stir at RT for 12 hr and then saturated sodium bicarbonate (110 mL) was added. The mixture was extracted with ethyl acetate (2×100 mL) and the organics were washed with saturated NaCl (100 mL), dried over MgSO$_4$ and concentrated to dryness to give a crude solid. The solid was chromatographed (silica gel, hexanes/EtOAc 4:1) to provide a solid which was stirred in a dioxane-HCl (4.0 M, 20 mL) solution for 2 hrs followed by the addition of diethyl ether (100 mL). The resulting precipitate was collected by filtration and dried under high vacuum yielding 1.36 g (3.64 mmol, 81% yield) of compound A as a white solid.

$^1$H NMR (d$_6$-DMSO) 400 MHz δ 8.45–8.41 (s(br), 3H), 7.70 (m, 2H), 7.38–7.36 (m, 2H), 7.29–7.26 (m, 3H), 7.24–7.18 (m, 3H), 5.39 (d, 1H, J=51 Hz), 4.89–4.85 (m, 2H), 4.38 (d, 1H, J=11.3 Hz), 3.98 (ddd, 1H, J=38.8, 12.4 et 3.1 Hz), 3.39–3.33 (m, 1H), 2.30–2.18 (m, 2H) ppm.

Example 2

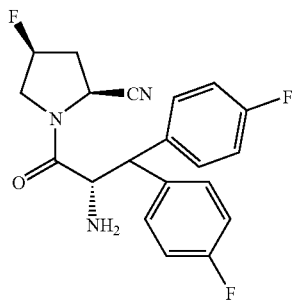

(2S,4S)-1-[(2S)-2-Amino-3,3-bis(4-fluorophenyl)propanoyl]-4-fluoropyrrolidine-2-carbonitrile hydrochloride A. 3,3-Bis(4-fluorophenyl)-3-hydroxypropanoic acid.

To an anhydrous THF (80 mL) solution of n-butyl lithium (46 mL of 2.5 M, 115 mmol) at 0° C. was added dropwise diisopropylamine (11.13 g, 115 mmol) and the solution stirred for 10 minutes. Keeping the solution at 0° C., acetic acid (2.64 g, 44 mmol) was added dropwise and the mixture stirred for 10 min and it was then heated 50° C. After 30 min a heavy precipitate had formed and the solution was allowed to cool. A solution of 4,4'-diflurobenzophenone (9.6 g, 0.044 mol) in THF (50 mL, anhydrous) was added at 0° C., and the solution stirred at room temperature overnight. Water (100 mL) and diethyl ether (100 mL) were added and the aqueous layer was separated and acidified with 1M HCl to pH 3. The organics were extracted with ethyl acetate (3×200 mL) followed by drying over MgSO$_4$. Filtration and removal of the solvent in vacuo yielded a crude white solid that could be washed with cold CHCl$_3$ to remove trace amounts of the benzophenone. The solid was dried under high vacuum yielding 5.63 g (20.2 mmol, 46% yield) of compound A as a white solid.

$^1$H NMR (d$_6$-DMSO) 400 MHz δ 12.4 (s(br), 1H), 7.48–7.39 (m, 4H), 7.19–7.02 (m, 4H), 5.91 (s(br), 1H), 3.25 (s, 2H) ppm.

B. 3,3-Bis(4-fluorophenyl)acrylic acid.

To a 20% solution of sulfuric acid in acetic acid (50 mL, V/V) was compound A (5.6 g, 20.2 mmol) and the mixture stirred for 30 minutes at RT. To this solution was added H$_2$O (500 mL) and the organics were extracted with ethyl acetate (3×150 mL) followed by drying over MgSO$_4$. Filtration and removal of the solvent in vacuo yielded a white solid. The solid was dried under high vacuum yielding 4.97 g (19.1 mmol, 95% yield) of compound B as a white solid.

$^1$H NMR (CDCl$_3$) 400 MHz δ 7.27–7.21 (m, 2H), 7.19–7.13 (m, 2H), 7.10–6.95 (m, 4H), 6.26 (s, 1H) ppm.

C. 3,3-Bis(4-fluorophenyl)propanoic acid.

To a solution of compound B (2.5 g, 9.61 mmol) in ethyl acetate (250 mL) was added 10% palladium on carbon (50% w/w) and hydrogenated at 1 atmosphere of hydrogen for 12 hours. The heterogeneous solution was filtered through celite and concentrated in vacuo to provide a yellow oil. The oil was dried under high vacuum yielding 2.40 g (9.16 mmol, 95% yield) of compound C as a yellow oil.

$^1$H NMR (d$_6$-DMSO) 400 MHz δ 12.08 (brs, 1H), 7.40–7.30 (m, 4H), 7.15–7.05 (m, 4H), 4.45 (t, 1H, J=8.1 Hz), 3.05(d, 2H, J=8.1 Hz) ppm.

D. (4S,5R)-3-[3,3-Bis(4-fluorophenyl)propanoyl]-4-methyl-5-phenyl-1,3-oxazolidin-2-one.

To a THF (50 mL, anhydrous) containing compound C (2.0 g, 7.63 mmol) was added N,N-diisopropylethylamine (1.18 g, 9.16 mmol) and then the solution cooled to −78° C. To this solution was added trimethylacetyl chloride (0.97 g, 8.01 mmol) and the solution warmed to 0° C. over 1 hour. The cloudy mixture was filtered and the filtrate added slowly over 10 min to a solution of the lithiated (4S,5R)-(−)-4-methyl-5-phenyl-2-oxazolidinone at −78° C., which was prepared by the dropwise addition of n-butyl lithium (3.0 mL of 2.5 M, 7.63 mmol) to a THF (50 mL) solution of (4S,5R)-(−)-4-methyl-5-phenyl-2-oxazolidinone (1.35 g, 7.63 mmol) at −78° C. which had stirred for 10 min to provide the lithiated (4S,5R)-(−)-4-methyl-5-phenyl-2-oxazolidinone. The yellow mixture was warmed to 0° C. and quenched with H$_2$O (50 mL) and extracted with diethyl ether (3×250 mL) followed by drying over MgSO$_4$. Filtration and removal of the solvent in vacuo yielded a solid. Flash chromatography (silica gel, 20% ethyl acetate/hexanes) provided compound D. The white solid was dried under high vacuum yielding 2.31 g (5.49 mmol, 72% yield) as a white solid.

$^1$H NMR (d$_6$-DMSO) 400 MHz δ 7.40–7.25 (m, 9H), 7.18–7.02 (m, 4H), 5.76 (d, 1H, J=7.6 Hz), 4.65 (m, 1H), 4.58 (t, 1H, J=7.6 Hz), 3.72 (dd, 1H, J=16.8, 7.0 Hz) 3.57 (dd, 1H, J=16.8, 7.0 Hz), 0.58 (d, 3H, J=6.7 Hz) ppm.

E. (4S,5R)-3-[(2S)-2-Azido-3,3-bis(4-fluorophenyl)propanoyl]-4-methyl-5-[(1E,3Z)-1-methylhexa-1,3,5-trienyl]-1,3-oxazolidin-2-one.

To a THF (50 mL anhydrous) solution containing compound D (2.0 g, 4.75 mmol) at −78° C. was added dropwise potassium bis(trimethylsilyl)amide (10.0 mL of 0.5 M toluene solution, 4.98 mmol). After stirring for 10 min 2,4,6-triisopropylbenzenesulfonyl azide (trisyl azide) (1.84 g, 5.94 mmol) in THF (10 mL, anhydrous) was added in one portion. After 3 minutes acetic acid was added (1.31 g, 21.8 mmol) at −78° C. and then the reaction quickly warmed to 30° C. and stirred for 1 hr at that temperature generating a light yellow solution. To this solution was added H$_2$O (100 mL) and the organics were extracted with ethyl acetate (500 mL). After washing with sat NaHCO$_3$ (100 mL) and drying over MgSO$_4$ the solvent was reomved in vacuo yielding a yellow oil. Column chromatography (ethyl acetate/hexanes 1:9) provided compound E as a white solid. HPLC showed a single diastereoisomer. The white solid was dried under high vacuum yielding 1.71 g (3.70 mmol, 78% yield) as a white solid.

$^1$H NMR (CDCl$_3$) 400 MHz δ 7.42–7.35 (m, H), 7.25–7.18 (m, H), 7.10–7.06 (m, 2H), 7.05–6.92 (m, 2H), 5.95 (d, 1H, J=10.8 Hz), 5.05 (d, 1H, J=7.1 Hz), 4.60 (d, 1H, J=10.8 Hz), 4.38 (m, 1H), 0.95 (d, 3H, J=6.8 Hz) ppm.

F. (2S)-2-Azido-3,3-bis(4-fluorophenyl)propanoic acid.

To a THF/H$_2$O (4:1, 50 mL) solution of compound E (1.5 g, 3.25 mmol) at 0° C. was added a solution of lithium hydroxide (0.272 g, 6.49 mmol) in hydrogen peroxide (1.50 mL of 30% soln in H$_2$O, 48.75 mmol). The mixture was stirred at 0° C. for 1 hr and then quenched with Na$_2$SO$_4$ (6.3 g, 50 mL of 1.0 M solution in H$_2$O). The THF was removed in vacuo and the solution acidified to pH 1 with 6.0 M HCl at 0° C. The organics were extracted with ethyl acetate (2×200 mL) followed by drying over MgSO$_4$. Filtration and removal of the solvent in vacuo yielded a clear oil. Column chromatography (EtOAc/hexanes/acetic acid 50:50:1) provided compound F as a white solid. The solid was dried under high vacuum yielding 0.78 g (2.60 mmol, 80% yield) as a white solid.

$^1$H NMR (CDCl$_3$) 400 MHz δ 9.60(s(br), 1H), 7.25–7.10 (m, 4H), 7.10–6.95 (m, 4H), 4.50 (d, 2H, J=8.6 Hz) ppm.

G. (2S)-2-Amino-3,3-bis(4-fluorophenyl)propanoic acid.

To an ethyl acetate (250 mL) solution of compound F (1.5 g, 4.95 mmol) was added 10% palladium on carbon (10% w/w) and hydrogenated at 1 atmosphere of hydrogen for 12 hr. The heterogeneous solution was filtered through celite (1 g) and the filtrate concentrated in vacuo to provide a clear oil. The oil was dried under high vacuum yielding 1.30 g (4.70 mmol, 95% yield) of compound G as a white solid.

$^1$H NMR (d$_6$-DMSO) 400 MHz δ 10.2(s(br), 1H), 7.38–7.27(m, 4H), 7.08–6.98 (m, 4H), 4.25 (d, 1H, J=8.3 Hz), 3.95 (d, 1H, J=8.3 Hz) ppm.

H. (2S)-2-[(tert-Butoxycarbonyl)amino]-3,3-bis(4-fluorophenyl)propanoic acid.

To a CH$_2$Cl$_2$ (150 mL) solution containing compound G (1.30 g, 4.69 mmol) was added triethylamine (2.37 g, 23.4 mmol) and di-tert-butyl dicarbonate (1.23 g, 5.63 mmol). After stirring for 12 hr H$_2$O (50 mL) and CH$_2$Cl$_2$ (300 mL) were added and the solution acidified to pH 3 with 1.0 M HCl. Separation of the ethyl acetate layer followed by drying over MgSO$_4$ and removal of the solvent in vacuo yielded a clear oil. The oil was dried under high vacuum yielding 1.68 g (4.4 mmol, 95% yield) of compound H as a white solid.

$^1$H NMR (d$_6$-DMSO) 400 MHz δ 12.4 (s(br), 1H), 7.35–7.22 (m, 4H), 7.15–6.95 (m, 4H), 4.78 (t, 1H, J=8.9 Hz), 4.25 (d, 1H, J=8.9 Hz), 3.05 (m, 1H), 1.20 (s, 3H), 1.15 (s, 6H) ppm.

I. (2S,4S)-1-[(2S)-2-(tert-Butoxycarbonyl)amino-3,3-bis(4-fluorophenyl)propanoyl]-4-fluoropyrrolidine-2-carbonitrile.

To a DMF solution (25 mL anhydrous) was compound H (1.0 g, 2.65 mmol) and HATU (1.0 g, 2.65 mmol). To this solution was added N,N-diisopropylethylamine (0.462 mL, 2.65 mmol) and after 30 min (2S, 4S)-4-fluoro-2-pyrrolidinecarbonitrile 4-methylbenzenesulfonate (0.619 g, 2.12 mmol) and additional N,N-diisopropylethylamine (0.37 mL 2.12 mmol) were added. This solution was allowed to stir at RT for 12 hr and then saturated sodium bicarbonate (100 mL) was added. The resulting gummy mixture was extracted with ethyl acetate (3×100 mL) and the organics were washed with saturated NaCl (50 mL) followed by drying over MgSO$_4$. Filtration and removal of the solvent in vacuo yielded a clear oil. The oil was chromatographed on silica gel (hexanes/EtOAc 4:1) to provide a white solid. The solid was dried under high vacuum yielding 815 mg (1.72 mmol, 65% yield) of compound I as a white solid.

$^1$H NMR (CDCl$_3$) 400 MHz δ 7.38–7.32 (m, 2H), 7.21–7.15 (m, 2H), 7.12–6.98(m, 4H), 5.15 (d, 1H, J=51 Hz), 5.03 (d, 1H, J=8.9 Hz, 4.89 (d, 1H, J=11.2 Hz), 4.86 (d, 1H, J=8.9 Hz), 4.40 (d, 1H, J=11.2 Hz), 3.83 (ddd, 1H, J=36.8, 12.1, 3.7 Hz), 3.05 (d, 1H, J=12.2 Hz), 2.62 (t, 1H, J=15.3 Hz), 2.25 (m, 1H), 1.38 (s, 9H) ppm.

J. (2S,4S)-1-[(2S)-2-Amino-3,3-bis(4-fluorophenyl)propanoyl]-4-fluoropyrrolidine-2-carbonitrile hydrochloride.

To compound I (0.5 g, 1.05 mmol) was added 4.0 N HCl in 1,4-dioxane (10 mL, 40 mmol) and after 3 hr diethyl ether (100 mL) was added. The resulting precipitate was collected by filtration and after drying under high vacuum 0.41 g (1.0 mmol, 95% yield) of compound J was obtained as a white solid.

$^1$H NMR (d$_6$-DMSO) 400 MHz δ 8.42 (s(br), 3H), 7.72–7.66 (m, 2H), 7.38–7.32 (m, 2H), 7.25–7.19 (m, 2H), 7.06–7.0 (m, 2H), 5.38 (d, 1H, J=51 Hz), 4.91 (d, 2H, J=8.8 Hz), 4.82 (d, 1H, J=11.3 Hz), 4.41 (d, 1H, J=11.3 Hz), 3.86 (ddd, 1H, J=39.2, 12.4, 3.1 Hz), 3.45 (q, 1H, J=12.4 Hz), 2.38–2.20 (m, 2H) ppm.

Example 3

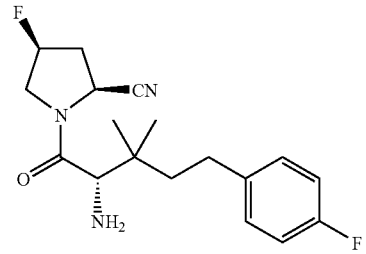

(2S,4S)-1-[(2S)-2-Amino-5-(4-fluorophenyl)-3,3-dimethylpentanoyl]-4-fluoro-2-pyrrolidinecarbonitrile hydrochloride A. 4-(4-Fluorophenyl)-2,2-dimethylbutanal To a flask containing 4-(4-fluorophenyl)-2,2-dimethylbutanenitrile (see: Org. Lett. 2000, 2, 3285; Knochel, P. et al. for preparation of this compound) (13.4 g, 70.2 mmol) in 300 mL of toluene cooled to −78° C. was added 70.2 mL of a 1.5 M toluene solution of DIBAL (105.3 mmol). After 2.5 hr a $H_2O$THF (250 mL/50 mL) solution containing 17.9 g of sodium acetate and 17.9 mL of acetic acid was gradually added. Upon complete addition celite and $Et_2O$ were added and the flask was allowed to warm to RT. After stirring for 1 hr the heterogeneous solution was filtered through a bed of celite. The celite was rinsed with $Et_2O$ and then the filtrate was washed with $H_2O$. After drying over $MgSO_4$ the solvent was removed in vacuo and the residual oil was purified via column chromatography (5% EtOAc/hexanes) yielding 11.3 g (58.2 mmol, 83% yield) of compound A.

$^1$H NMR (CDCl$_3$) 400 MHz δ 9.47 (s, 1H), 7.12–7.10 (m, 2H), 7.09–6.93 (m, 2H), 2.51–2.47 (m, 2H), 1.77–1.72 (m, 2H), 1.12 (s, 6H) ppm.

B. 5-(4-Fluorophenyl)-3,3-dimethyl-2-({(1R)-1-phenyl-2-[(trimethylsilyl)oxy]ethyl}amino)pentanenitrile To a $CH_2Cl_2$ solution (250 mL) containing compound A (9.07 g, 46.8 mmol) was added (R)-phenylglycinol (6.41 g, 46.8 mmol) at RT. The resulting solution stirred for 1.5 hr at which time it was cooled to 0° C. and trimethylsilyl cyanide (9.28 g, 93.5 mmol) was added. The yellow solution was slowly allowed to warm to RT overnight. It was then quenched with sat $NaHSO_4$ and the organic layer separated. The organics were washed with $H_2O$ dried ($MgSO_4$) and decolorized with charcoal. After filtering through celite the yellow oil was purified via column chromatography (hexanes/EtOAc (9:1)) yielding 11.9 g (28.9 mmol, 62% yield) of compound B as 6:1 mixture of diastereomers. Major diastereomer: $^1$H NMR (CDCl$_3$) 400 MHz δ 7.38–7.29 (m, 5H), 7.11–7.07 (m, 2H), 6.98–6.93 (m, 2H), 4.03 (dd, 1H, J=9.95, 3.8 Hz), 3.68 (m, 1H), 3.52 (t, 1H, J=10.2 Hz), 3.06 (d, 1H), J=13.4 Hz), 2.44–2.34 (m, 3H), 1.73–1.65 (m, 2H), 1.11 (s, 3H), 1.09 (s, 3H), 0.14 (s, 9H) ppm.

C. 5-(4-Fluorophenyl)-2-{[(1R)-2-hydroxy-1-phenylethyl]amino}-3,3-dimethylpentanenitrile.

To a MeOH solution (300 mL) containing compound B (11.85 g, 28.8 mmol) was added potassium fluoride (16.7 g, 287.6 mmol) at RT. The solution stirred for 1.5 hr at which time the bulk of the MeOH was removed in vacuo. $CH_2Cl_2$ and $H_2O$ were added and the organic layer separated. After drying over $MgSO_4$ the solvent was removed in vacuo and the resulting oil purified via column chromatography (hexanes/EtOAc (4:1)) yielding 8.86 g (26.1 mmol, 90% yield) of compound C as a 6:1 mixture of diastereomers. Major diastereomer: $^1$H NMR (CDCl$_3$) 400 MHz δ 7.38–7.30 (m, 5H), 7.10–7.06 (m, 2H), 6.97–6.92 (m, 2H), 4.06 (dd, 1H, J=9.5, 4.0 Hz), 3.79 (m, 1H), 3.58 (m, 1H), 3.07 (d, 1H, J=12.5 Hz), 2.43–2.30 (m, 3H), 1.95 (dd, 1H, J=7.8, 4.1 Hz), 1.74–1.64 (m, 2H), 1.11 (s, 3H), 1.09 (s, 3H) ppm.

D. 5-(4-Fluorophenyl)-3,3-dimethyl-2-[[(E)-phenylmethylidene]amino}pentanenitrile.

To a $CH_2Cl_2$ (10 mL)/MeOH (4 mL) solution containing compound C (494 mg, 1.45 mmol) cooled to 0° C. was added lead tetraacetate (838 mg, 1.89 mmol). The resulting solution stirred overnight at which time it had warmed to ambient temperature. To this solution was added 20 mL of a pH 7.2 phosphate buffer. After 30 min the cloudy solution was filtered through a bed of celite with the celite being rinsed thoroughly with $CH_2Cl_2$. The filtrate had $H_2O$ added to it and the organic layer was separated. The aqueous layer was extracted with $CH_2Cl_2$ and then the combined organic layers were dried ($MgSO_4$). The solvent was removed in vacuo and the oil purified via column chromatography (hexanes/EtOAc (9:1)) yielding 270 mg (0.88 mmol, 60% yield) of compound D.

$^1$H NMR (CDCl$_3$) 400 MHz δ 8.50 (d, 1H, J=1.4 Hz), 7.81–7.80 (d, 2H, J=6.6 Hz), 7.54–7.43 (m, 3H), 7.17–7.13 (m, 3H), 6.99–6.94 (m, 2H), 4.48 (s, 1H), 2.68–2.64 (m, 2H), 1.81–1.74 (m, 2H), 1.19 (s, 3H), 1.15 (s, 3H) ppm.

E. 5-(4-Fluorophenyl)-3,3-dimethylnorvailine hydrochloride.

To a flask containing compound D (268 mg, 0.87 mmol) was added 7 mL of concentrated HCl. The solution was heated to reflux for 18 hr at which time it was cooled and extracted with $Et_2O$. The aqueous layer had the solvent removed in vacuo and the residual oily solid was dissolved in $Et_2O$/MeOH and was decolorized with charcoal. After filtration and removal of the solvent in vacuo the residue was triterated with $Et_2O$ and the solvent removed in vacuo yielding 180 mg (0.65 mmol, 75% yield) of compound E as an oily solid which was taken on crude.

$^1$H NMR (d$_4$-MeOH) 400 MHz δ 7.25–7.20 (m, 2H), 7.01–6.95 (m, 2H), 4.45 (s(br), 1H), 2.67–2.63 (m, 2H), 1.76–1.72 (m, 2H), 1.22–1.13 (m, 6H).

F. N. Tert-butoxycarbonyl)-5-(4-fluorophenyl)-3,3-dimethylnorvaline.

To a dioxane solution (5 mL) containing compound E (180 mg, 0.65 mmol) was added 2.5 mL of a 2 M NaOH solution at RT. The resulting solution then had di-t-butyldicarbonate (284 mg, 1.34 mmol) added to it. After stirring overnight the solution was acidified with 1.0 M HCl. The organics were extracted with EtOAc (2x), dried ($MgSO_4$) and the solvent removed in vacuo. The residual oil was purified via column chroma-tography (5% MeOH/$CH_2Cl_2$) yielding 76 mg (0.22 mmol, 34% yield) of compound F.

$^1$H NMR (d$_4$-MeOH) 400 MHz δ 7.18–7.15 (m, 2H), 6.96–6.92 (m, 2H), 6.62 (d, 1H, J=9.3 Hz), 4.18 (d, 1H, J=9.5 Hz), 2.65–2.58 (m, 2H), 1.62–1.53 (m, 2H), 1.44 (s, 9H), 1.05 (s, 3H), 1.01 (s, 3H) ppm.

G. Tert-butyl (1S)-1-{[(2S,4S)-2-cyano-4-fluoropyrrolidinyl]carbonyl}-4-(4-fluorophenyl)-2,2-dimethylbutylcarbamate.

To a DMF solution (4 mL) containing compound F (172 mg, 0.51 mmol) was added diisopropylethyl amine (98 mg, 0.76 mmol) followed by HATU (213 mg, 0.56 mmol) at RT. After 15 min (2S,4S)-4-fluoro-2-pyrrolidinecarbonitrile 4-methylbenzenesulfonate (153 mg, 0.53 mmol) and diisopropylethyl amine (68 mg, 0.53 mmol) in 2 mL of DMF was added. The reaction stirred overnight at which time it was poured into EtOAc. The organics were washed with $H_2O$ (2x), sat. $NaHCO_3$ and sat. $NaHSO_4$. After drying over $MgSO_4$ the solvent was removed in vacuo and the residual yellow oil purified via column chromatography (2% MeOH/$CH_2Cl_2$) yielding 147 mg of compound G which underwent further purification via semi-prep HPLC yielding 80 mg of compound G.

$^1$H NMR (CDCl$_3$) 400 MHz δ 7.15–7.12 (m, 2H), 6.96–6.92 (m, 2H), 5.40 (d(br), 1H, J=52.0 Hz), 5.18 (d, 1H, J=9.7 Hz), 5.04 (d, 1H, J=9.3 Hz), 4.31 (d, 1H, J=9.9 Hz), 4.11 (s, 1H), 4.03 (m, 1H), 2.70–2.52 (m, 3H), 2.33 (m, 1H), 1.64–1.60 (m, 2H), 1.41 (s, 9H), 1.11 (s, 3H), 1.09 (s, 3H) ppm.

H. (2S,4S)-1-[(2S)-2-Amino-5-(4-fluorophenyl)-3,3-dimethylpentanoyl]-4-fluoro-2-pyrrolidinecarbonitrile hydrochloride.

To a CH$_2$CH$_2$ solution (4 mL) containing compound G (80 mg, 0.18 mmol) was added 71 µL of TFA (5 eq). After 30 min another 5 eq of TFA was added followed by an additional 10 eq after an hour. Upon stirring for a total of 3.5 hr the solvent was removed in vacuo and the residue dissolved in EtOAc. The organics were washed with sat. NaHCO$_3$, dried (MgSO$_4$) and the solvent removed in vacuo. The residual oil had 1.5 mL of dioxane added to it followed by 2.0 mL of a 4.0 M dioxane solution of HCl. The solvent was removed in vacuo and Et$_2$O added. The precipitated solid was collected via vacuum filtration yielding 40 mg (0.11 mmol, 60% yield) of compound H.

$^1$H NMR (d$_4$-MeOH) 400 MHz δ 7.25–7.22 (m, 2H), 7.00–6.95 (m, 2H), 5.46 (d(br), 1H, J=51.1 Hz), 5.09 (d, 1H, J=9.4 Hz), 4.12 (m, 1H), 4.03 (s, 1H), 3.90 (ddd, 1H, J=37.6, 12.7, 3.0 Hz), 2.68–2.44 (m, 4H), 1.78–1.73 (m, 2H), 1.21 (s, 6H) ppm.

Example 4

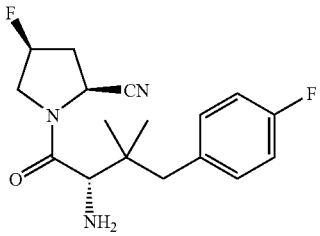

(2S,4R)-1-[(2S)-2-Amino-4-(4-fluorophenyl)-3,3-dimethylbutanoyl]-4-fluoropyrrrolidine-2-carbonitrile hydrochloride A. 3-(4-Fluorophenyl)-2,2-dimethylpropanenitrile.

To a toluene solution (60 mL) containing isobutyronitrile (5.0 g, 72.3 mmol) cooled to 0° C. was added 152 mL of a 0.5 M toluene solution of KHMDS (76.0 mmol). After 15 min 4-fluorobenzylbromide (14.4 g, 76.0 mmol) was added. The solution slowly warmed to ambient temperature overnight at which time it was quenched with H$_2$O. The organics were extracted with EtOAc and washed with sat. NaHSO$_4$. After drying over MgSO$_4$ the solvent was removed in vacuo and the residual yellow oil purified via column chromatography (5% EtOAc/hexanes) yielding 10.05 g (56.8 mmol, 79% yield) of compound A.

$^1$H NMR (CDCl$_3$) 400 MHz δ 7.25–7.22 (m, 2H), 7.05–7.00 (m, 2H), 2.78 (s, 2H), 1.34 (s, 6H) ppm.

B. 3-(4-Fluorophenyl)-2,2-dimethylpropanol.

To a toluene solution (100 mL) containing compound A (10.0 g, 56.5 mmol) cooled to –78° C. was added 56.5 mL of a 1.5 M toluene solution of DIBAL (84.7 mmol). After 2.5 hr a H$_2$O/THF solution (160 mL/40 mL) containing sodium acetate (14.3 g) and acetic acid (14.3 mL) was added followed by celite. The solution stirred for 1 hr and then Et$_2$O was added. The solution was filtered through celite with the celite being rinsed thoroughly with Et$_2$O. The filtrate was washed with H$_2$O (2×) and then with sat NaHCO$_3$. After drying over MgSO$_4$ the solvent was removed in vacuo and the residual oil purified via column chromatography (5% EtOAc/hexanes) yielding 9.23 g (51.3 mmol, 91% yield) of compound B.

$^1$H NMR (CDCl$_3$) 400 MHz δ 9.56 (s, 1H), 7.06–7.03 (m, 2H), 6.97–6.93 (m, 2H), 2.75 (s, 2H), 1.04 (s, 6H) ppm.

C. 2-Amino-4-(4-Fluorophenyl)-3,3-dimethylbutanenitrile.

To a MeOH solution (32 mL) containing compound B (5.0 g, 27.8 mmol) was added 3.8 mL of 30% NH$_4$OH, potassium cyanide (1.9 g, 29.2 mmol) and 15 mL of H$_2$O. To this solution was added ammonium chloride (1.64 g, 30.6 mmol) at RT. The resulting solution stirred overnight at which time it was heated to 70° C. After 5 hr the solution was cooled, diluted with EtOAc and then washed with H$_2$O (2×) followed by sat NaHCO$_3$. After drying over MgSO$_4$ the solvent was removed in vacuo and the remaining yellow oil purified via column chromatography (hexanes/EtOAc (1:1)) yielding 3.69 g (17.9 mmol, 64% yield) of compound C.

$^1$H NMR (CDCl$_3$) 400 MHz δ 7.17–7.13 (m, 2H), 7.00–6.95 (m, 2H), 3.33 (t, 1H, J=8.5 Hz), 2.80 (d, 1H, J=13.4 Hz), 2.61 (d, 1H, J=13.4 Hz), 1.58–1.57 (m, 2H), 1.03 (s, 3H), 1.02 (s, 3H) ppm.

D. 2-Amino-4-(4-Fluorophenyl)-3,3-dimethylbutanoic acid.

To a flask containing compound C (3.69 g, 17.9 mmol) was added 80 mL of concentrated HCl. The solution was then heated to reflux for 24 hr. The heterogeneous solution was then cooled in an ice bath and the white solid collected via vacuum filtration. After pumping on under high vacuum 4.06 g of a white powder was obtained. This material was taken on crude.

E. 2-[(Tert-butoxycarbonyl)amino]-4-(4-fluorophenyl)-3,3-dimethylbutanoic acid.

To a dioxane solution (20 mL) containing compound D (2.0 g, 7.66 mmol) was added 5 mL of H$_2$O and 9.6 mL of a 2.0 M aqueous solution of NaOH. To this solution was added di-t-butyl dicarbonate (2.34 g, 10.7 mmol) at RT. After stirring overnight the heterogeneous solution was poured into sat. NaHCO$_3$ and washed with Et$_2$O. The Et$_2$O layer was washed with sat. NaHCO$_3$ and then the combined aqueous layers were acidified with 1.0 M HCl and extracted with EtOAc (2×). After drying over MgSO$_4$ the solvent was removed in vacuo yielding 928 mg (2.86 mmol, 37% yield) of compound E.

$^1$H NMR (d$_4$-MeOH) 400 MHz δ 7.21–7.18 (m, 2H), 7.00–6.95 (m, 2H) 6.74 (d, 1H, J=9.0 Hz), 3.98 (d, 1H, J=9.0 Hz), 2.68 (d, 1H, J=13.4 Hz), 2.62 (d, 1H, J=13.3 Hz), 1.45 (s(br), 9H), 0.93 (s, 3H), 0.92 (s, 3H) ppm.

F. Tert-butyl (1S)-1-{[(2S,4S)-2-cyano-4-fluoropyrrolidin-1-yl]carbonyl}-3-(4-fluorophenyl)-2,2-dimethylpropylcarbamate.

To a DMF solution (20 mL) containing compound E (928 mg, 2.86 mmol) was added diisopropylethylamine (406 mg, 3.14 mmol) followed by HATU (1.14 g, 3.00 mmol) at RT. After 30 min (2S,4S)-4-fluoro-2-pyrrolidinecarbonitrile 4-methylbenzenesulfonate (857 mg, 3.00 mmol) and diisopropylethylamine (388 mg, 3.00 mmol) in 13 mL DMF was added. After stirring overnight the solution was poured into EtOAc and washed with H$_2$O (2×), sat NaHCO$_3$ and 1.0 M HCl. After drying over MgSO$_4$ the solvent was removed in vacuo. The residual oil was purified via column chromatography (hexanes/EtOAc/CH$_2$Cl$_2$ (5:4:1)) yielding 273 mg (0.65 mmol, low R$_f$ material) of the (S)-diastereromer as determined by vibrational circular dichroism and 226 mg of a mixture of the (R)-diastereomer plus an unknown impurity. The (S)-diastereomer was taken on.

$^1$H NMR (CDCl$_3$) 400 MHz δ 7.15–7.11 (m, 2H), 7.01–6.96 (m, 2H), 5.32 (dt, 1H, J=51.3, 3.3 Hz), 5.20 (d, 1H, J=9.7 Hz), 5.01 (d, 1H, J=9.3 Hz), 4.16 (d, 1H, J=10.1

Hz), 3.91 (m, 1H), 3.68 (dd, 1H, J=23.6, 12.1 Hz), 2.72–2.56 (m, 2H), 2.30 (m, 1H), 1.43 (s, 9H), 1.08 (s, 3H), 0.95 (s, 3H) ppm.

G. (2S,4R)-1-[(2S)-2-Amino-4-(4-fluorophenyl)-3,3-dimethylbutanoyl]-4-fluoropyrrrolidine-2-carbonitrile hydrochloride.

To a CH$_2$Cl$_2$ solution (7 mL) containing compound F (242 mg, 0.58 mmol) was added 443 µL (10 eq) of TFA at RT. After 30 min and additional 10 eq of TFA was added and after a total of 3 hr the reaction mixture was poured into sat. NaHCO$_3$. The organics were extracted with EtOAc, dried (MgSO$_4$) and the solvent removed in vacuo. The residual oil was dissolved in dioxane (4 mL) and then 4.0 mL of a 4.0 M HCl solution in dioxane was added. The solvent was removed in vacuo and the residue triturated with Et$_2$O. The resulting solid was collected via vacuum filtration affording 175 mg (0.46 mmol, 79% yield) of salt G.

$^1$H NMR (d$_4$-MeOH) 400 MHz δ 7.22–7.19 (m, 2H), 7.08–7.04 (m, 2H), 5.43 (d(br), 1H, J=51.1 Hz), 5.09 (d, 1H, J=9.5 Hz), 4.05 (s, 1H), 3.97–3.74 (m, 2H), 2.82 (d, 1H J=13.4 Hz), 2.72 (d, 1H, J=13.2 Hz), 2.64–2.39 (m, 2H), 1.07 (s, 3H), 1.00 (s, 3H) ppm.

B. (2S,4S)-1-{(2R)-2-Amino-3-[(4-methoxybenzyl)thio]-3-methylbutanoyl}-4-fluoropyrrolidine-2-carbonitrile hydrochloride To a CH$_2$Cl$_2$ (60 mL) solution containing trifluoroacetic acid (8 mL) was added compound A (1.2 g, 2.58 mmol, 1.0 eq). The resulting pale yellow solution was stirred at RT for 2 hr at which time the solvent was removed in vacuo. The resulting TFA salt was converted to the free base by addition of a sat. NaHCO$_3$ solution and extracting the aqueous layer (2×) with EtOAc. The combined organic extracts were dried over Na$_2$SO$_4$ and concentrated in vacuo. The resulting off-white foam was purified via flash chromatography using 5% MeOH (with 0.1% NH$_3$) in CH$_2$Cl$_2$ as the mobile phase affording 897 mg (2.45 mmol, 95% yield) of a white foam. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (D$_2$O) 400 MHz δ 7.31 (d, 2H, J=8.6 Hz), 6.88 (d, 2H, J=8.5 Hz), 5.49 (d, 1H, J=50.5 Hz), 5.00 (d, 1H, J=9.8 Hz), 4.02–3.52 (m, 8H), 2.65 (t, 1H, J=15.7 Hz), 2.40 (m, 1H), 1.44 (s, 3H), 1.31 (s, 3H) ppm.

Example 5

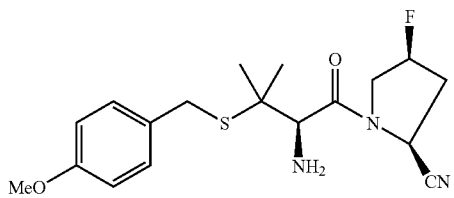

(2S,4S)-1-{(2R)-2-Amino-3-[(4-methoxybenzyl)thio]-3-methylbutanoyl}-4-fluoropyrrolidine-2-carbonitrile hydrochloride A. Tert-butyl (1R)-1-{[(2S,4S)-2-cyano-4-fluoropyrrolidin-1-yl]carbonyl}-2-[(4-methoxybenzyl)thio]-2-methylpropylcarbamate.

To a DMF solution (35 mL) containing (2R)-2-[(tert-butoxycarbonyl)amino]-3-[(4-methoxybenzyl)thio]-3-methylbutanoic acid (2.0 g, 5.41 mmol, 1.2 eq) was added N,N-diisopropylethylamine (1.06 mL 6.09 mmol, 1.35 eq) followed by HATU (2.9 g, 7.67 mmol, 1.7 eq). The resulting amber solution was stirred at RT for 20 min. To this stirring solution was added a solution of (2S, 4S)-4-fluoro-2-pyrrolidinecarbonitrile 4-methylbenzenesulfonate (1.29 g, 4.51 mmol, 1.0 eq) and N,N-diisopropylethylamine (864 µL, 4.96 mmol, 1.1 eq) in DMF (12 mL). The resulting solution was stirred at RT for 18 hr and was then quenched with a sat. NaHCO$_3$ solution (ca 50 mL). The cloudy solution was then poured into H$_2$O (ca 100 mL) and extracted with EtOAc (3×50 mL). The combined organic extracts were washed with H$_2$O (2×) and brine (1×); dried over MgSO$_4$ and concentrated in vacuo. The resulting amber oil was purified via flash chromatography using 1:1 hexanes/EtOAc as the mobile phase. Isolated 1.96 g (4.23 mmol, 78% yield) of compound A as a white foam.

$^1$H NMR (CDCl$_3$) 400 MHz δ 7.29 (d, 2H, J=8.8 Hz), 6.83 (d, 2H, J=8.6 Hz), 5.48 (d, 1H, J=51.4 Hz), 5.43 (d, 1H, J=9.2 Hz), 5.04 (d, 1H, J=9.3 Hz), 4.38 (d, 1H, J=8.9 Hz), 4.27 (m, 1H), 4.04 (m, 1H), 3.80 (s, 2H), 3.77 (s, 3H), 2.72 (t, 1H, 15.5 Hz), 2.37 (m, 1H), 1.47–1.41 (m, 14H) ppm.

Example 6

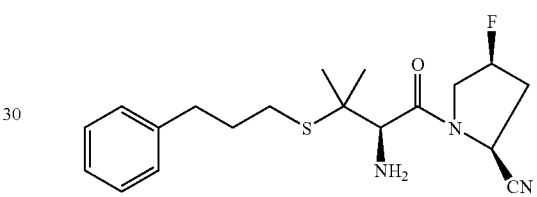

(2S,4S)-1-{(2R)-2-Amino-3-methyl-3-[(3-phenylpropyl)thio]butanoyl}-4-fluoropyrrolidine-2-carbonitrile hydrochloride A. Methyl (2R)-2-amino-3-mercapto-3-methylbutanoate To a methanol (18 mL, 1.14 M) solution containing L-penicillamine (3.0 g, 20.11 mmol, 1.0 eq) was added thionyl chloride (1.5 mL, 20.7 mmol, 1.03 eq). The resulting mixture was heated to reflux for 18 hr and the solvent removed in vacuo. The resulting clear semi-solid was used in the next step without further purification. Isolated 3.28 g (20.1 mmol, 100% yield).

B. Methyl (2R)-2-[(tert-butoxycarbonyl)amino]-3-mercapto-3-methylbutanoate

To a CH$_2$Cl$_2$ (60 mL) containing compound A (3.28 g, 20.1 mmol, 1.0 eq) was added di-tert-butyldicarbonate (4.48 g, 20.5 mmol, 1.02 eq) and triethylamine (7.0 mL, 50.3 mmol, 2.5 eq). The resulting mixture was allowed to stir at RT for 18 hr. The solvent was removed in vacuo and the residue taken up it Et$_2$O. The insoluble white solid was filtered and the filtrate washed with brine, dried over MgSO$_4$, and concentrated in vacuo. Resulting white solid was used in next step without further purification. Isolated 5.01 g (19.02 mmol, 95% yield).

$^1$H NMR (d$_4$-MeOH) 400 MHz δ 4.26 (m, 1H), 3.72 (s, 3H), 1.44–1.42 (m, 15H) ppm.

C. Methyl (2R)-2-[(tert-butoxycarbonyl)amino]-3-methyl-3-[(3-phenylpropyl)thio]butanoate To a CH$_3$CN (20 mL) solution containing compound B (346 mg, 1.31 mmol, 1.0 eq) was added sodium tert-butoxide (138 mg, 1.44 mmol, 1.1 eq). The resulting pale yellow mixture was allowed to stir at RT for 10 min at which time 1-bromo-3-phenylpropane (219 μL, 1.44 mmol, 1.1 eq) was added. The resulting solution was allowed to stir at RT for 18 hr. The reaction was then quenched with a sat NH$_4$Cl solution, poured into H$_2$O, and extracted (2×) with EtOAc. The combined extracts were dried over MgSO$_4$ and concentrated in vacuo. Purified via flash chromatography using 2:1 Hexane/EtOAc as the mobile phase. Isolated 376 mg (0.988 mmol, 76% yield).

$^1$H NMR (CDCl$_3$) 400 MHz δ 7.30–7.16 (m, 5H), 5.38 (d, 1H J=8.8 Hz), 4.29 (d, 1H, J=9.0 Hz), 3.71 (s, 3H), 2.72 (t, 2H, J=7.4 Hz), 2.58–2.51 (m, 2H), 1.89–1.82 (m, 2H), 1.44 (s, 9H), 1.36 (d, 6H, J=8.8 Hz) ppm.

D. (2R)-2-[(tert-Butoxycarbonyl)amino]-3-methyl-3-[(3-phenylpropyl)thio]butanoic acid.

To a dioxane (7.5 mL)/H$_2$O (2.5 mL) solution containing compound C (376 mg, 0.988 mmol, 1.0 eq) was added lithium hydroxide monohydrate (207 mg, 4.94 mmol, 5.0 eq). The resulting heterogeneous mixture was allowed to stir at RT for 18 hr. The reaction was then quenched with a sat NH$_4$Cl solution, poured into H$_2$O, and extracted (2×) with EtOAc. The combined extracts were dried over MgSO$_4$ and concentrated in vacuo. Purified via flash chromatography using 1:1 hexanes/EtOAc (with 0.1% AcOH) as the mobile phase. Isolated 230 mg (0.626 mmol, 64% yield).

$^1$H NMR (CDCl$_3$) 400 MHz δ 7.31–7.16 (m, 5H), 5.51 (d, 1H, J=9.5 Hz), 4.33 (d, 1H, J=9.5 Hz), 3.41 (t, 2H, J=6.8 Hz), 2.79 (t, 2H, J=7.3 Hz), 2.20–2.13 (m, 2H), 1.47–1.44 (m, 15H) ppm.

E. Tert-butyl (1R)-1-{[(2S,4S)-2-cyano-4-fluoropyrrolidin-1-yl]carbonyl}-2-methyl-2-[(3-phenylpropyl)thio]propylcarbamate.

To a DMF solution (5 mL) containing compound D (230 mg, 0.626 mmol, 1.2 eq) was added N,N-diisopropylethylamine (123 μL, 0.705 mmol, 1.35 eq) followed by HATU (337 mg, 0.887 mmol, 1.7 eq). The resulting amber solution was stirred at RT for 20 min. To this stirring solution was added a solution of (2S, 4S)-4-fluoro-2-pyrrolidinecarbonitrile 4-methylbenzenesulfonate (149 mg, 0.522 mmol, 1.0 eq) and N,N-diisopropylethylamine (100 μL, 0.574 mmol, 1.1 eq) in DMF (2 mL). The resulting solution was stirred at RT for 18 hr and quenched with a sat. NaHCO$_3$ solution (ca 5 mL). The cloudy solution was then poured into H$_2$O (ca 20 mL) and extracted with EtOAc (3×10 mL). The combined organic extracts were washed with H$_2$O (2×) and brine (1×); dried over MgSO$_4$ and concentrated in vacuo. The resulting amber oil was purified via flash chromatography using 1:1 hexanes/EtOAc as the mobile phase. Isolated 190 mg (0.411 mmol, 79% yield) of compound E as a white foam.

$^1$H NMR (CDCl$_3$) 400 MHz δ 7.28–7.17 (m, 5H), 5.46 (d, 1H, J=51.4 Hz), 5.37 (d, 1H, J=9.0 Hz), 5.00 (d, 1H, J=9.3 Hz), 4.38–4.29 (m, 2H), 4.01 (m, 1H), 2.77–2.58 (m, 5H), 2.35 (m, 1H), 1.92–1.80 (m, 2H), 1.44–1.34 (m, 15H) ppm.

F. (2S,4S)-1-{(2R)-2-Amino-3-methyl-3-[(3-phenylpropyl)thio]butanoyl}-4-fluoropyrrolidine-2-carbonitrile To a CH$_2$Cl$_2$ (10 mL) solution containing trifluoroacetic acid (1 mL) was added compound E (190 mg, 0.411 mmol, 1.0 eq). The resulting pale yellow solution was stirred at RT for 2 hours at which time the solvent was removed in vacuo. The resulting TFA salt was converted to the free base by addition of a sat. NaHCO$_3$ solution and extracting the aqueous layer (2×) with EtOAc. The combined organic extracts were dried over Na$_2$SO$_4$ and concentrated in vacuo. The resulting off-white foam was purified via flash chromatography using 5% MeOH (with 0.1% NH$_3$) in CH$_2$Cl$_2$ as the mobile phase affording 134 mg (0.389 mmol, 94% yield) of a white foam. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (D$_2$O) 400 MHz δ 7.23–7.11 (m, 5H), 5.46 (d, 1H, J=50.4 Hz), 4.98 (d, 1H, J=9.1 Hz), 4.04–3.96 (m, 2H), 3.68 (m, 1H), 2.62–2.30 (m, 6H), 1.78–1.71 (m, 2H), 1.29 (d, 6H, J=9.7 Hz) ppm.

Example 7

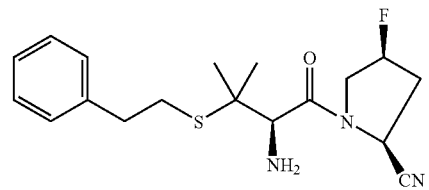

(2S,4S)-1-{(2R)-2-Amino-3-methyl-3-[(2-phenylethyl)thio]butanoyl}-4-fluoropyrrolidine-2-carbonitrile hydrochloride A. Methyl (2R)-2-[(tert-butoxycarbonyl)amino]-3-methyl-3-[(2-phenylethyl)thio]butanoate.

To a CH$_3$CN (50 mL) solution containing methyl (2R)-2-[(tert-butoxycarbonyl)amino]-3-mercapto-3-methylbutanoate (as described above) (1.26 g, 4.78 mmol, 1.0 eq) was added sodium tert-butoxide (597 mg, 6.21 mmol, 1.3 eq). The resulting pale yellow mixture was allowed to stir at RT for 10 min at which time (2-bromoethyl)benzene (718 μL, 5.26 mmol, 1.1 eq) was added. The resulting solution was allowed to stir at RT for 18 hr. The reaction was then quenched with a sat NH$_4$Cl solution, poured into H$_2$O, and extracted (2×) with EtOAc. Combined extracts were dried over MgSO$_4$ and concentrated in vacuo. Purified via flash chromatography using 5:1 hexanes/EtOAc as the mobile phase. Isolated 761 mg (2.07 mmol, 45% yield).

$^1$H NMR (CDCl$_3$) 400 MHz δ 7.31–7.19 (m, 5H), 5.36 (d, 1H, J=9.0 Hz), 4.33 (d, 1H, J=9.1 Hz), 3.71 (s, 3H), 2.83–2.78 (m, 4H), 1.44 (s, 9H), 1.36 (d, 6H, J=7.5 Hz) ppm.

B. (2R)-2-[(Tert-butoxycarbonyl)amino]-3-methyl-3-[(2-phenylethyl)thio]butanoic acid.

To a dioxane (20 mL)/H$_2$O (7 mL) solution containing compound A (761 mg, 2.07 mmol, 1.0 eq) was added lithium hydroxide monohydrate (434 mg, 10.35 mmol, 5.0 eq). The resulting heterogeneous mixture was allowed to stir at RT for 18 hr. The reaction was then quenched with a sat NH$_4$Cl solution, poured into H$_2$O, and extracted (2×) with EtOAc. The combined extracts were dried over MgSO$_4$ and concentrated in vacuo. Purified via flash chromatography using 1:1 hexanes/EtOac (with 0.1% AcOH) as the mobile phase. Isolated 502 mg (1.42 mmol, 69% yield).

$^1$H NMR (CDCl$_3$) 400 MHz δ 7.31–7.18 (m, 5H), 5.42 (d, 1H, J=8.3 Hz), 4.32 (s(br), 1H), 2.87–2.81 (m, 4H), 1.44 (s, 9H), 1.40 (s, 3H), 1.36 (s, 3H) ppm.

C. Tert-butyl (1R)-1-{[(2S,4S)-2-cyano-4-fluoropyrrolidin-1-yl]carbonyl}-2-methyl-2-[(2-phenylethyl)thio]propylcarbamate.

To a DMF solution (10 mL) containing compound B (502 mg, 1.42 mmol, 1.2 eq) was added N,N-diisopropylethylamine (278 µL, 1.59 mmol, 1.35 eq) followed by HATU (764 mg, 2.01 mmol, 1.7 eq). The resulting amber solution was stirred at RT for 20 min. To this stirring solution was added a solution of (2S, 4S)-4-fluoro-2-pyrrolidinecarbonitrile 4-methylbenzenesulfonate (338 mg, 1.18 mmol, 1.0 eq) and N,N-diisopropylethylamine (226 µL, 1.3 mmol, 1.1 eq) in DMF (5 mL). The resulting solution was stirred at RT for 18 h and quenched with a sat NaHCO$_3$ solution (ca 5 mL). The cloudy solution was then poured into H$_2$O (ca 20 mL) and extracted with EtOAc (3×10 mL). The combined organic extracts were washed with H$_2$O (2×) and brine (1×); dried over MgSO$_4$ and concentrated in vacuo. The resulting amber oil was purified via flash chromatography using 1:1 hexanes/EtOAc as the mobile phase. Isolated 361 mg (0.803 mmol, 80% yield) of compound C as a white foam.

$^1$H NMR (CDCl$_3$) 400 MHz δ 7.30–7.20 (m, 5H), 5.46 (d, 1H, J=51.0 Hz), 5.38 (d, 1H, J=9.2 Hz), 5.01 (d, 1H, J=9.4 Hz), 4.36–4.25 (m, 2H), 4.06 (m, 1H), 2.87–2.84 (m, 4H), 2.70 (t, 1H, J=15.0 Hz), 2.35 (m, 1H), 1.41–1.37 (m, 15H) ppm.

D. (2S,4S)-1-{(2R)-2-Amino-3-methyl-3-[(2-phenylethyl)thio]butanoyl}-4-fluoropyrrolidine-2-carbonitrile.

To a CH$_2$Cl$_2$ (20 mL) solution containing trifluoroacetic acid (2 mL) was added compound C (361 mg, 0.803 mmol, 1.0 eq). The resulting pale yellow solution was stirred at RT for 2 h at which time the solvent was removed in vacuo. The resulting TFA salt was converted to the free base by addition of a sat. NaHCO$_3$ solution and extracting the aqueous layer (2×) with EtOAc. The combined organic extracts were dried over Na$_2$SO$_4$ and concentrated in vacuo. The resulting off-white foam was purified via flash chromatography using 5% MeOH (with 0.1% NH$_3$) in CH$_2$Cl$_2$ as the mobile phase affording 223 mg (0.638 mmol, 80% yield) of a white foam. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (D$_2$O) 400 MHz δ 7.20–7.09 (m, 5H), 5.43 (d, 1H, J=50.5 Hz), 4.94 (d, 1H, J=9.5 Hz), 4.13 (m, 1H), 3.89 (s, 1H), 3.71 (m, 1H), 2.84–2.70 (m, 4H), 2.59 (t, 1H J=15.7 Hz), 2.37 (m, 1H), 1.28 (s, 3H), 1.22 (s, 3H) ppm.

Example 8

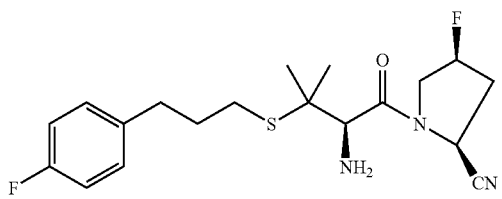

(2S,4S)-1-((2R)-2-Amino-3-{[3-(4-fluorophenyl)propyl]thio}-3-methylbutanoyl)-4-fluoropyrrolidine-2-carbonitrile hydrochloride A. 3-(4-Fluorophenyl)propan-1-ol.

To a THF (200 mL) solution containing 3-(4-fluorophenyl)propanoic acid (33.6 g, 0.2 mol) was added a 1.0 M solution of LiAlH4 in Et$_2$O (200 mL, 0.2 mol) over a period of 0.5 h. The resulting mixture was allowed to stir at RT for 18 h. The reaction was slowly quenched with H$_2$O and the aqueous layer extracted (1×) with Et$_2$O. The combined organic extracts were dried over MgSO$_4$ and concentrated in vacuo. The resulting oil was used in the next step without further purification. Isolated 31.4 g (0.2 mol, 100% yield).

B. 1-(3-Chloropropyl)-4-fluorobenzene.

To a CH$_2$Cl$_2$ (300 mL) solution containing compound A (31.4 g, 0.2 mol) was added dichlorotriphenylphosphorane (110 g, 0.33 mol). The resulting mixture was stirred at RT for 20 min and then concentrated in vacuo. Hexanes (ca 200 mL) was added to the residue and the resulting heterogeneous mixture was stirred at RT for 30 min. The insoluble solids were filtered and washed with hexanes. The filtrate was concentrated in vacuo and the resulting oil was used in the next step without further purification. Isolated 33.3 g (0.193 mol, 96% yield).

C. Methyl (2R)-2-[(tert-butoxycarbonyl)amino]-3-{[3-(4-fluorophenyl)propyl]thio}-3-methylbutanoate.

To a CH$_3$CN (60 mL) solution containing methyl (2R)-2-[(tert-butoxycarbonyl)amino]-3-mercapto-3-methylbutanoate (as described above) (1.51 g, 5.73 mmol, 1.0 eq) was added sodium tert-butoxide (716 mg, 7.45 mmol, 1.3 eq). The resulting pale yellow mixture was allowed to stir at RT for 10 min at which time 1-(3-chloropropyl)-4-fluorobenzene (as described above) (1.09 g, 6.3 mmol, 1.1 eq) was added. The resulting solution was allowed to stir at RT for 18 hr. The reaction was then quenched with a sat NH$_4$Cl solution, poured into H$_2$O, and extracted (2×) with EtOAc. The combined extracts were dried over MgSO$_4$ and concentrated in vacuo and then purified via flash chromatography using 5:1 hexanes/EtOAc as the mobile phase. Isolated 700 mg (1.75 mmol, 31% yield).

$^1$H NMR (CDCl$_3$) 400 MHz δ 7.14–7.10 (m, 2H), 6.98–6.93 (m, 2H), 5.36 (d, 1H, J=9.1 Hz), 4.29 (d, 1H, J=9.2 Hz), 3.71 (s, 3H), 2.68 (t, 2H, J=7.4 Hz), 2.56–2.49 (m, 2H), 1.86–1.79 (m, 2H), 1.43 (s, 9H), 1.35 (d, 6H, J=6.8 Hz) ppm.

D. (2R)-2-[(Tert-butoxycarbonyl)amino]-3-{[3-(4-fluorophenyl)propyl]thio}-3-methylbutanoic acid.

To a dioxane (20 mL)/H$_2$O (7 mL) solution containing compound A (700 mg, 1.75 mmol, 1.0 eq) was added lithium hydroxide monohydrate (367 mg, 8.75 mmol, 5.0 eq). The resulting heterogeneous mixture was allowed to stir at RT for 18 hr. The reaction was then quenched with a sat NH$_4$Cl solution, poured into H$_2$O, and extracted (2×) with EtOAc. The combined extracts were dried over MgSO$_4$ and concentrated in vacuo. Purified via flash chromatography using 1:1 hexanes/EtOAc (with 0.1% AcOH) as the mobile phase. Isolated 512 mg (1.33 mmol, 76% yield).

$^1$H NMR (CDCl$_3$) 400 MHz δ 7.13–7.10 (m, 2H), 6.99–6.93 (m, 2H), 5.41 (d, 1H, J=8.1 Hz), 4.29 (s(br), 1H), 2.68–2.55 (m, 4H), 1.88–1.80 (m, 2H), 1.43 (s, 9H), 1.39 (s, 3H), 1.36 (s, 3H) ppm.

E. Tert-butyl (1R)-1-{[(2S,4S)-2-cyano-4-fluoropyrrolidin-1-yl]carbonyl}-2-{[3-(4-fluorophenyl)propyl]thio}-2-methylpropylcarbamate To a DMF solution (15 mL) containing compound B (512 mg, 1.33 mmol, 1.2 eq) was added N,N-diisopropylethylamine (261 µL, 1.5 mmol, 1.35 eq) followed by HATU (717 mg, 1.89 mmol, 1.7 eq). The resulting amber solution was stirred at RT for 20 min. To this stirring solution was added a solution of (2S, 4S)-4-fluoro-2-pyrrolidinecarbonitrile 4-methylbenzenesulfonate (317 mg, 1.11 mmol, 1.0 eq) and N,N-diisopropylethylamine (213 μL, 1.22 mmol, 1.1 eq) in DMF (10 mL). The resulting solution was stirred at RT for 18 hr and quenched with a sat NaHCO₃ solution (ca 5 mL). The cloudy solution was then poured into H₂O (ca 20 mL) and extracted with EtOAc (3×10 mL). The combined organic extracts were washed with H₂O (2×) and brine (1×); dried over MgSO₄ and concentrated in vacuo. The resulting amber oil was purified via flash chromatography using 1:1 Hexane/EtOAc as the mobile phase. Isolated 420 mg (0.872 mmol, 79% yield) of compound C as a white foam.

¹H NMR (CDCl₃) 400 MHz δ 7.14–7.11 (m, 2H), 6.97–6.92 (m, 2H), 5.47 (d, 1H, J=50.9 Hz), 5.36 (d, 1H, J=8.4 Hz), 5.00 (d, 1H, J=9.3 Hz), 4.42–4.32 (m, 2H), 4.01 (m, 1H), 2.74–2.57 (m, 5H), 2.36 (m, 1H), 1.89–1.76 (m, 2H), 1.41–1.37 (m, 15H) ppm.

F. (2S,4S)-1-((2R)-2-Amino-3-{[3-(4-fluorophenyl)propyl]thio}-3-methylbutanoyl)-4-fluoropyrrolidine-2-carbonitrile.

To a CH₂Cl₂ (30 mL) solution containing trifluoroacetic acid (3 mL) was added compound C (420 mg, 0.872 mmol, 1.0 eq). The resulting pale yellow solution was stirred at RT for 2 hr at which time the solvent was removed in vacuo. The resulting TFA salt was converted to the free base by addition of a sat. NaHCO₃ solution and extracting the aqueous layer (2×) with EtOAc. The combined organic extracts were dried over Na₂SO₄ and concentrated in vacuo. The resulting off-white foam was purified via flash chromatography using 5% MeOH (with 0.1% NH₃) in CH₂Cl₂ as the mobile phase affording 275 mg (0.721 mmol, 83% yield) of a white foam. To form the HCl salt, the free base was taken up in Et₂O and acetone added until all solids were in solution. 2.0 M HCl in ether was added dropwise until no more precipitate formed. The precipitate was then filtered and washed several times with Et₂O. The resulting salt was dried under high vacuum.

¹H NMR (D₂O) 400 MHz δ 7.15–7.10 (m, 2H), 6.96–6.90 (m, 2H), 5.48 (d, 1H, J=50.9 Hz), 4.99 (d, 1H, J=9.6 Hz), 4.07–3.98 (m, 2H), 3.74 (m, 1H), 2.64–2.32 (m, 6H), 1.80–1.68 (m, 2H), 1.30 (d, 6H, J=6.6 Hz) ppm.

Example 9

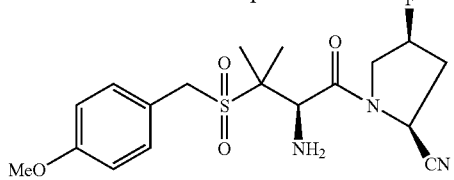

(2S,4S)-1-{(2R)-2-Amino-3-[(4-methoxybenzyl)sulfonyl]-3-methylbutanoyl}-4-fluoropyrrolidine-2-carbonitrile hydrochloride A. Tert-butyl (1R)-1-{[(2S,4S)-2-cyano-4-fluoropyrrolidin-1-yl]carbonyl}-2-[(4-methoxybenzyl)sulfonyl]-2-methylpropylcarbamate.

To a CHCl₃ (25 mL) solution containing tert-butyl (1R)-1-{[(2S,4S)-2-cyano-4-fluoropyrrolidin-1-yl]carbonyl}-2-[(4-methoxybenzyl)thio]-2-methylpropylcarbamate (as described above) (473 mg, 1.017 mmol, 1.0 eq) was added 3-chloroperoxybenzoic acid (1.76 g, 10.18 mmol, 10 eq). The resulting mixture was stirred at RT for 18 hr. The reaction was quenched with 1.0 N NaOH (ca 5 mL) and the layers separated. The organic layer was dried over MgSO₄ and concentrated in vacuo. The resulting white fluffy solid was used in the next step without further purification. Isolated 400 mg (0.805 mmol, 80% yield).

¹H NMR (CDCl₃) 400 MHz δ 7.35 (d, 2H, J=8.8 Hz), 6.92 (d, 2H, J=8.8 Hz), 5.48 (d, 1H, J=51.0 Hz), 5.04 (d, 1H, J=9.1 Hz), 4.99 (d, 1H, J=9.4 Hz), 4.34–3.98 (m, 4H), 3.81 (s, 3H), 2.73 (t, 1H, J=15.0 Hz), 2.39 (m, 1H), 1.58 (s, 3H), 1.53 (s, 3H), 1.42 (s, 9H) ppm.

B. (2S,4S)-1-{(2R)-2-Amino-3-[(4-methoxybenzyl)sulfonyl]-3-methylbutanoyl}-4-fluoropyrrolidine-2-carbonitrile.

To a CH₂Cl₂ (40 mL) solution containing trifluoroacetic acid (4 mL) was added compound A (400 mg, 0.805 mmol, 1.0 eq). The resulting pale yellow solution was stirred at RT for 2 hr at which time the solvent was removed in vacuo. The resulting TFA salt was converted to the free base by addition of a sat NaHCO₃ solution and extracting the aqueous layer (2×) with EtOAc. The combined organic extracts were dried over Na₂SO₄ and concentrated in vacuo. The resulting off-white foam was purified via flash chromatography using 5% MeOH (with 0.1% NH₃) in CH₂Cl₂ as the mobile phase affording 296 mg (0.745 mmol, 93% yield) of a white foam. To form the HCl salt, the free base was taken up in Et₂O and acetone added until all solids were in solution. 2.0 M HCl in ether was added dropwise until no more precipitate formed. The precipitate was then filtered and washed several times with Et₂O. The resulting salt was dried under high vacuum.

¹H NMR (D₂O) 400 MHz δ 7.28 (d, 2H, J=8.8 Hz), 6.92 (d, 2H, J=8.8 Hz), 5.47 (d, 1H J=50.6 Hz), 5.00 (d, 1H, J=10.0 Hz), 4.66 (s, 1H), 4.51 (s, 2H), 4.05 (m, 1H), 3.81 (m, 1H), 3.69 (s, 3H), 2.64 (t, 1H, J=15.7 Hz), 2.42 (m, 1H), 1.62 (s, 3H), 1.48 (s, 3H) ppm.

Example 10

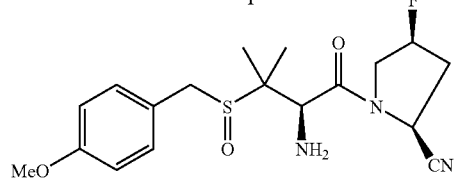

(2S,4S)-1-{(2R)-2-Amino-3-[(4-methoxybenzyl)sulfinyl]-3-methylbutanoyl}-4-fluoropyrrolidine-2-carbonitrile hydrochloride A. Tert-butyl (1R)-1-{[(2S,4S)-2-cyano-4-fluoropyrrolidin-1-yl]carbonyl}-2-[(4-methoxybenzyl)sulfinyl]-2-methylpropylcarbamate To a methanol (10 mL) solution containing tert-butyl (1R)-1-{[(2S,4S)-2-cyano-4-fluoropyrrolidin-1-yl]carbonyl}-2-[(4-methoxybenzyl)thio]-2-methyl propylcarbamate (as described above) (660 mg, 1.42 mmol, 1.0 eq) was added a solution of NaIO₄ (334 mg, 1.56 mmol, 1.1 eq) in H₂O (10 mL). The resulting mixture was stirred at RT for 18 hr. The resulting heterogeneous mixture was partitioned between CH₂Cl₂ and H₂O. The organic layer was dried over MgSO₄ and concentrated in vacuo. Resulting white fluffy solid was used in the next step without further purification. Isolated 600 mg (1.25 mmol, 87% yield) as a mixture of diastereomers.

¹H NMR (CDCl₃) 400 MHz δ 7.27–7.25 (m, 2H), 6.90–6.88 (m, 2H), 5.87 (s(br), 1H), 5.40 (m, 1H), 5.03–4.95 (m, 2H), 4.19–3.66 (m, 7H), 2.65 (m, 1H), 2.36 (m, 1H), 1.49–1.38 (m, 15H) ppm.

B. (2S,4S)-1-{(2R)-2-Amino-3-[(4-methoxybenzyl)sulfinyl]-3-methylbutanoyl}-4-fluoropyrrolidine-2-carbonitrile.

To a CH₂Cl₂ (50 mL) solution containing trifluoroacetic acid (5 mL) was added compound A (600 mg, 1.25 mmol, 1.0 eq). The resulting pale yellow solution was stirred at RT for 2 hr at which time the solvent was removed in vacuo. The resulting TFA salt was converted to the free base by addition of a sat. NaHCO$_3$ solution and extracting the aqueous layer (2×) with EtOAc. The combined organic extracts were dried over Na$_2$SO$_4$ and concentrated in vacuo. The resulting off-white foam was purified via flash chromatography using 5% MeOH (with 0.1% NH$_3$) in CH$_2$Cl$_2$ as the mobile phase affording 368 mg (0.965 mmol, 77% yield) of a white foam. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (D$_2$O) 400 MHz δ 7.25–7.21 (m, 2H), 6.93–6.90 m, 2H), 5.42 (m, 1H), 5.02 (m, 1H), 4.48 (m, 1H), 4.24–3.70 (m, 7H), 2.68–2.31 (m, 2H), 1.52–1.32 (m, 6H) ppm.

Example 11

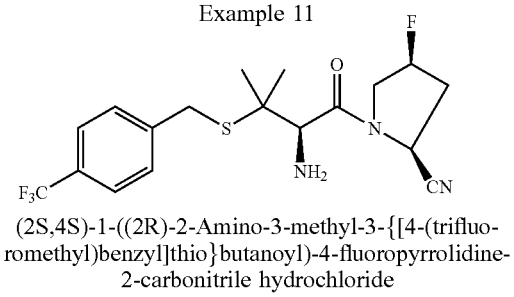

(2S,4S)-1-((2R)-2-Amino-3-methyl-3-{[4-(trifluoromethyl)benzyl]thio}butanoyl)-4-fluoropyrrolidine-2-carbonitrile hydrochloride A. (2R)-2-[Tert-butoxycarbonyl)amino]-3-mercapto-3-methylbutanoic acid.

To a THF (300 mL) solution containing L-penicillamine (5.0 g, 33.51 mmol, 1.0 eq) was added potassium hydroxide (1.88 g, 33.51 mmol, 1.0 eq). The mixture was then cooled to 0° C. and di-tert-butyldicarbonate (7.31 g, 33.51 mmol, 1.0 eq) was added. The resulting stirred mixture was allowed to warm to RT overnight. The reaction was then poured into H$_2$O (ca 300 mL) and extracted (2×) with EtOAc. The combined organic extracts were dried over MgSO$_4$ and concentrated in vacuo. The resulting white solid was used in the next step without further purification. Isolated 7.68 g (30.80 mmol, 92% yield).

$^1$H NMR (CDCl$_3$) 400 MHz δ 5.51 (d, 1H, J=9.6 Hz), 4.33 (d, 1H, J=9.6 Hz), 1.55 (s, 3H), 1.45 (s, 9H), 1.41 (s, 3H) ppm.

B. (2R)-2-[(Tert-butoxycarbonyl)amino]-3-methyl-3-{[4-(trifluoromethyl)benzyl]thio}butanoic acid.

To a CH$_3$CN (40 mL) solution containing compound A (1.0 g, 4.011 mmol, 1.0 eq) was added sodium tert-butoxide (810 mg, 8.42 mmol, 2.1 eq). The resulting pale yellow solution was allowed to stir for 10 min at which time 4-(trifluoromethyl)benzylbromide (1.05 g, 4.41 mmol, 1.1 eq). The resulting mixture was heated to 50° C. and allowed to stir for 18 hr. The reaction was then poured into H$_2$O (ca 50 mL) and extracted (2×) with EtOAc. The combined extracts were dried over MgSO$_4$ and concentrated in vacuo. The resulting solid was used in the next step without further purification. Isolated 1.45 g (3.55 mmol, 89% yield).

$^1$H NMR (CDCl$_3$) 400 MHz δ 7.55 (d, 2H, J=8.1 Hz), 7.44 (d, 2H, J=8.1 Hz), 5.39 (s(br), 1H), 4.44 (s(br), 1H), 3.85 (s, 2H), 1.45–1.43 (m, 15H) ppm.

C. Tert-butyl (1R)-1-{[(2S,4S)-2-cyano-4-fluoropyrrolidin-1-yl]carbonyl}-2-methyl-2-{[4-(trifluoromethyl)benzyl]thio}propylcarbamate.

To a DMF solution (30 mL) containing compound B (1.45 mg, 3.55 mmol, 1.2 eq) was added N,N-diisopropylethylamine (698 μL, 4.01 mmol, 1.35 eq) followed by HATU (1.92 g, 5.05 mmol, 1.7 eq). The resulting amber solution was stirred at RT for 20 min. To this stirring solution was added a solution of (2S, 4S)-4-fluoro-2-pyrrolidinecarbonitrile 4-methylbenzenesulfonate (849 mg, 2.97 mmol, 1.0 eq) and N,N-diisopropylethylamine (569 μL, 3.27 mmol, 1.1 eq) in DMF (25 mL). The resulting solution was stirred at RT for 18 hr and then quenched with a sat. NaHCO$_3$ solution (ca 5 mL). The cloudy solution was then poured into H$_2$O (ca 20 mL) and extracted with EtOAc (3×10 mL). The combined organic extracts were washed with H$_2$O (2×) and brine (1×); dried over MgSO$_4$ and concentrated in vacuo. The resulting amber oil was purified via flash chromatography using 1:1 hexanes/EtOAc as the mobile phase. Isolated 682 mg (1.35 mmol, 45% yield) of compound C as a white foam.

$^1$H NMR (CDCl$_3$) 400 MHz δ 7.55 (d, 2H, J=8.1 Hz), 7.50 (d, 2H, J=8.8 Hz), 5.49 (d, 1H, J=50.8 Hz), 5.42 (d, 1H, J=9.9 Hz), 5.03 (d, 1H, J=10.0 Hz), 4.40 (d, 1H, J=9.5 Hz), 4.32 (m, 1H), 4.04 (m, 1H), 3.88 (s, 2H), 2.74 (t, 1H, J=15.1 Hz), 2.38 (m, 1H), 1.47 (s, 3H), 1.42 (s, 9H), 1.41 (s, 3H) ppm.

D. (2S,4S)-1-((2R)-2-Amino-3-methyl-3-{[4-(trifluoromethyl)benzyl]thio}butanoyl)-4-fluoropyrrolidine-2-carbonitrile.

To a CH$_2$Cl$_2$ (70 mL) solution containing trifluoroacetic acid (7 mL) was added compound A (682 mg, 1.35 mmol, 1.0 eq). The resulting pale yellow solution was stirred at RT for 2 hr at which time the solvent was removed in vacuo. The resulting TFA salt was converted to the free base by addition of a sat. NaHCO$_3$ solution and extracting the aqueous layer (2×) with EtOAc. The combined organic extracts were dried over Na$_2$SO$_4$ and concentrated in vacuo. The resulting off-white foam was purified via flash chromatography using 5% MeOH (with 0.1% NH$_3$) in CH$_2$Cl$_2$ as the mobile phase affording 390 mg (0.967 mmol, 72% yield) of a white foam. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (D$_2$O) 400 MHz δ 7.57 (d, 2H, J=8.1 Hz), 7.49 (d, 2H, J=8.5 Hz), 5.46 (d, 1H, J=51.4 Hz), 4.98 (d, 1H, J=9.5 Hz), 4.05–3.53 (m, 5H), 2.62–2.28 (m, 2H), 1.40 (s, 3H), 1.31 (s, 3H) ppm.

Example 12

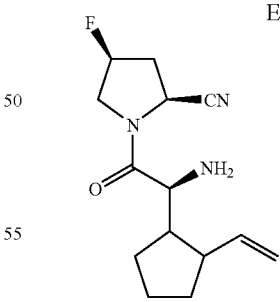

(2S,4S)-1-[(2S)-2-Amino-2-(1-vinylcyclopentyl)ethanoyl]-4-fluoropyrrolidine-2-carbonitrile hydrochloride A. Tert-butyl (1S)-2-[(2S,4S)-2-cyano-4-fluoropyrrolidin-1-yl]-2-oxo-1-(1-vinylcyclopentyl)ethylcarbamate.

To a DMF solution (25 mL) containing racemic [(tert-butoxycarbony)lamino](1-vinylcyclopentyl)acetic acid (as described in Robl, Jeffrey A.; Sulsky, Richard B.; Augeri, David J.; Magnin, David R.; Hamann, Lawrence G.; Betebenner, David A. Preparation of fused cyclopropylpyrrolidine-based inhibitors of dipeptidyl peptidase IV, WO 200168603A2) (1.07 g, 3.97 mmol) was added Hünig's Base (0.835 mL, 4.37 mmol) and HATU (1.66 g, 4.37 mmol). The resulting solution was stirred for 15 minutes at RT, an then a solution of (2S,4S)-4-fluoro-2-pyrrolidinecarbonitrile 4-methylbenzenesulfonate (1.14 g, 3.97 mmol) and Hünig's base (0.835 mL, 4.37 mmol) in 10 mL of DMF was added dropwise over 2–3 minutes. The resulting solution was stirred at RT for 18 hr then quenched with $H_2O$. The solution was poured into $H_2O$ and the organics extracted with EtOAc (2×). After washing with sat NaCl and 1.0 N HCl the organics were dried ($MgSO_4$) and the solvent removed in vacuo to provide a dark oil, which was purified on silica gel using a Biotage FlashElute System, eluting in gradient fashion with hexanes/EtOAc 3:1 to 1:1 to afford 2 products, diastereomeric at the alpha-amino position (C1), in approximately a 1:1 ratio (582 mg of diastereomer 1, 628 mg of diastereomer 2, 83% overall yield). The slower-eluting diastereomer was determined to have the (S) absolute stereochemistry on the basis of vibrational circular dichroism analysis of the final product.

$^1$H NMR ($CDCl_3$) 400 MHz δ 5.92 (dd 1H, J=10.8, 17.3 Hz), 5.38 (m, 1H), 5.22 (dd, 2H J=10.8, 27.4 Hz), 5.02 (d, 1H, J=10.3 Hz), 4.23 (d, 1H, J=9.2 Hz), 4.06 (m, 2H), 2.63 (t, 1H, J=15.5 Hz), 2.40–2.23 (m, 2H), 1.85 (m, 1H), 1.75–1.52 (m, 6H), 1.43 (m, 1H), 1.37 (s, 9H) ppm.

B. (2S,4S)-1-[(2S)-2-amino-2-(1-vinylcyclopentyl)ethanoyl]-4-fluoropyrrolidine-2-carbonitrile hydrochloride.

To a flask containing tert-butyl (1S)-2-[(2S,4S)-2-cyano-4-fluoropyrrolidin-1-yl]-2-oxo-1-(1-vinylcyclopentyl)ethylcarbamate (70 mg, 0.19 mmol) in 1 mL of 1,4-dioxane was added 2 mL of 4 N HCl in 1,4-dioxane followed by 1 mL of 2 N HCl in $Et_2O$. The resulting solution was stirred at RT for 3 hr at which time starting material had been consumed as judged by TLC. 3 mL of $Et_2O$ was added to the reaction mixture followed by 3 mL of hexanes. The resulting light tan precipitate was filtered, triturated with $Et_2O$, collected via vacuum filtration and dried under vacuum to afford compound B as a cream-colored solid (35 mg, 70% yield).

$^1$H NMR ($d_4$-MeOH) 400 MHz δ 5.83 (dd, 1H, J=10.7, 17.6 Hz), 5.36 (dd, 2H, J=10.7, 27.7 Hz), 5.07 (d, 1H, J=9.7 Hz), 4.16 (m, 2H), 3.79 (m, 1H), 2.63 (t, 1H. J=16.2 Hz), 2.45 (m, 1H), 1.86–1.58 (m, 7H), 1.36 (M, 3H) ppm.

Example 13

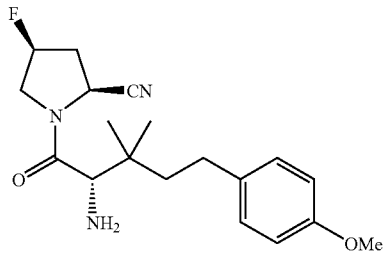

(2S,4S)-1-[(2S)-2-Amino-5-(4-methoxyphenyl)-3,3-dimethylpentanoyl]-4-fluoropyrrolidine-2-carbonitrile hydrochloride A. 4-(4-Methoxyphenyl)-2,2-dimethylbutanal.

To a toluene solution (80 mL) containing 4-(4-methoxyphenyl)-2,2-dimethylbutanenitrile (3.65 g, 18.0 mmol; see:

Knochel, P. et al. Org. Lett. 2000, 2, 3285 for the preparation of this compound) cooled to –78° C. was added 18.0 mL of a 1.5 M toluene solution of DIBAL (27.0 mmol). After 3 hr at –78° C. the reaction was quenched with a $H_2O$/THF solution (75 mL/15 mL) containing sodium acetate (4.6 g) and acetic acid (4.6 mL) at –78° C. To this solution was added celite followed by $Et_2O$. The solution was allowed to warm to RT at which time it was filtered through a bed of celite. The celite was rinsed thoroughly with $Et_2O$ and then the filtrate washed with $H_2O$. After drying over $MgSO_4$ the solvent was removed in vacuo and the residue purified via column chromatography (hexanes/EtOAc (9:1)) yielding 3.55 g (17.2 mmol, 96% yield) of compound A.

$^1$H NMR ($CDCl_3$) 400 MHz δ 9.47 (s, 1H), 7.07 (d, 2H, J=8.6 Hz), 6.81 (d, 2H, J=8.4 Hz), 3.78 (s, 3H), 2.48–2.44 (m, 2H), 1.77–1.73 (m, 2H), 1.11 (s, 6H) ppm.

B. 1,1,1-Trichloro-5-(4-methoxyphenyl)-3,3-dimethylpentan-2-ol.

To a THF solution (10 mL) containing compound A (511 mg, 2.48 mmol) and anhydrous chloroform (311 mg, 2.60 mmol) cooled to –78° C. was added 2.6 mL of a 1.0 M THF solution of LIHMDS (2.60 mmol) dropwise over 5 min. The resulting solution stirred at –78° C. for 30 min at which time the reaction was quenched with $H_2O$. Upon warming the organics were extracted with EtOAc and after drying over $MgSO_4$ the solvent was removed in vacuo. The residual yellow oil was purified via column chromatography (10% EtOAc/hexanes) yielding 588 mg (1.81 mmol, 73% yield) of compound B as a white solid.

$^1$H NMR ($CDCl_3$) 400 MHz δ 7.10 (d, 2H, J=8.7 Hz), 6.82 (d, 2H, J=8.4 Hz), 4.05 (d, 1H, J=5.7 Hz), 3.78 (s, 3H), 2.95 (d, 1H, J=5.7 Hz), 2.64–2.59 (m, 2H), 1.95 (m, 1H), 1.73 (m, 1H), 1.32 (s, 3H), 1.25 (s, 3H) ppm.

C. 2-Azido-5-(4-methoxyphenyl)-3,3-dimethylpentanoic acid.

To a DME solution (4 mL) containing compound B (581 mg, 1.79 mmol) was added 7 mL of an aqueous solution containing sodium azide (232 mg, 3.58 mmol) and sodium hydroxide (286 mg, 7.15 mmol) at RT. After stirring overnight the solution was poured into 2.0 M NaOH and the organics extracted with $Et_2O$. The aqueous layer was acidified with sat $NaHSO_4$ and the organics extracted with EtOAc (2×). After drying over $MgSO_4$ the solvent was removed in vacuo and the residual oil purified via column chromatography (5% MeOH/$CH_2Cl_2$) yielding 186 mg (0.67 mmol, 37% yield) of compound C.

$^1$H NMR ($CDCl_3$) 400 MHz δ 7.09 (d, 2H, J=8.4 Hz), 6.82 (d, 2H, J=8.6 Hz), 3.91 (s, 1H), 3.78 (s, 3H), 2.58–2.52 (m, 2H), 1.71–1.61 (m, 2H), 1.10 (s, 6H) ppm.

D. (2S,4S)-1-[2-Azido-5-(4-methoxyphenyl)-3,3-dimethylpentanoyl]-4-fluoropyrrolidine-2-carbonitrile.

To a DMF solution (15 mL) containing compound C (696 mg, 2.52 mmol) and N,N-diisopropylethylamine (358 mg, 2.77 mmol) was added HATU (1.05 g, 2.77 mmol) at RT. After 20 min a DMF solution (8 mL) containing (2S,4S)-4-fluoro-2-pyrrolidinecarbonitrile 4-methylbenzenesulfonate (755 mg, 2.64 mmol) and N,N-diisopropylethylamine (341 mg, 2.64 mmol) was added. The solution stirred overnight at which time it was diluted with EtOAc and washed with $H_2O$ (3×), sat. $NaHCO_3$ and 2.0 M HCl. After drying over $MgSO_4$ the solvent was removed in vacuo. The residual yellow oil was purified via column chromatography (initially hexanes/EtOAc/$CH_2Cl_2$ (6:3:1) then hexanes/EtOAc/$CH_2Cl_2$ (3:1:1)) yielding 605 mg (1.62 mmol, 64% yield) of compound D as a white solid that by $^1$H NMR was a 3:2 mixture of diastereomers. The diastereomeric mixture was taken on.

E. (2S,4S)-1-[(2S)-2-Amino-5-(4-methoxyphenyl)-3,3-dimethylpentanoyl]-4-fluoropyrrolidine-2-carbonitrile hydrochloride.

To an EtOH solution (8 mL) containing 10% Pd/C (200 mg) was added a 1:1 THF/EtOH solution (10 mL) containing compound D (593 mg, 1.59 mmol). The solution was degassed 4× and then placed under a balloon of hydrogen. After 6.5 hr the solution was filtered through a bed of celite with the celite being rinsed thoroughly with $CH_2CH_2$. The solvent was removed in vacuo and the residual solid purified via column chromatography (5% methanolic $NH_3/CH_2Cl_2$) yielding 251 mg (0.72 mmol) of compound E as the freebase. This material was then dissolved in 2 mL of $CH_2Cl_2$ and 3.0 mL of a 4.0 M dioxane solution of HCl was added. The solvent was then immediately removed in vacuo and the residual oil triterated with $Et_2O$. The resulting soild was collected via vacuum filtration yielding 231 mg (0.60 mmol) of compound E as the hydrochloride salt.

$^1$H NMR ($d_4$-MeOH) 400 MHz δ 7.13 (d, 2H, J=8.6 Hz), 6.81 (d, 2H, J=8.7 Hz), 5.31 (d(br), 1H, J=51.1 Hz), 5.09 (d, 1H, J=9.5 Hz), 4.10 (m, 1H), 4.01 (s, 1H), 3.86 (m, 1H), 3.74 (s, 3H), 2.65–2.42 (m, 4H), 1.76–1.72 (m, 2H), 1.20 (s, 6H) ppm.

Example 14

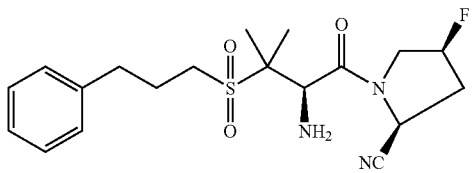

(2S,4S)-1-{(2R)-2-Amino-3-methyl-3-[(3-phenylpropyl)sulfonyl]butanoyl}-4-fluoropyrrolidine-2-carbonitrile A. Tert-butyl (1R)-1-{[(2S,4S)-2-cyano-4-fluoropyrrolidin-1-yl]carbonyl}-2-methyl-2-[(3-phenylpropyl)sulfonyl]propylcarbamate.

To a $CHCl_3$ (50 mL) solution containing tert-butyl (1R)-1-{[(2S,4S)-2-cyano-4-fluoropyrrolidin-1-yl]carbonyl}-2-methyl-2-[(3-phenylpropyl)thio]propylcarbamate (as described above) (830 mg, 1.79 mmol, 1.0 eq) was added 3-chloroperoxybenzoic acid (3.09 g, 17.9 mmol, 10 eq). The resulting mixture was stirred at RT for 18 h. The reaction was then quenched with 1.0 N NaOH (ca 10 mL) and the layers separated. The organic layer was dried over $MgSO_4$ and concentrated in vacuo. The resulting white fluffy solid was used in the next step without further purification. Isolated 800 mg of compound A (1.62 mmol, 91% yield).

B. (2S,4S)-1-{(2R)-2-amino-3-methyl-3-[(3-phenylpropyl)sulfonyl]butanoyl}-4-fluoropyrrolidine-2-carbonitrile To a $CH_2Cl_2$ (50 mL) solution containing trifluoroacetic acid (5 mL) was added compound A (800 mg, 1.62 mmol, 1.0 eq). The resulting pale yellow solution was stirred at RT for 2 h at which time the solvent was removed in vacuo. The resulting TFA salt was converted to the free base by addition of a sat. $NaHCO_3$ solution and extracting the aqueous layer (2×) with EtOAc. The combined organic extracts were dried over $Na_2SO_4$ and concentrated in vacuo. The resulting off-white foam was purified via flash chromatography using 5% MeOH (with 0.1% $NH_3$) in $CH_2Cl_2$ as the mobile phase affording 532 mg of compound B as the freebase (1.35 mmol, 83% yield). To form the HCl salt, the free base was taken up in $Et_2O$ and acetone added until all solids were in solution. 2.0 M HCl in ether was added dropwise until no more precipitate formed. The precipitate was then filtered and washed several times with $Et_2O$. The resulting salt was dried under high vacuum.

$^1$H NMR ($D_2O$) 400 MHz δ 7.26–7.13 (m, 5H), 5.48 (d, 1H, J=50.7 Hz), 5.00 (d, 1H, J=9.7 Hz), 4.63 (s, 1H), 4.02 (m, 1H), 3.81 (m, 1H), 3.20–3.15 (m, 2H), 2.71 (t, 2H, J=7.5 Hz), 2.65–2.33 (m, 2H), 2.09–2.01 (m, 2H), 1.50 (s, 3H), 1.35 (s, 3H) ppm.

Example 15

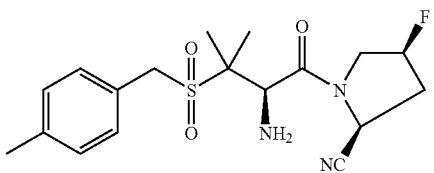

(2S,4S)-1-{(2R)-2-Amino-3-methyl-3-[(4-methylbenzyl)sulfonyl]butanoyl}-4-fluoropyrrolidine-2-carbonitrile A. (2R)-2-[(Tert-butoxycarbonyl)amino]-3-methyl-3-[(4-methylbenzyl)thio]butanoic acid To a 1.0 N NaOH (50 mL) solution containing (2R)-2-[(tert-butoxycarbonyl)amino]-3-mercapto-3-methylbutanoic acid (as described above) (1.0 g, 4.01 mmol, 1.0 eq) was added 4-methylbenzyl chloride (584 μL, 4.41 mmol, 1.1 eq). The resulting mixture was allowed to stir at RT for 18 h. The reaction mixture was then poured into a seperatory funnel and washed with $Et_2O$ (1×) to remove any unreacted chloride. Concentrated HCl was added to the aqueous layer until the pH reached 2–3. The aqueous layer was then extracted with $Et_2O$ (2×). The combined organic extracts were dried over $MgSO_4$ and concentrated in vacuo. The resulting white fluffy solid was used in the next step without further purification. Isolated 1.29 g of compound A (3.65 mmol, 91% yield).

$^1$H NMR ($CDCl_3$) 400 MHz δ 7.21 (d, 2H, J=7.9 Hz), 7.11 (d, 2H, J=8.3 Hz), 5.46 (d (br), 1H, J=8.5 Hz), 4.40 (s (br), 1H), 3.83 (q, 2H, J=11.7 Hz), 2.31 (s, 3H), 1.48–1.42 (m, 15H) ppm.

B. Tert-butyl (1R)-1-{[(2S,4S)-2-cyano-4-fluoropyrrolidin-1-yl]carbonyl}-2-methyl-2-[(4-methylbenzyl)thio]propylcarbamate.

To a DMF solution (25 mL) containing compound A (1.29 g, 3.65 mmol, 1.2 eq) was added N,N-diisopropylethylamine (715 μL, 4.1 mmol, 1.35 eq) followed by HATU (1.96 g, 5.17 mmol, 1.7 eq). The resulting amber solution was stirred at RT for 20 min. To this stirring solution was added a solution of (2S, 4S)-4-fluoro-2-pyrrolidinecarbonitrile 4-methylbenzenesulfonate (869 mg, 3.04 mmol, 1.0 eq) and N,N-diisopropylethylamine (582 μL, 3.34 mmol, 1.1 eq) in DMF (15 mL). The resulting solution was stirred at RT for 18 h and quenched with a sat. $NaHCO_3$ solution (ca 5 ml). The cloudy solution was then poured into $H_2O$ (ca 20 mL) and extracted with EtOAc (3×10 ml). The combined organic extracts were washed with $H_2O$ (2×) and brine (1×); dried over MgSO$_4$ and concentrated in vacuo. The resulting amber oil was purified via flash chromatography using 1:1 hexanes/EtOAc as the mobile phase. Isolated 1.14 g (2.54 mmol, 84% yield) of compound B as a white foam.

$^1$H NMR (CDCl$_3$) 400 MHz δ 7.26 (d, 2H, J=8.4 Hz), 7.10 (d, 2H, J=7.8 Hz), 5.48 (d 1H, J=51.9 Hz), 5.44 (d, 1H, J=9.5 Hz), 5.04 (d, 1H J=9.2 Hz), 4.37 (d, 1H, J=9.0 Hz), 4.25 (m, 1H), 4.04 (m, 1H), 3.81 (s, 2H), 2.72 (t, 1H, J=15.2 Hz), 2.45–2.28 (m, 4H), 1.47–1.41 (m, 15H) ppm.

C. tert-butyl (1R)-1-{[(2S,4S)-2-cyano-4-fluoropyrrolidin-1-yl]carbonyl}-2-methyl-2-[(4-methylbenzyl)sulfonyl]propylcarbamate.

To a CHCl$_3$ (75 mL) solution containing compound B (1.14 g, 2.54 mmol, 1.0 eq) was added 3-chloroperoxybenzoic acid (3.09 g, 17.9 mmol, 10 eq). The resulting mixture was stirred at RT for 18 h. The reaction was then quenched with 1.0 N NaOH (ca 15 mL) and the layers separated. The organic layer was dried over MgSO$_4$ and concentrated in vacuo. The resulting white fluffy solid was used in the next step without further purification. Isolated 1.03 g of compound C (2.14 mmol, 84% yield).

$^1$H NMR (CDCl$_3$) 400 MHz δ 7.32 (d, 2H, J=8.0 Hz), 7.19 (d, 2H, J=7.9 Hz), 5.51 (m, 1H), 5.48 (d, 1H, J=50.7 Hz), 5.04 (d. 1H, J=9.2 Hz), 4.99 (d, 1H, J=9.7 Hz), 4.32–3.97 (m, 4H), 2.72 (t. 1H, J=15.7 Hz), 2.46–2.29 (m, 4H), 1.58 (s, 3H), 1.52 (s, 3H), 1.41 (s, 9H) ppm.

D. (2S,4S)-1-{(2R)-2-amino-3-methyl-3-[(4-methylbenzyl)sulfonyl]butanoyl}-4-fluoropyrrolidine-2-carbonitrile To a CH$_2$Cl$_2$ (100 mL) solution containing trifluoroacetic acid (10 mL) was added compound C (1.03 g, 2.14 mmol, 1.0 eq). The resulting pale yellow solution was stirred at RT for 2 h at which time the solvent was removed in vacuo. The resulting TFA salt was converted to the free base by addition of a sat. NaHCO$_3$ solution and extracting the aqueous layer (2×) with EtOAc. The combined organic extracts were dried over Na$_2$SO$_4$ and concentrated in vacuo. The resulting off-white foam was purified via flash chromatography using 5% MeOH (with 0.1% NH$_3$) in CH$_2$Cl$_2$ as the mobile phase affording 577 mg (1.51 mmol, 71% yield) of compound D freebase as a white foam. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (d$_4$-MeOH) 400 MHz δ 7.38 (d, 2H, J=8.1 Hz), 7.24 (d, 2H, J=7.7 Hz), 5.56 (d, 1H, J=50.7 Hz), 5.12 (d, 1H, J=9.7 Hz), 4.74 (s, 1H), 4.64 (ABq, 2H, J=19.7,13.3 Hz), 4.12 (m, 1H), 3.94 (m, 1H), 2.70–2.43 (m, 2H), 2.36 (s, 3H), 1.76 (s, 3H), 1.58 (s, 3H) ppm.

Example 16

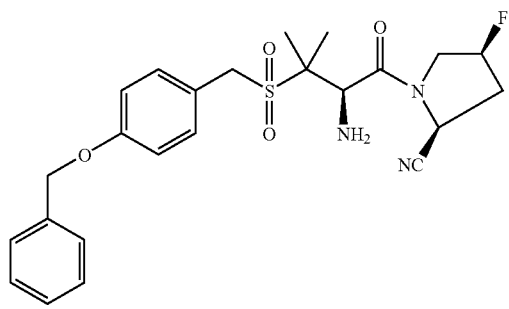

(2S,4S)-1-((2R)-2-amino-3-[{4-(benzyloxy)benzyl]sulfonyl}-3-methylbutanoyl)-4-fluoropyrrolidine-2-carbonitrile A. (2R)-3-{[4-(benzyloxy)benzyl]thio}-2-[(tert-butoxycarbonyl)amino]-3-methylbutanoic acid To a 1.0 N NaOH (25 mL) solution containing (2R)-2-[(tert-butoxycarbonyl)amino]-3-mercapto-3-methylbutanoic acid (as described above) (500 mg, 2.01 mmol, 1.0 eq) was added 4-benzyloxybenzyl chloride (515 mg, 2.21 mmol, 1.1 eq). The resulting mixture was allowed to stir at RT for 18 h. The reaction mixture was then poured into a seperatory funnel and washed with Et$_2$O (1×) to remove any unreacted chloride. Concentrated HCl was added to the aqueous layer until the pH reached 2–3. The aqueous layer was then extracted with Et$_2$O (2×). The combined organic extracts were dried over MgSO$_4$ and concentrated in vacuo. The resulting white fluffy solid was used in the next step without further purification. Isolated 700 mg of compound A (1.57 mmol, 78% yield).

$^1$H NMR (CDCl$_3$) 400 MHz δ 7.42–7.31 (m, 5H), 7.24 (d, 2H, J=8.6 Hz), 6.90 (d, 2H, J=8.6 Hz), 5.46 (s(br), 1H), 5.03 (s, 2H), 4.39 (s(br), 1H), 3.81 (q, 2H, J=11.5 Hz), 1.47–1.41 (m, 15H) ppm.

B. Tert-butyl (1R)-2-{[4-(benzyloxy)benzyl]thio}-1-{[(2S,4S)-2-cyano-4-fluoropyrrolidin-1-yl]carbonyl}-2-methylpropylcarbamate.

To a DMF solution (20 mL) containing compound A (700 mg, 1.57 mmol, 1.2 eq) was added N,N-diisopropylethylamine (308 μL, 1.77 mmol, 1.35 eq) followed by HATU (847 mg, 2.23 mmol, 1.7 eq). The resulting amber solution was stirred at RT for 20 min. To this stirring solution was added a solution of (2S, 4S)-4-fluoro-2-pyrrolidinecarbonitrile 4-methylbenzenesulfonate (375 mg, 1.31 mmol, 1.0 eq) and N,N-diisopropylethylamine (251 μl 1.44 mmol, 1.1 eq) in DMF (10 mL). The resulting solution was stirred at RT for 18 h and quenched with a sat. NaHCO$_3$ solution (ca 5 mL). The cloudy solution was then poured into H$_2$O (ca 20 mL) and extracted with EtOAc (3×10 mL). The combined organic extracts were washed with H$_2$O (2×) and brine (1×); dried over MgSO$_4$ and concentrated in vacuo. The resulting amber oil was purified via flash chromatography using 1:1 hexanes/EtOAc as the mobile phase. Isolated 340 mg (0.628 mmol, 48% yield) of compound B as a white foam.

$^1$H NMR (CDCl$_3$) 400 MHz δ 7.42–7.27 (m, 7H), 6.91 (d, 2H, J=8.8 Hz), 5.46 (d, 1H, J=50.9 Hz), 5.43 (d, 1H, J=9.3 Hz), 5.05–5.01 (m, 3H), 4.37 (d, 1H, J=9.0 Hz), 4.26 (m, 1H), 4.03 (m, 1H), 3.80 (s, 2H), 2.71 (t, 1H, J=15.2 Hz), 2.36 (m, 1H), 1.47–1.41 (m, 15H) ppm.

C. Tert-butyl (1R)-2-{[4-(benzyloxy)benzyl]sulfonyl}-1-{[(2S,4S)-2-cyano-4-fluoropyrrolidin-1-yl]carbonyl}-2-methylpropylcarbamate.

To a CHCl$_3$ (30 mL) solution containing compound B (340 mg, 0.628 mmol, 1.0 eq) was added 3-chloroperoxybenzoic acid (1.08 g, 6.28 mmol, 10 eq). The resulting mixture was stirred at RT for 18 h. The reaction was then quenched with 1.0 N NaOH (ca 5 mL) and the layers separated. The organic layer was dried over MgSO$_4$ and concentrated in vacuo. The resulting white fluffy solid was used in the next step without further purification. Isolated 280 mg of compound C (0.488 mmol, 78% yield).

$^1$H NMR (CDCl$_3$) 400 MHz δ 7.43–7.32 (m, 7H), 7.00 (d, 2H, J=8.8 Hz), 5.51 (s(br), 1H), 5.48 (d, 1H, J=50.7 Hz), 5.06–4.97 (m, 4H), 4.34–3.99 (m, 4H), 2.73 (t, 1H, J=15.2 Hz), 2.38 (m, 1H), 1.59 (s, 3H), 1.53 (s, 3H), 1.42 (s, 9H) ppm.

D. (2S,4S)-1-((2R)-2-Amino-3-{[4-(benzyloxy)benzyl]sulfonyl}-3-methylbutanoyl)-4-fluoropyrrolidine-2-carbonitrile.

To a CH$_2$Cl$_2$ (27 mL) solution containing trifluoroacetic acid (3 mL) was added compound C (280 mg, 0.488 mmol, 1.0 eq). The resulting pale yellow solution was stirred at RT for 2 h at which time the solvent was removed in vacuo. The resulting TFA salt was converted to the free base by addition of a sat. NaHCO$_3$ solution and extracting the aqueous layer (2×) with EtOAc. The combined organic extracts were dried over Na$_2$SO$_4$ and concentrated in vacuo. The resulting off-white foam was purified via flash chromatography using 5% MeOH (with 0.1% NH$_3$) in CH$_2$Cl$_2$ as the mobile phase affording 182 mg (0.385 mmol, 79% yield) of compound D freebase as a white foam. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (d$_4$-MeOH) 400 MHz δ 7.44–7.29 (m, 7H), 7.05 (d, 2H, J=8.8 Hz), 5.56 (d, 1H, J=50.0 Hz), 5.11–5.09 (m, 3H), 4.72 (s, 1H), 4.61 (ABq, 2H, J=18.1, 13.5 Hz), 4.13 (m, 1H), 3.91 (m, 1H), 2.70–2.42 (m, 2H), 1.75 (s, 3H), 1.58 (s, 3H) ppm.

Example 17

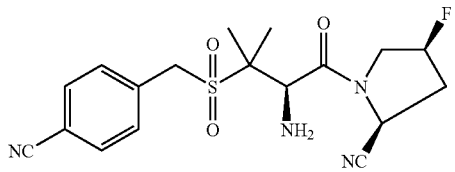

(2S,4S)-1-{(2R)-2-amino-3-[(4-cyanobenzyl)sulfonyl]-3-methylbutanoyl}-+fluoropyrrolidine-2-carbonitrile A. (2R)-2-[(tert-butoxycarbonyl)amino]-3-[(4-cyanobenzyl)thio]-3-methylbutanoic acid To a 1.0 N NaOH (25 mL) solution containing (2R)-2-[(tert-butoxycarbonyl)amino]-3-mercapto-3-methylbutanoic acid (as described above) (500 mg, 2.01 mmol, 1.0 eq) was added 4-cyanobenzyl bromide (433 mg, 2.21 mmol, 1.1 eq). The resulting mixture was allowed to stir at RT for 18 h. The reaction mixture was then poured into a seperatory funnel and washed with Et$_2$O (1×) to remove any unreacted chloride. Concentrated HCl was added to the aqueous layer until the pH reached 2–3. The aqueous layer was then extracted with Et$_2$O (2×). The combined organic extracts were dried over MgSO$_4$ and concentrated in vacuo. The resulting white fluffy solid was used in the next step without further purification. Isolated 792 mg of compound A (1.72 mmol, 86%/o yield).

B. Tert-butyl (1R)-2-[(4-cyanobenzyl)thio]-1-{[(2S,4S)-2-cyano-4-fluoropyrrolidin-1-yl]carbonyl}-2-methylpropylcarbamate.

To a DMF solution (25 mL) containing compound A (792 mg, 1.72 mmol, 1.2 eq) was added N,N-diisopropylethylamine (337 μL, 1.93 mmol, 1.35 eq) followed by HATU (924 mg, 2.43 mmol, 1.7 eq). The resulting amber solution was stirred at RT for 20 min. To this stirring solution was added a solution of (2S, 4S)-4-fluoro-2-pyrrolidinecarbonitrile 4-methylbenzenesulfonate (409 mg, 1.43 mmol, 1.0 eq) and N,N-diisopropylethylamine (274 μL, 1.57 mmol, 1.1 eq) in DMF (10 mL). The resulting solution was stirred at RT for 18 h and quenched with a sat NaHCO$_3$ solution (ca 5 mL). The cloudy solution was then poured into H$_2$O (ca 20 mL) and extracted with EtOAc (3×10 ml). The combined organic extracts were washed with H$_2$O (2×) and brine (1×); dried over MgSO$_4$ and concentrated in vacuo. The resulting amber oil was purified via flash chromatography using 1:1 hexanes/EtOAc as the mobile phase. Isolated 572 mg (1.24 mmol, 87% yield) of compound B as a white foam.

$^1$H NMR (CDCl$_3$) 400 MHz δ 7.59 (d, 2H, J=8.4 Hz), 7.50 (d, 2H, J=8.4 Hz), 5.50 (d, 1H, J=50.5 Hz), 5.42 (d, 1H, J=9.7 Hz), 5.03 (d, 1H, J=9.5 Hz), 4.41–4.30 (m, 2H), 4.04 (m, 1H), 3.88 (s, 2H), 2.75 (t, 1H, J=15.7 Hz), 2.39 (m, 1H), 1.46–1.41 (m, 15H) ppm.

C. Tert-butyl (1R)-2-[(4-cyanobenzyl)sulfonyl]-1-{[(2S,4S)-2-cyano-4-fluoropyrrolidin-1-yl]carbonyl}-2-methylpropylcarbamate.

To a CHCl$_3$ (50 mL) solution containing compound B (572 mg, 1.24 mmol, 1.0 eq) was added 3-chloroperoxybenzoic acid (2.14 g, 12.4 mmol, 10 eq). The resulting mixture was stirred at RT for 18 h. The reaction was then quenched with 1.0 N NaOH (ca 5 mL) and the layers separated. The organic layer was dried over MgSO$_4$ and concentrated in vacuo. The resulting white fluffy solid was used in the next step without further purification. Isolated 487 mg of compound C (0.989 mmol, 80% yield).

$^1$H NMR (CDCl$_3$) 400 MHz δ 7.70 (d, 2H, J=8.5 Hz), 7.57 (d, 2H, J=8.4 Hz), 5.53 (s(br), 1H), 5.51 (d, 1H, J=50.7 Hz), 5.04 (d, 1H, J=9.9 Hz), 4.99 (d, 1H, J=9.8 Hz), 4.43–4.29 (m, 3H), 4.04 (m, 1H), 2.77 (t, 1H, J=15.0 Hz), 2.42 (m, 1H), 1.61 (d, 6H, J=5.8 Hz), 1.44 (s, 9H) ppm.

D. (2S,4S)-1-{(2R)-2-Amino-3-[(4-cyanobenzyl)sulfonyl]-3-methylbutanoyl}-4-fluoropyrrolidine-2-carbonitrile.

To a CH$_2$Cl$_2$ (54 mL) solution containing trifluoroacetic acid (6 mL) was added compound C (487 mg, 0.989 mmol, 1.0 eq). The resulting pale yellow solution was stirred at RT for 2 h at which time the solvent was removed in vacuo. The resulting TFA salt was converted to the free base by addition of a sat. NaHCO$_3$ solution and extracting the aqueous layer (2×) with EtOAc. The combined organic extracts were dried over Na$_2$SO$_4$ and concentrated in vacuo. The resulting off-white foam was purified via flash chromatography using 5% MeOH (with 0.1% NH$_3$) in CH$_2$Cl$_2$ as the mobile phase affording 285 mg (0.726 mmol, 73% yield) of compound D freebase as a white foam. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (D$_2$O) 400 MHz δ 7.72 (d, 2H, J=8.6 Hz), 7.51 (d, 2H, J=8.5 Hz), 5.49 (d, 1H, J=50.6 Hz), 5.02 (d, 1H, J=9.7 Hz), 4.72–4.67 (m, 3H), 4.08 (m, 1H), 3.85 (m, 1H), 2.66–2.35 (m, 2H), 1.66 (s, 3H), 1.51 (s, 3H) ppm.

Example 18

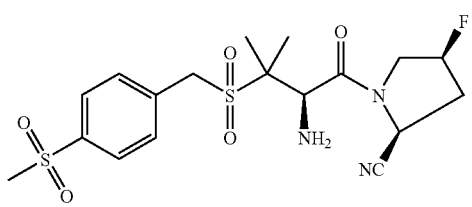

(2S,4S)-1-((2R)-2-amino-3-methyl-3-{[4-(methyl-sulfonyl)benzyl]sulfonyl}butanoyl)-4-fluoropyrrolidine-2-carbonitrile A. (2R)-2-[(tert-butoxycarbonyl)amino]-3-methyl-3-{[4-(methylsulfonyl)benzyl]thio}butanoic acid To a 1.0 N NaOH (25 mL) solution containing (2R)-2-[(tert-butoxycarbonyl)amino]-3-mercapto-3-methylbutanoic acid (as described above) (500 mg, 2.01 mmol, 1.0 eq) was added 4-methylsulfonylbenzyl chloride (452 mg, 2.21 mmol, 1.1 eq). The resulting mixture was allowed to stir at RT for 18 h. The reaction mixture was then poured into a seperatory funnel and washed with $Et_2O$ (1×) to remove any unreacted chloride. Concentrated HCl was added to the aqueous layer until the pH reached 2–3. The aqueous layer was then extracted with $Et_2O$ (2×). The combined organic extracts were dried over $MgSO_4$ and concentrated in vacuo. The resulting white fluffy solid was used in the next step without further purification. Isolated 768 mg of compound A (1.84 mmol, 92% yield).

$^1H$ NMR ($CDCl_3$) 400 MHz δ 7.87 (d, 2H, J=8.5 Hz), 7.54 (d, 2H, J=8.5 Hz), 5.39 (s(br), 1H), 4.44 (s(br), 1H), 3.88 (s, 2H), 3.03 (s, 3H), 1.46–1.43 (m, 15H) ppm.

B. Tert-butyl (1R)-1-{[(2S,4S)-2-cyano-4-fluoropyrrolidin-1-yl]carbonyl}-2-methyl-2-{[4-(methylsulfonyl)benzyl]thio}propylcarbamate.

To a DMF solution (25 mL) containing compound A (768 mg, 1.84 mmol, 1.2 eq) was added N,N-diisopropylethylamine (361 µL, 2.07 mmol, 1.35 eq) followed by HATU (989 mg, 2.60 mmol, 1.7 eq). The resulting amber solution was stirred at RT for 20 min. To this stirring solution was added a solution of (2S, 4S)-4-fluoro-2-pyrrolidinecarbonitrile 4-methylbenzenesulfonate (438 mg, 1.53 mmol, 1.0 eq) and N,N-diisopropylethylamine (293 µL, 1.68 mmol, 1.1 eq) in DMF (10 mL). The resulting solution was stirred at RT for 18 h and quenched with a sat $NaHCO_3$ solution (ca 5 mL). The cloudy solution was then poured into $H_2O$ (ca 20 mL) and extracted with EtOAc (3×10 mL). The combined organic extracts were washed with $H_2O$ (2×) and brine (1×); dried over $MgSO_4$ and concentrated in vacuo. The resulting amber oil was purified via flash chromatography using 1:1 hexanes/EtOAc as the mobile phase. Isolated 683 mg (1.33 mmol, 87% yield) of compound B as a white foam.

$^1H$ NMR ($CDCl_3$) 400 MHz δ 7.86 (d, 2H, J=8.5 Hz), 7.58 (d, 2H, J=8.3 Hz), 5.50 (d, 1H, J=50.9 Hz), 5.43 (d, 1H, J=9.9 Hz), 4.43–4.30 (m, 2H), 4.03 (m, 1H), 3.90 (s, 2H), 3.02 (s, 3H), 2.74 (t, 1H, J=15.6 Hz), 2.39 (m, 1H), 1.47–1.41 (m, 15H) ppm.

C. Tert-butyl (1R)-1-{[(2S,4S)-2-cyano-4-fluoropyrrolidin-1-yl]carbonyl}-2-methyl-2-{[4-(methylsulfonyl)benzyl]sulfonyl}propylcarbamate.

To a $CHCl_3$ (50 mL) solution containing compound B (683 mg, 1.33 mmol, 1.0 eq) was added 3-chloroperoxybenzoic acid (2.30 g, 13.3 mmol, 10 eq). The resulting mixture was stirred at RT for 18 h. The reaction was then quenched with 1.0 N NaOH (ca 5 mL) and the layers separated. The organic layer was dried over $MgSO_4$ and concentrated in vacuo. The resulting white fluffy solid was used in the next step without further purification. Isolated 581 mg of compound C (1.06 mmol, 80% yield).

$^1H$ NMR ($CDCl_3$) 400 MHz δ 7.98 (d, 2H, J=8.6 Hz), 7.66 (d, 2H, J=8.5 Hz), 5.53 (s, 1H), 5.51 (d, 1H, J=50.5 Hz), 5.08 (d, 1H, J=10.0 Hz), 4.99 (d, 1H, J=9.5 Hz), 4.44–4.32 (m, 2H), 4.03 (m, 1H), 3.06 (s, 3H), 2.77 (t, 1H, J=16.0 Hz), 2.41 (m, 1H), 1.63 (s, 3H), 1.60 (s, 3H), 1.43 (s, 9H) ppm.

D. (2S,4S)-1-((2R)-2-Amino-3-methyl-3-{[4-(methylsulfonyl)benzyl]sulfonyl}butanoyl)-4-fluoropyrrolidine-2-carbonitrile.

To a $CH_2Cl_2$ (63 mL) solution containing trifluoroacetic acid (7 mL) was added compound C (581 mg, 1.06 mmol, 1.0 eq). The resulting pale yellow solution was stirred at RT for 2 h at which time the solvent was removed in vacuo. The resulting TFA salt was converted to the free base by addition of a sat $NaHCO_3$ solution and extracting the aqueous layer (2×) with EtOAc. The combined organic extracts were dried over $Na_2SO_4$ and concentrated in vacuo. The resulting off-white foam was purified via flash chromatography using 5% MeOH (with 0.1% $NH_3$) in $CH_2Cl_2$ as the mobile phase affording 296 mg (0.664 mmol, 63% yield) of compound D freebase as a white foam. To form the HCl salt, the free base was taken up in $Et_2O$ and acetone added until all solids were in solution. 2.0 M HCl in ether was added dropwise until no more precipitate formed. The precipitate was then filtered and washed several times with $Et_2O$. The resulting salt was dried under high vacuum.

$^1H$ NMR ($D_2O$) 400 MHz δ 7.91 (d, 2H, J=8.1 Hz), 7.63 (d, 2H, J=8.2 Hz), 5.49 (d, 1H, J=50.3 Hz), 5.02 (d, 1H, J=9.7 Hz), 4.77–4.68 (m, 3H), 4.09 (m, 1H), 3.85 (m, 1H), 3.14 (s, 3H), 2.66–2.36 (m, 2H), 1.67 (s, 3H), 1.53 (s, 3H) ppm.

Example 19

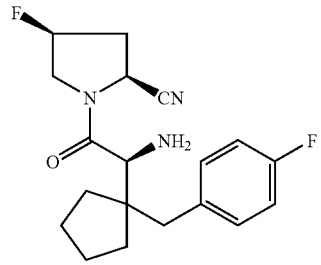

(2S,4S)-1-{(2S)-2-Amino-2-[1-(4-fluorobenzyl)cyclopentyl]ethanoyl}-4-fluoropyrrolidine-2-carbonitrile hydrochloride A. 1-(4-Fluorobenzyl)cyclopentanecarbonitrile.

To a stirred solution of 4-fluorobenzyl bromide (10.0 g, 52.9 mmol) in toluene (100 mL) was added cyclopentanecarbonitrile (6.1 mL, 58.2 mmol). The mixture was stirred thoroughly and cooled to 0° C. A solution of 0.5 M KHMDS in toluene (159 mL, 79.35 mmol) was added slowly via an addition funnel, and the reaction mixture was then warmed to RT and stirred for 14 hours. The reaction mixture was then quenched with 1.0 M HCl until pH<7. The layers were separated and aqueous layer was re-extracted with EtOAc. The combined organic layers were washed with saturated NaHCO$_3$, water, brine, dried over MgSO$_4$, filtered, and concentrated in vacuo. Purification via silica gel chromatography (10:1 hexanes:EtOAc) afforded 8.61 g (80% yield) of compound A as a yellow liquid.

$^1$H NMR (CDCl$_3$) 400 MHz δ 7.28–7.24 (m, 2H), 7.01 (t, J=8.7 Hz, 2H), 2.84 (s, 2H), 2.07–2.01 (m, 2H), 1.89–1.66 (m, 6H) ppm.

B. 1-(4-Fluorobenzyl)cyclopentanecarbaldehyde.

A stirred solution of compound A (8.61 g, 42.36 mmol) in toluene (150 mL) was cooled to −78° C. Neat diisobutylaluminum hydride (DIBAL 11.3 mL, 63.54 mmol) was added dropwise via syringe and the reaction mixture was stirred at −78° C. for 2 hours. A solution of THF (100 mL), water (30 mL), acetic acid (8 mL), and sodium acetate (7 g) was carefully added and the reaction mixture was warmed to RT and stirred one additional hour. After adding Et$_2$O, the biphasic mixture was vacuum filtered through a pad of Celite, poured into a separatory funnel, and the aqueous layer drawn off. The organic layer was washed with saturated NaHCO$_3$, water, brine, dried over MgSO$_4$, filtered, and concentrated in vacuo. Purification via silica gel chromatography (10:1 hexanes:EtOAc) afforded 6.55 g (75% yield) of compound B as a colorless liquid.

$^1$H NMR (CDCl$_3$) 400 MHz δ 9.53 (s, 1H), 7.07 (dd, J=8.4, 5.5 Hz, 2H), 6.93 (t, J=8.7 Hz, 2H), 2.88 (s, 2H), 1.93–1.87 (m, 2H), 1.67–1.48 (m, 6H) ppm.

C. Amino[1-(4-fluorobenzyl)cyclopentyl]acetonitrile.

To a stirred solution of compound B (6.55 g, 31.76 mmol) in methanol (30 mL) and water (18 mL) was added NH$_4$OH (~30% ammonia content, 4.4 mL, 33.35 mmol), KCN (2.17 g, 33.35 mmol), and NH$_4$Cl (1.87 g, 34.94 mmol). The cloudy reaction mixture was heated to 70° C. for 14 hours. After cooling to RT, the reaction mixture was diluted with EtOAc and washed with saturated NaHCO$_3$, water, brine, dried over MgSO$_4$, filtered, and concentrated in vacuo. Flash chromatography over silica gel (4:1 hexanes:EtOAc) afforded 5.99 g (81% yield) of compound C as a colorless, viscous oil.

$^1$H NMR (CDCl$_3$) 400 MHz δ 7.23–7.19 (m, 2H), 6.98 (t, J=8.7 Hz, 2H), 3.54 (d, J=3.5 Hz, 1H), 2.97 (d, J=13.6 Hz, 1H), 2.63 (d, J=13.7 Hz, 1H), 2.08 (br s, 2H), 1.75–1.57 (m, 8H) ppm.

D. Amino[1-(4-fluorobenzyl)cyclopentyl]acetic acid hydrochloride.

To a stirred solution of compound C (5.99 g, 25.79 mmol) in glacial acetic acid (20 mL) was added concentrated HCl (100 mL). The reaction mixture was heated to a gentle reflux (130° C.) for 16 hours. After cooling to RT, the reaction mixture was concentrated in vacuo to dryness producing a white solid. The solid was washed with Et$_2$O on a glass frit via vacuum filtration and dried under high vacuum to produce 6.33 g (85% yield) of compound D as a white solid.

$^1$H NMR (CD$_3$OD) 400 MHz δ 7.30 (dd, J=8.7, 5.4 Hz, 2H), 7.04 (t, J=8.8 Hz, 2H), 3.89 (s, 1H), 2.85–2.76 (m, 2H), 1.79–1.43 (m, 8H) ppm.

E. [(tert-Butoxycarbonyl)amino][1-(4-fluorobenzyl)cyclopentyl]acetic acid.

To a stirred solution of compound D (6.33 g, 21.99 mmol) in 1,4-dioxane (100 mL) was added a solution of 1.0 M NaOH in water (76 mL, 75.57 mmol) followed by water (24 mL). The reaction mixture was stirred at RT for several minutes until all of the starting material was completely dissolved. Solid di-tert-butyldicarbonate (BOC$_2$O, 8.25 g, 37.78 mmol) was added and the reaction mixture was stirred at RT for 14 hours. Concentrated HCl was then added slowly until pH<7 followed by dilution with EtOAc. The aqueous layer was separated and then re-extracted with two portions of EtOAc. The combined organic layers were dried over MgSO$_4$, filtered, and concentrated in vacuo to produce 7.95 g (90% yield) of compound E as a white foam.

$^1$H NMR (CDCl$_3$) 400 MHz δ 7.20 (dd, J=8.6, 5.5 Hz, 2H), 6.96 (t, J=8.7 Hz, 2H), 5.00 (d, J=9.1 Hz, 1H), 4.28 (d, J=9.0 Hz, 1H), 2.72–2.64 (m, 2H), 1.63–1.35 (m, 8H), 1.45 (s, 9H) ppm.

F. tert-Butyl (1S)-2-[(2S,4S)-2-cyano-4-fluoropyrrolidin-1-yl]-1-[1-(4-fluorobenzyl)cyclopentyl]-2-oxoethylcarbamate.

To a stirred solution of compound E (1.90 g, 5.41 mmol) in DMF (54 mL) was added (2S,4S)-4-fluoropyrrolidine-2-carbonitrile 4-methylbenzenesulfonate (1.55 g, 5.41 mmol), HATU (2.06 g, 5.41 mmol), and diisopropylethylamine (2.83 mL, 16.23 mmol). The reaction mixture was stirred at RT for 16 hours. After adding water (50 mL), the reaction mixture was extracted with five portions of EtOAc. The combined extracts were washed with water, saturated NH$_4$Cl, saturated NaHCO$_3$, brine, dried over MgSO$_4$, filtered, and concentrated in vacuo. The two diastereomers were separated via flash chromatography over silica gel (2:1 hexanes:EtOAc) to afford 586 mg (25% yield of the desired diastereomer) of compound F as a colorless oil. Compound F was the more polar (lower R$_f$) of the two diastereomers.

$^1$H NMR (CDCl$_3$) 400 MHz δ 7.20–7.16 (m, 2H), 7.00 (t, J=8.7, 2H), 5.22 (br d, J=51.1 Hz, 1H), 5.15 (d, J=5.9 Hz, 1H), 4.93 (d, J=9.3 Hz, 1H), 4.26 (d, J=9.7 Hz, 1H), 3.77–3.63 (m, 1H), 3.28–3.19 (m, 1H), 2.78–2.52 (m, 4H), 2.32–2.11 (m, 2H), 1.73–1.52 (m, 6H), 1.42 (s, 9H) ppm.

G. (2S,4S)-1-{(2S)-2-Amino-2-[1-(4-fluorobenzyl)cyclopentyl]ethanoyl}-4-fluoropyrrolidine-2-carbonitrile.

To a stirred solution of compound F (586 mg, 1.31 mmol) in CH$_2$CH$_2$ (13 mL) was added TFA (1.00 mL, 13.1 mmol). The reaction mixture was stirred at RT for 14 hours. After concentration in vacuo, the reaction mixture was re-dissolved in EtOAc and washed with saturated NaHCO$_3$, dried over MgSO$_4$, filtered, and concentrated in vacuo. Purification via silica gel flash chromatography (5% MeOH (with 2%/o NH$_3$) in CH$_2$Cl$_2$) afforded 160 mg (35% yield) of compound G as a white solid.

$^1$H NMR (CDCl$_3$) 400 MHz δ 7.21–7.17 (m, 2H), 6.99 (t, J=8.6 Hz, 2H), 5.24 (br d, J=51.1 Hz, 1H), 4.93 (d, J=9.3 Hz, 1H), 3.53–3.40 (m, 1H), 3.34 (s, 1H), 3.29–3.20 (m, 1H), 2.92 (d, J=13.6 Hz, 1H), 2.66 (d, J=13.7 Hz, 1H), 2.63–2.49 (m, 2H), 2.31–1.32 (m, 8H) ppm.

H. (2S,4S)-1-{(2S)-2-Amino-2-[1-(4-fluorobenzyl)cyclopentyl]ethanoyl}-4-fluoropyrrolidine-2-carbonitrile hydrochloride.

To a stirred solution of compound G (160 mg, 0.460 mmol) in Et$_2$O (5 mL) was added a solution of 2.0 M HCl in Et$_2$O (1.0 mL). The reaction mixture was stirred at RT for 5 minutes, during which time a white solid precipitated. The solid was collected via vacuum filtration on a glass frit and dried overnight under high vacuum to give 139 mg (79% yield) of compound H as a white solid.

$^1$H NMR (CD$_3$OD) 400 MHz δ 7.31–7.27 (m, 2H), 7.13 (t, J=8.8 Hz, 2H), 5.30 (br d, J=51.1 Hz, 1H), 5.01 (d, J=9.5 Hz, 1H), 4.04 (s, 1H), 3.56–3.43 (m, 1H), 3.20–3.11 (m, 1H), 2.90 (d, J=13.9 Hz, 1H), 2.73 (d, J=14.0 Hz, 1H), 2.60–2.30 (m, 2H), 2.14–1.37 (m, 8H) ppm.

Example 20

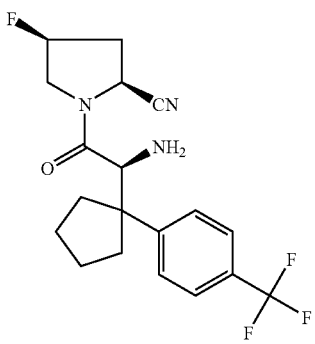

(2S,4S)-1-((2S)-2-Amino-2-{1-[4-(trifluoromethyl)
phenyl]cyclopentyl}ethanoyl)-4-fluoropyrrolidine-2-
carbonitrile hydrochloride A. 1-[4-(Trifluoromethyl)phenyl]cyclopentanecarbonitrile.

To a stirred solution of 4-fluorobenzotrifluoride (5.0 g, 30.47 mmol) in toluene (40 mL) was added cyclopentanecarbonitrile (10.5 mL, 100.55 mmol) followed by a solution of 0.5 M KHMDS in toluene (92 mL, 45.71 mmol). The reaction mixture was heated to 70° C. and stirred for 14 hours. After cooling to RT, the reaction mixture was quenched with 1 M HCl until pH<7. The layers were separated and the organic layer was washed with saturated NaHCO$_3$, water, brine, dried over MgSO$_4$, filtered, and concentrated in vacuo. Purification via silica gel chromatography (6:1 hexanes:EtOAc) afforded 7.53 g of a mixture of compound A and residual cyclopentanecarbonitrile. Because these two compounds were not easily separable by chromatography, this mixture was carried directly to the next step.

B. 1-[4-(Trifluoromethyl)phenyl]cyclopentanecarbaldehyde.

A stirred solution of compound A (7.53 g as described above) in toluene (100 mL) was cooled to −78° C. A solution of 1.5 M diisobutylaluminum hydride in toluene (DIBAL, 32.0 mL, 47.21 mmol) was added slowly via syringe and the reaction mixture was stirred at −78° C. for 2 hours. A solution of THF (100 mL), water (20 mL), acetic acid (6 mL), and sodium acetate (6.6 g) was carefully added and the reaction mixture was warmed to RT and stirred one additional hour. After adding Et$_2$O, the biphasic mixture was vacuum filtered through a pad of Celite, poured into a separatory funnel, and the aqueous layer drawn off. The organic layer was washed with saturated NaHCO$_3$, water, brine, dried over MgSO$_4$, filtered, and concentrated in vacuo. Purification via silica gel chromatography (10:1 hexanes:EtOAc) afforded 3.91 g (53% yield over the last two steps) of compound B as a colorless liquid.

$^1$H NMR (CDCl$_3$) 400 MHz δ 9.41 (s, 1H), 7.61 (d, J=8.1 Hz, 2H), 7.38 (d, J=8.2 Hz, 2H), 2.58–2.52 (m, 2H), 1.93–1.65 (m, 6H) ppm.

C. Amino{1-[4-(trifluoromethyl)phenyl]cyclopentyl}acetonitrile.

To a stirred solution of compound B (3.91 g, 16.14 mmol) in methanol (20 mL) and water (12 mL) was added NH$_4$OH (~30% ammonia content, 2.20 mL, 16.95 mmol), KCN (1.11 g, 16.95 mmol), and NH$_4$Cl (950 mg, 17.76 mmol). The cloudy reaction mixture was heated to 70° C. for 6 hours. After cooling to RT, the reaction mixture was diluted with EtOAc and washed with saturated NaHCO$_3$, water, brine, dried over MgSO$_4$, filtered, and concentrated in vacuo. Flash chromatography over silica gel (2:1 hexanes:EtOAc) afforded 2.16 g (50% yield) of compound C as a white solid.

$^1$H NMR (CDCl$_3$) 400 MHz δ 7.63 (d, J=8.4 Hz, 2H), 7.54 (d, J=8.4 Hz, 2H), 3.74 (s, 1H), 2.43–2.36 (m, 1H), 2.32–2.25 (m, 1H), 2.15–2.08 (m, 1H), 2.01–1.93 (m, 1H), 1.85–1.72 (m, 4H), 1.54 (br s, 2H) ppm.

D. Amino{1-[4-(trifluoromethyl)phenyl]cyclopentyl}acetic acid hydrochloride.

To a stirred solution of compound C (2.16 g, 8.05 mmol) in glacial acetic acid (10 mL) was added concentrated HCl (50 mL). The reaction mixture was heated to a gentle reflux (130° C.) for 16 hours. After cooling to RT, the reaction mixture was concentrated in vacuo to dryness producing a white solid. The solid was dried under high vacuum to produce 2.61 g (100% yield) of compound D as a white solid.

$^1$H NMR (d$_4$-MeOH) 400 MHz δ 7.69 (d, J=8.4 Hz, 2H), 7.60 (d, J=8.4 Hz, 2H), 4.20 (d, J=2.4 Hz, 1H), 2.42–2.34 (m, 2H), 2.27–2.19 (m, 1H), 2.14–2.07 (m, 1H), 1.86–1.79 (m, 2H), 1.61–1.51 (m, 2H) ppm.

E. [(tert-Butoxycarbonyl)amino]{1-[4-(trifluoromethyl)phenyl]cyclopentyl}acetic acid.

To a stirred solution of compound D (2.61 g, 8.05 mmol) in 1,4-dioxane (20 mL) and water (20 mL) was added solid NaOH (1.08 g, 27.06 mmol). After stirring at RT for several minutes, solid di-tert-butyidicarbonate (BOC$_2$O, 3.94 g, 18.04 mmol) was added and the reaction mixture was stirred at RT for 14 hours. Concentrated HCl was then added slowly until pH<7 followed by dilution with EtOAc. The aqueous layer was separated, saturated with NaCl, and then re-extracted with two portions of EtOAc. The combined organic layers were dried over MgSO$_4$, filtered, and concentrated in vacuo to produce 3.01 g (86%/o yield) of compound E as a colorless, viscous oil.

$^1$H NMR (CDCl$_3$) 400 MHz δ 7.55 (d, J=7.8 Hz, 2H), 7.40 (d, J=8.2 Hz, 2H), 4.85 (d, J=8.5 Hz, 1H), 4.55 (d, J=8.5 Hz, 1H), 2.43–1.59 (m, 8H), 1.42 (s, 9H) ppm.

F. tert-Butyl (1S)-2-[(2S,4S)-2-cyano-4-fluoropyrrolidin-1-yl]-2-oxo-1-{1-[4-(trifluoromethyl)phenyl]cyclopentyl}ethylcarbamate.

To a stirred solution of compound E (1.01 g, 2.61 mmol) in DMF (26 mL) was added (2S,4S)-4-fluoropyrrolidine-2-carbonitrile 4-methylbenzenesulfonate (747 mg, 2.61 mmol), HATU (993 mg, 2.61 mmol), and diisopropylethylamine (1.40 mL, 7.83 mmol). The reaction mixture was stirred at RT for 16 hours. After adding water (20 mL), the reaction mixture was extracted with five portions of EtOAc. The combined extracts were washed with water, 1.0 M NaHSO$_4$, saturated NaHCO$_3$, brine, dried over MgSO$_4$, filtered, and concentrated in vacuo. Purification via silica gel chromatography (1:1 hexanes:EtOAc) produced 442 mg (35% yield) of the product as a mixture of diastereomers. Further silica gel chromatography (2:1 hexanes:EtOAc) separated the diastereomers and afforded 145 mg of compound F as a white foam. Compound F was the more polar (lower R$_f$) of the two diastereomers.

$^1$H NMR (CDCl$_3$) 400 MHz δ 7.63 (d, J=8.4 Hz, 2H), 7.56 (d, J=8.6 Hz, 2H), 5.27 (d, J=9.7 Hz, 1H), 5.08 (br d, J=50.9 Hz, 1H), 4.84 (d, J=9.5 Hz, 1H), 4.49 (d, J=9.9 Hz, 1H), 3.63–3.50 (m, 1H), 2.77 (dd, J=23.6, 12.0 Hz, 1H), 2.48 (t, J=15.5 Hz, 1H), 2.25–2.20 (m, 2H), 2.10–2.03 (m, 2H), 1.77–1.71 (m, 2H), 1.52–1.48 (m, 2H), 1.41 (s, 9H) ppm.

G. (2S,4S)-1-((2S)-2-Amino-2-{1-[4-(trifluoromethyl)phenyl]cyclopentyl}ethanoyl)-4-fluoropyrrolidine-2-carbonitrile.

To a stirred solution of compound F (145 mg, 0.30 mmol) in $CH_2Cl_2$ (3 mL) was added TFA (0.116 mL, 1.50 mmol). The reaction mixture was stirred at RT for 14 hours. After concentration in vacuo, the reaction mixture was re-dissolved in EtOAc and washed with saturated $NaHCO_3$, dried over $MgSO_4$, filtered, and concentrated in vacuo. Purification via silica gel flash chromatography (5% MeOH (with 2% $NH_3$) in $CH_2Cl_2$) afforded 62 mg (54% yield) of compound G as a white solid.

$^1$H NMR ($CDCl_3$) 400 MHz δ 7.62 (d, J=8.2 Hz, 2H), 7.54 (d, J=8.6 Hz, 2H), 5.12 (br d, J=51.1 Hz, 1H), 4.86 (d, J=9.5 Hz, 1H), 3.57 (s, 1H), 3.55–3.42 (m, 1H), 2.97–2.88 (m, 1H), 2.50 (t, J=15.2 Hz, 1H), 2.24–2.10 (m, 5H), 1.99 (br s, 2H), 1.76–1.71 (m, 2H), 1.54–1.41 (m, 2H) ppm.

H. (2S,4S)-1-((2S)-2-Amino-2-{1-[4-(trifluoromethyl)phenyl]cyclopentyl}ethanoyl)-4-fluoropyrrolidine-2-carbonitrile hydrochloride.

Diethyl ether (3 mL) was added to a flask containing compound G (51 mg, 0.133 mmol). A few drops of acetone were added to allow the solution to become homogeneous. A solution of 2.0 M HCl in $Et_2O$ (1.0 mL) was added and the reaction mixture was stirred at RT for 5 minutes. The solvent was removed in vacuo and the resulting solid was dried overnight under high vacuum to afford 55 mg (98% yield) of compound H as a white solid.

$^1$H NMR ($D_2O$) 400 MHz δ 7.62 (d, J=8.8 Hz, 2H), 7.58 (d, J=9.0 Hz, 2H), 5.13 (br d, J=51.1 Hz, 1H), 4.86 (d, J=9.5 Hz, 1H), 4.37 (s, 1H), 3.54–3.40 (m, 1H), 2.95–2.86 (m, 1H), 2.44–2.18 (m, 4H), 1.92–1.84 (m, 2H), 1.64–1.58 (m, 2H), 1.33–1.25 (m, 2H) ppm.

Example 21

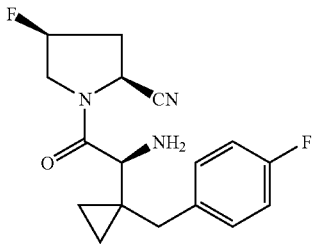

(2S,4S)-1-{(2S)-2-Amino-2-[1-(4-fluorobenzyl)cyclopropyl]ethanoyl}-4-fluoropyrrolidine-2-carbonitrile hydrochloride A. 1-(4-Fluorobenzyl)cyclopropanecarbonitrile.

A stirred solution of cyclopropanecarbonitrile (4.3 mL, 58.2 mmol) in toluene (100 mL) was cooled to 0° C. A solution of 0.5 M KHMDS in toluene (159 mL, 79.35 mmol) was added slowly via an addition funnel and the reaction mixture was stirred at 0° C. for 30 minutes. A solution of 4-fluorobenzyl bromide (10.0 g, 52.9 mmol) in toluene (20 mL) was then added dropwise at 0° C. The reaction mixture was warmed to RT and stirred for 3 hours. The reaction mixture was then quenched with 1.0 M HCl until pH<7. The layers were separated and aqueous layer was re-extracted with EtOAc. The combined organic layers were washed with saturated $NaHCO_3$, water, brine, dried over $MgSO_4$, filtered, and concentrated in vacuo. Purification via silica gel chromatography (5% EtOAc in hexanes) afforded 7.76 g (84% yield) of compound A as a yellow liquid.

$^1$H NMR ($CDCl_3$) 400 MHz δ 7.25–7.22 (m, 2H), 7.03 (t, J=8.7 Hz, 2H), 2.77 (s, 2H), 1.28 (dd, J=7.1, 5.1 Hz, 2H), 0.94 (dd, J=7.1, 5.1 Hz, 2H) ppm.

B. 1-(4-Fluorobenzyl)cyclopropanecarbaldehyde.

A stirred solution of compound A (7.76 g, 44.29 mmol) in toluene (150 mL) was cooled to −78° C. Neat diisobutylaluminum hydride (DIBAL, 11.8 mL, 66.43 mmol) was added dropwise via syringe and the reaction mixture was stirred at −78° C. for 2 hours. A solution of THF (100 mL), water (40 mL), acetic acid (8 mL), and sodium acetate (7.5 g) was carefully added and the reaction mixture was warmed to RT and stirred one additional hour. After adding $Et_2O$, the biphasic mixture was vacuum filtered through a pad of celite, poured into a separatory funnel, and the aqueous layer drawn off. The organic layer was washed with saturated $NaHCO_3$, water, brine, dried over $MgSO_4$, filtered, and concentrated in vacuo. Purification via silica gel chromatography (5% EtOAc in hexanes) afforded 7.20 g (91% yield) of compound B as a colorless liquid.

$^1$H NMR ($CDCl_3$) 400 MHz δ 8.71 (s, 1H), 7.16–7.13 (m, 2H), 6.94 (t, J=8.8 Hz, 2H), 2.96 (s, 2H), 1.20–1.17 (m, 2H), 1.00–0.97 (m, 2H) ppm.

C. Amino[1-(4-fluorobenzyl)cyclopropyl]acetonitrile.

To a stirred solution of compound B (7.20 g, 40.40 mmol) in methanol (40 mL) and water (25 mL) was added $NH_4OH$ (~30%/o ammonia content, 5.51 mL, 42.42 mmol), KCN (2.76 g, 42.42 mmol), and $NH_4Cl$ (2.38 g, 44.44 mmol). The cloudy reaction mixture was heated to 70° C. for 14 hours. After cooling to RT, the reaction mixture was diluted with EtOAc and washed with saturated $NaHCO_3$, water, brine, dried over $MgSO_4$, filtered, and concentrated in vacuo. Flash chromatography over silica gel (20% EtOAc in hexanes) afforded 2.21 g (27% yield) of compound C as a colorless, viscous oil.

$^1$H NMR ($CDCl_3$) 400 MHz δ 7.22–7.19 (m, 2H), 6.98 (t, J=8.6 Hz, 2H), 3.62 (d, J=3.3 Hz, 1H), 3.12 (d, J=14.3 Hz, 1H), 2.56 (d, J=14.3 Hz, 1H), 1.93 (brs, 1H), 1.82 (brs, 1H), 0.78–0.76 (m, 2H), 0.67–0.64 (m, 1H), 0.54–0.51 (m, 1H) ppm.

D. Amino[1-(4-fluorobenzyl)cyclopropyl]acetic acid hydrochloride.

To a stirred solution of compound C (2.21 g, 10.82 mmol) in glacial acetic acid (10 mL) was added concentrated HCl (50 mL). The reaction mixture was heated to a gentle reflux (130° C.) for 16 hours. After cooling to RT, the reaction mixture was concentrated in vacuo to dryness producing a white solid. The solid was washed with $Et_2O$ on a glass frit via vacuum filtration and dried under high vacuum to produce 2.81 g (100% yield) of compound D as a white solid.

$^1$H NMR ($d_4$-MeOH) 400 MHz δ 7.18 (dd, J=8.8, 5.5 Hz, 2H), 7.01 (t, J=8.8 Hz, 2H), 3.54 (s, 1H), 2.84 (d, J=4.9 Hz, 2H), 0.89–0.84 (m, 1H), 0.70–0.59 (m, 2H), 0.51–0.47 (m, 1H) ppm.

E. [(tert-Butoxycarbonyl)amino][1-(4-fluorobenzyl)cyclopropyl]acetic acid.

To a stirred solution of compound D (2.81 g, 10.85 mmol) in 1,4-dioxane (50 mL) was added a solution of 1.0 M NaOH in water (33 mL, 33.03 mmol) followed by water (17 mL). The reaction mixture was stirred at RT for several minutes until all of the starting material was completely dissolved. Solid di-tert-butyldicarbonate ($BOC_2O$, 3.60 g, 16.52 mmol) was added and the reaction mixture was stirred at RT for 14 hours. Concentrated HCl was then added slowly until pH<7 followed by dilution with EtOAc. The aqueous layer was separated and then re-extracted with two portions of EtOAc. The combined organic layers were dried over MgSO$_4$, filtered, and concentrated in vacuo to produce 4.06 g (112% yield) of compound E as a viscous, light yellow oil.

$^1$H NMR (CDCl$_3$) 400 MHz δ 7.19–7.15 (m, 2H), 6.95 (t, J=8.7 Hz, 2H), 4.98 (d, J=7.0 Hz, 1H), 3.98 (d, J=7.5 Hz, 1H), 2.85 (d, J=14.5 Hz, 1H), 2.60 (d, J=14.2 Hz, 1H), 1.45 (s, 9H), 0.79–0.72 (m, 2H), 0.51–0.47 (m, 2H) ppm.

F. tert-Butyl (1S)-2-[(2S,4S)-2-cyano-4-fluoropyrrolidin-1-yl]-1-[1-(4-fluorobenzyl)cyclopropyl]-2-oxoethylcarbamate.

To a stirred solution of compound E (4.06 g, 12.56 mmol) in DMF (125 mL) was added (2S,4S)-4-fluoropyrrolidine-2-carbonitrile 4-methylbenzenesulfonate (3.60 g, 12.56 mmol), HATU (4.78 g, 12.56 mmol), and diisopropylethylamine (6.60 mL, 37.68 mmol). The reaction mixture was stirred at RT for 16 hours. After adding water (125 mL), the reaction mixture was extracted with four portions of EtOAc. The combined extracts were washed with saturated NH$_4$Cl, saturated NaHCO$_3$, water, brine, dried over MgSO$_4$, filtered, and concentrated in vacuo. Purification via flash chromatography over silica gel (1:1 hexanes:EtOAc) afforded 1.29 g (25% yield) of the product as a mixture of diastereomers. Additional silica gel flash chromatography (2:1 hexanes: EtOAc) separated the diastereomers and afforded 853 mg of compound F as a white foam. Compound F was the more polar (lower R$_f$) of the two diastereomers.

$^1$H NMR (CDCl$_3$) 400 MHz δ 7.29 (dd, J=8.6, 5.5 Hz, 2H), 7.03 (t, J=8.7 Hz, 2H), 5.15 (d, J=9.3 Hz, 1H), 5.14 (br d, J=51.1 Hz, 1H), 4.76 (d, J=9.3 Hz, 1H), 4.42 (d, J=9.3 Hz, 1H), 3.29–3.16 (m, 1H), 3.15–3.11 (m, 1H), 3.07–2.98 (m, 1H), 2.52 (t, J=15.2 Hz, 1H), 2.24–2.17 (m, 1H), 2.14–2.07 (m, 1H), 1.44 (s, 9H), 0.86–0.76 (m, 2H), 0.56–0.45 (m, 2H) ppm.

G. (2S,4S)-1-{(2S)-2-Amino-2-[1-(4-fluorobenzyl)cyclopropyl]ethanoyl}-4-fluoropyrrolidine-2-carbonitrile.

To a stirred solution of compound F (853 mg, 2.03 mmol) in CH$_2$Cl$_2$ (20 mL) was added TFA (1.56 mL, 20.4 mmol). The reaction mixture was stirred at RT for 18 hours. After concentration in vacuo, the reaction mixture was re-dissolved in EtOAc and washed with saturated NaHCO$_3$, dried over MgSO$_4$, filtered, and concentrated in vacuo. Purification via silica gel flash chromatography (5% MeOH (with 2% NH$_3$) in CH$_2$Cl$_2$) afforded 401 mg (62% yield) of compound G as a white solid.

$^1$H NMR (CDCl$_3$) 400 MHz δ 7.27–7.24 (m, 2H), 7.00 (t, J=8.6 Hz, 2H), 5.17 (br d, J=51.3 Hz, 1H), 4.76 (d, J=9.3 Hz, 1H), 3.48 (s, 1H), 3.32–3.01 (m, 3H), 2.54 (t, J=15.0 Hz, 1H), 2.22–2.05 (m, 2H), 1.74 (br s, 2H), 0.79–0.71 (m, 2H), 0.53–0.39 (m, 2H) ppm.

H. (2S,4S)-1-{(2S)-2-Amino-2-[1-(4-fluorobenzyl)cyclopropyl]ethanoyl}-4-fluoropyrrolidine-2-carbonitrile hydrochloride.

Diethyl ether (8 mL) was added to a flask containing compound G (401 mg, 1.26 mmol). Approximately 1 mL of acetone was added to make the solution homogeneous. A solution of 2.0 M HCl in Et$_2$O (6.0 mL) was added and the reaction mixture was stirred for 5 minutes. Removal of the solvent in vacuo produced a white solid that was triturated with a portion of the HCl/Et$_2$O solution. The solid was collected via vacuum filtration on a glass frit, washed with several portions of Et$_2$O, and dried overnight under high vacuum to give 376 mg (84% yield) of compound H as a white solid.

$^1$H NMR (D$_2$O) 400 MHz δ 7.29–7.23 (m, 2H), 7.07–7.01 (m, 2H), 5.22 (br d, J=50.6 Hz, 1H), 4.82 (d, J=9.1 Hz, 1H), 4.10 (s, 1H), 3.25–2.92 (m, 3H), 2.28 (t, J=16.0 Hz, 1H), 2.32–2.21 (m, 2H), 1.16–0.43 (m, 4H) ppm.

Example 22

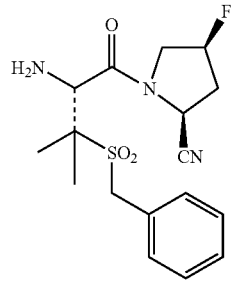

(2S,4S)-1-[(2R)-2-Amino-3-(benzylsulfonyl)-3-methylbutanoyl]-4-fluoropyrrolidine-2-carbonitrile hydrochloride A. (2R)-3-(benzylthio)-2-[(tert-butoxycarbonyl)amino]-3-methyl butanoic acid To a 1.0 N KOH solution (50 mL) containing (2R)-2-[(tert-butoxycarbonyl)amino]-3-mercapto-3-methylbutanoic acid (1 g, 0.00401 mole) was added benzyl bromide (755 mg, 0.00441 mole) at RT. After 17.0 hours the reaction mixture was diluted with water and washed with diethyl ether. The organics were discarded and the aqueous layer was cooled to 0–5° C. The aqueous solution was made acidic (pH 3.5) using concentrated HCl and the product was extracted into EtOAc. The organics were dried over MgSO$_4$ and concentrated to dryness to yield a total of 1.1 g (81%) of compound A as a pure oily solid.

$^1$H NMR (CDCl$_3$) 400 MHz δ 7.32–7.20 (m, 5H), 5.44 (d (br), 1H, J=7.2 Hz), 4.38 (d (br), 1H, J=8.0 Hz), 3.80 (m, 2H), 1.45–1.43 (m, 15H) ppm.

B. Tert-butyl (1R)-2-(benzylthio)-1-{[(2S,4S)-2-cyano-4-fluoropyrrolidin-1-yl]carbonyl}-2-methylpropylcarbamate.

To a DMF solution (20 mL) containing compound A (1.1 g, 0.0032 mole) and N,N-diisopropylethylamine (1.4 g, 0.0107 mole) was added HATU (1.85 g, 0.0049 mole) at RT. After 30 minutes the reaction mixture was mixed with (2S, 4S)-4-fluoro-2-pyrrolidinecarbonitrile 4-methylbenzenesulfonate (1.0 g, 0.0035 mole). After stirring overnight the reaction was quenched with NaHCO$_3$ and the organics extracted with EtOAc (2×). The organics were washed with sat. NaCl and dried over MgSO$_4$. Removal of the solvent in vacuo and purification via column chromatography (1/1 hexanes/EtOAc) yielded 445 mg (32%) of compound B.

$^1$H NMR (CDCl$_3$) 400 MHz δ 7.36–7.18 (m, 5H), 5.37 (d (br), 1H), 5.45 (d (br), 1H, J=51.6 Hz), 5.00 (d, 1H, J=9.2 Hz), 4.35 (d, 1H, J=8.8), 4.27–3.92 (m, 4H), 2.67–2.59 (m, 1H), 2.40–2.23 (m, 1H), 1.46–1.36 (m, 15H) ppm.

C. Tert-butyl (1R)-2-(benzylsulfonyl)-1-{[(2S,4S)-2-cyano-4-fluoropyrrolidin-1-yl]carbonyl}-2-methylpropylcarbamate.

To a CH$_2$Cl$_2$ solution (75 mL) containing compound B (445 mg, 0.00102 mole) was added 3-chloroperoxybenzoic acid (57–86%) (1.8 g 0.0102 mole). The reaction mixture was allowed to stir at RT for a period of 16.0 hours followed by neutralization with 2.0 N KOH. The organics were separated, dried over MgSO$_4$ and concentrated to dryness to afford 421 mg of crude compound C (88%). The resulting tan solid was used without further purification.

D. (2S,4S)-1-[(2R)-2-Amino-3-(benzylsulfonyl)-3-methylbutanoyl]-4-fluoropyrrolidine-2-carbonitrile hydrochloride.

To a CH$_2$Cl$_2$ solution (45 mL) containing compound C (421 mg, 0.00102 mole) was added TFA (5 mL). The reaction mixture was allowed to stir at RT for a period of 16.0 hours followed by neutralization with sat NaHCO$_3$. The organics were dried over MgSO$_4$ and concentrated to dryness to afford a crude solid. The resulting solid was purified using silica gel chromatography (99% CH$_2$Cl$_2$/1% MeOH with 2.0 M NH$_3$). The pure tan solid was dissolved into an acetone/ether mixture (1/1) and precipitated using 2.0 N HCl in ether. The resulting solid was filtered in vacuo and washed with ether. After drying under high vacuum the reaction yielded a total of 96 mg of compound D.

$^1$H NMR (d$_4$-MeOH) 400 MHz δ 7.49–7.35 (m, 5H), 5.47 (d (br), 1H, J=50.8 Hz), 5.10 (d, 1H, J=8.8 Hz), 4.92–4.59 (m, 3H), 4.15–3.91 (m, 2H), 2.71–2.43 (m, 2H), 1.77 (s, 3H), 1.60 (s, 3H) ppm.

Example 23

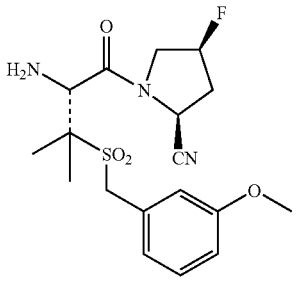

(2S,4S)-1-{(2R)-2-amino-3-[(3-methoxybenzyl)sulfonyl]-3-methylbutanoyl}-4-fluoropyrrolidine-2-carbonitrile hydrochloride A. (2R)-2-[(tert-butoxycarbonyl)amino]-3-[(3-methoxybenzyl)thio]-3-methylbutanoic acid.

To a 1.0 N KOH solution (50 mL) containing (2R)-2-[(tert-butoxycarbonyl)amino]-3-mercapto-3-methylbutanoic acid (1 g, 0.00401 mole) was added 3-methoxybenzyl chloride (691 mg, 0.00441 mole) at RT. After 17.0 hours the reaction mixture was diluted with water (50 mL) and washed with diethyl ether. The organics were discarded and the aqueous layer was cooled to 0–5° C. The aqueous layer was made acidic (pH 3.5) using concentrated HCl and extracted into EtOAc. The organics were dried over MgSO$_4$ and concentrated to dryness to yield a total of 1.35 g (91%) of compound A.

$^1$H NMR (CDCl$_3$) 400 MHz δ 7.19 (dd, 1H, J=7.8 Hz), 6.90 (d, 1H, J=7.2 Hz), 6.86 (s, 1H), 6.76 (dd, 1H, J=8.4 Hz), 5.43 (d (br), 1H, J=6.4 Hz), 4.39 (d (br), 1H, J=6.8 Hz), 3.82–3.74 (m, 5H), 1.45–1.35 (m, 15H) ppm.

B. Tert-butyl (1R)-1-{[(2S,4S)-2-cyano-4-fluoropyrrolidin-1-yl]carbonyl}-2-[(3-methoxybenzyl)thio]-2-methyl propylcarbamate.

To a DMF solution (25 ml) containing compound A (1.3 g, 0.0035 mole) and N,N-diisopropylethylamine (1.36 g, 0.0106 mole) was added HATU (2.0 g, 0.0053 mole) at RT. After 30 minutes the reaction mixture was mixed with (2S,4S)-4-fluoro-2-pyrrolidinecarbonitrile 4-methylbenzenesulfonate (1.1 g, 0.0038 mole). After stirring overnight the reaction was quenched with NaHCO$_3$ and the organics extracted with EtOAc (2×). The organics were washed with sat. NaCl and dried over MgSO$_4$. Removal of the solvent in vacuo and purification via column chromatography (1/1 hexanes/EtOAc) yielded 617 mg (38%) of compound B.

$^1$H NMR (CDCl$_3$) 400 MHz δ 7.18 (dd, 1H, J=7.8 Hz), 6.95 (s, 1H,), 6.92 (d (br), 1H, J=2.8), 6.74 (dd, 1H, J=8.2 Hz), 5.41 (d (br), 1H, J=8.8 Hz), 5.39 (d (br), 1H, J=51.2), 5.00 (d, 1H, J=9.6 Hz), 4.35 (d, 1H, J=8.8 Hz), 4.28–3.78 (m, 7H), 2.71–2.52 (m, 1H), 2.46–2.27 (m, 1H), 1.62–1.39 (m, 15H) ppm.

C. Tert-butyl (1R)-1-{[(2S,4S)-2-cyano-4-fluoropyrrolidin-1-yl]carbonyl}-2-[(3-methoxybenzyl)sulfonyl]-2-methylpropylcarbamate.

To a CH$_2$Cl$_2$ solution (100 mL) containing compound B (617 mg, 0.0013 mole) was added 3-chloroperoxybenzoic acid (57–86%) (2.3 g 0.013 mole). The reaction mixture was allowed to stir at RT for a period of 16.0 hours followed by neutralization with 2.0 N KOH. The organics were dried over MgSO$_4$ and concentrated to dryness to afford 647 mg of crude solid (98%). The resulting off white solid was used without further purification.

$^1$H NMR (CDCl$_3$) 400 MHz δ 7.30–7.25 (m, 1H), 7.01–6.98 (m, 2H,), 6.92–6.88 (m, 1H), 5.49 (d (br), 1H, J=8.4 Hz), 5.39 (d (br), 1H, J=50.8 Hz), 5.03 (d (br), 1H, J=9.2), 4.96 (d, 1H, J=9.2 Hz), 4.32–3.80 (m, 4H), 3.79 (s, 3H), 2.71–2.54 (m, 1H), 2.46–2.24 (m, 1H), 1.59–1.39 (m, 15H) ppm.

D. (2S,4S)-1-{(2R)-2-Amino-3-[(3-methoxybenzyl)sulfonyl]-3-methylbutanoyl}-4-fluoropyrrolidine-2-carbonitrile hydrochloride.

To a CH$_2$Cl$_2$ solution (45 mL) containing compound C (647 mg, 0.0013 mole) was added TFA (5 mL). The reaction mixture was allowed to stir at RT for a period of 16.0 hours followed by neutralization with sat NaHCO$_3$. The organics were separated, dried over MgSO$_4$ and concentrated to dryness to afford a crude solid. The resulting solid was purified using silica gel chromatography (99% CH$_2$Cl$_2$/1% MeOH with 2.0M NH$_3$). The pure solid was dissolved into an acetone/ether mixture (1/1) and precipitated using 2.0 N HCl in ether. The resulting solid was filtered in vacuo and washed with ether. After drying under high vacuum the reaction yielded a total of 221 mg of compound D.

$^1$H NMR (d$_4$-MeOH) 400 MHz δ 7.31 (dd, 1H, J=8.0 Hz), 7.18–7.06 (m, 2H), 6.98 (d, 1H, J=8.0 Hz), 5.49 (d (br), 1H, J=50.8 Hz), 5.10 (d, 1H, J=9.2 Hz), 4.72–4.58 (m, 3H), 4.15–3.88 (m, 2H), 3.81 (s, 3H), 2.69–2.44 (m, 2H), 1.75 (s, 3H), 1.59 (s, 3H) ppm.

Example 24

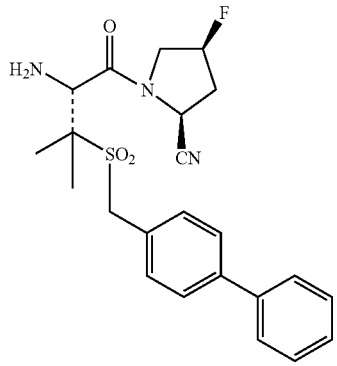

(2S,4S)-1-{(2R)-2-Amino-3-[(1,1'-biphenyl-4-yl methyl)sulfonyl]-3-methylbutanoyl}-4-fluoropyrrolidine-2-carbonitrile hydrochloride A. 2R)-3-[(1,1'-Biphenyl-4-yl methyl)thio]-2-[(tert-butoxycarbonyl)amino]-3-methylbutanoic acid.

To a 1.0 N KOH solution (50 mL) containing 1,4-dioxane (10 mL), and (2R)-2-[(tert-butoxycarbonyl)amino]-3-mercapto-3-methylbutanoic acid (1 g, 0.00401 mole) was added 4-phenylbenzyl chloride (894 mg, 0.00441 mole) at RT. After 17.0 hours the reaction mixture was diluted with water and washed with diethyl ether. The organics were discarded and the aqueous layer was cooled to 0–5° C. The aqueous solution was made acidic (pH 3.5) using concentrated HCl and the product was extracted into ether. The organics were dried over MgSO$_4$ and concentrated to dryness to yield a total of 1.4 g (82%) of compound A as a white solid.

$^1$H NMR (CDCl$_3$) 400 MHz δ 7.59–7.31 (m, 9H), 5.49 (m, 1H), 4.32 (d (br), 1H, J=9.6 Hz), 3.88–3.71 (m, 2H), 1.57–1.40 (m, 15H) ppm.

B. Tert-butyl (1R)-2-[(1,1'-biphenyl-4-ylmethyl)thio]-1-{[(2S,4S)-2-cyano-4-fluoropyrrolidin-1-yl]carbonyl}-2-methylpropylcarbamate.

To a DMF solution (25 mL) containing compound A (1.4 g, 0.0034 mole) and N,N-diisopropylethylamine (1.3 g, 0.0101 mole) was added HATU (1.9 g, 0.0051 mole) at RT. After 30 minutes the reaction mixture was mixed with (2S, 4S)-4-fluoro-2-pyrrolidinecarbonitrile 4-methylbenzenesulfonate (1.1 g, 0.0037 mole). After stirring overnight the reaction was quenched with NaHCO$_3$ and the organics extracted with EtOAc (2×). The organics were washed with sat. NaCl and dried over MgSO$_4$. Removal of the solvent in vacuo and purification via column chromatography (1/1 hexanes/EtOAc) yielded 828 mg (48% yield) of extremely pure product.

$^1$H NMR (CDCl$_3$) 400 MHz δ 7.57–7.30 (m, 9H), 5.47–5.33 (m, 2H), 5.03 (d(br), 1H, J=9.6), 4.39 (d, 1H, J=8.8 Hz), 4.31–3.97 (m, 2H), 3.89 (s, 2H), 2.68 (dd, 1H, J=15.6 Hz), 2.44–2.28 (m, 1H), 1.58–1.41 (m, 15H) ppm.

C. Tert-butyl (1R)-2-[(1,1'-biphenyl-4-ylmethyl)sulfonyl]-1-{[(2S,4S)-2-cyano-4-fluoropyrrolidin-1-yl]carbonyl}-2-methyl propylcarbamate.

To a CH$_2$Cl$_2$ solution (100 mL) containing compound B (828 mg, 0.0016 mole) was added 3-chloroperoxybenzoic acid(57–86%) (2.8 g 0.0162 mole). The reaction mixture was allowed to stir at RT for a period of 16.0 hours followed by neutralization with 2.0 N KOH. The organics were dried over MgSO$_4$ and concentrated to dryness to afford 867 mg of compound C (99% yield). The resulting white solid was used without further purification.

$^1$H NMR (CDCl$_3$) 400 MHz δ 7.63–7.33 (m, 9H), 5.53 (d(br), 1H, J=8.4 Hz), 5.42 (d(br), 1H, J=50.8 Hz), 5.07 (d(br), 1H, J=9.2), 4.99 (d, 1H, J=9.2 Hz), 4.39–4.00 (m, 4H), 2.70 (dd, 1H, J=15.2 Hz), 2.47–2.34 (m, 1H), 1.62–1.40 (m, 15H) ppm.

D. (2S,4S)-1-{(2R)-2-amino-3-[(1,1'-biphenyl-4-ylmethyl)sulfonyl]-3-methylbutanoyl}-4-fluoropyrrolidine-2-carbonitrile hydrochloride.

To a CH$_2$Cl$_2$ solution (45 mL) containing compound C (867 mg, 0.0016 mole) was added TFA (5 mL). The reaction mixture was allowed to stir at RT for a period of 16.0 hours followed by neutralization with sat. NaHCO$_3$. The organics were separated, dried over MgSO$_4$ and concentrated to dryness to afford a crude solid. The resulting solid was purified using silica gel chromatography (99% CH$_2$Cl$_2$/1% MeOH with 2.0M NH$_3$). The pure solid was dissolved into an acetone/ether mixture (1/1) and precipitated using 2.0 N HCl in ether. The resulting solid was filtered in vacuo and washed with ether. After drying under high vacuum the reaction yielded a total of 307 mg of compound D.

$^1$H NMR (d$_4$-MeOH) 400 MHz δ 7.66–7.32 (m, 9H), 5.48 (d(br), 1H, J=50.4 Hz), 5.10 (d, 1H, J=8.0), 4.86–4.64 (m, 3H), 4.19–3.86 (m, 2H), 2.70–2.41 (m, 2H), 1.78 (s, 3H), 1.63 (s, 3H) ppm.

Example 25

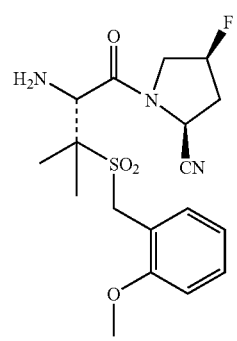

(2S,4S)-1-{(2R)-2-Amino-3-[(2-methoxybenzyl)sulfonyl]-3-methylbutanoyl}-4-fluoropyrrolidine-2-carbonitrile hydrochloride A. (2R)-2-[(Tert-butoxycarbonyl)amino]-3-[(2-methoxybenzyl)thio]-3-methylbutanoic acid.

To a 1.0 N KOH solution (50 mL) containing (2R)-2-[(tert-butoxycarbonyl)amino]-3-mercapto-3-methylbutanoic acid (1 g, 0.00401 mole) was added 2-methoxybenzyl chloride (691 mg, 0.00441 mole) at RT. After 17.0 hours the reaction mixture was diluted with water and washed with diethyl ether. The organics were discarded and the aqueous layer was cooled to 0–5° C. The aqueous solution was made acidic (pH 3.5) using concentrated HCl and the product was extracted into EtOAc. The organics were dried over MgSO$_4$ and concentrated to dryness to yield a total of 1.1 g (74%) of compound A.

$^1$H NMR (CDCl$_3$) 400 MHz δ 7.25–7.21 (m, 2H), 6.90–6.85 (m, 2H), 5.63–5.55 (m, 1H), 4.31 (d(br), 1H, J=9.2 Hz), 3.88–3.79 (m, 5H), 1.58–1.33 (m, 15H) ppm.

B. Tert-butyl (1R)-1-{[(2S,4S)-2-cyano-4-fluoropyrrolidin-1-yl]carbonyl}-2-[(2-methoxybenzyl)thio]-2-methylpropylcarbamate.

To a DMF solution (25 mL) containing compound A (1.0 g, 0.0027 mole) and N,N-diisopropylethylamine (1.05 g, 0.0081 mole) was added HATU (1.5 g, 0.00405 mole) at RT. After 30 minutes the reaction mixture was mixed with (2S, 4S)-4-fluoro-2-pyrrolidinecarbonitrile 4-methylbenzenesulfonate (851 mg, 0.003 mole). After stirring overnight the reaction was quenched with NaHCO$_3$ and the organics extracted with EtOAc (2×). The organics were washed with sat. NaCl and dried over MgSO$_4$. Removal of the solvent in vacuo and purification via column chromatography (1/1 hexanes/EtOAc) yielded 668 mg (53% yield) of compound B.

$^1$H NMR (CDCl$_3$) 400 MHz δ 7.31 (dd, 1H, J=7.6 Hz), 7.19 (dd, 1H, J=8.0 Hz), 6.92–6.83 (m, 2H), 5.47–5.31 (m, 2H), 5.03 (d(br), 1H, J=9.2) 4.34 (d, 1H, J=8.4 Hz), 4.26–3.66 (m, 7H), 2.68 (dd, 1H, J=15.2 Hz), 2.43–2.26 (m, 1H), 1.57–1.37 (m, 15H) ppm.

C. Tert-butyl (1R)-1-{[(2S,4S)-2-cyano-4-fluoropyrrolidin-1-yl]carbonyl}-2-[(2-methoxybenzyl)sulfonyl]-2-methylpropylcarbamate.

To a CH$_2$Cl$_2$ solution (75 mL) containing compound B (668 mg, 0.0014 mole) was added 3-chloroperoxybenzoic acid(57–86% o) (2.5 g 0.0140 mole). The reaction mixture was allowed to stir at RT for a period of 16.0 hours followed by neutralization with 2.0 N KOH. The organics were dried over MgSO$_4$ and concentrated to dryness to afford 678 mg of compound C (95%). The resulting off white solid was used without further purification.

$^1$H NMR (CDCl$_3$) 400 MHz δ 7.44 (dd, 1H, J=7.6 Hz), 7.34 (m, 1H), 6.99–6.91 (m, 2H), 5.61–5.57 (m, 1H), 5.40 (d(br), 1H, J=51.2 Hz), 5.00–4.95 (m, 2H), 4.49–3.85 (m, 7H), 2.65 (dd, 1H, J=15.6 Hz), 2.45–2.28 (m, 1H), 1.62–1.37 (m, 15H) ppm.

D. (2S,4S)-1-{(2R)-2-amino-3-[(2-methoxybenzyl)sulfonyl]-3-methylbutanoyl}-4-fluoropyrrolidine-2-carbonitrile hydrochloride.

To a CH$_2$Cl$_2$ solution (45 mL) containing compound C (678 mg, 0.00136 mole) was added TFA (5 mL). The reaction mixture was allowed to stir at RT for a period of 16.0 hours followed by neutralization with sat. NaHCO$_3$. The organics were separated, dried over MgSO$_4$ and concentrated to dryness to afford a crude solid. The resulting solid was purified using silica gel chromatography (99% CH$_2$Cl$_2$/1% MeOH with 2.0 M NH$_3$). The pure solid was dissolved into an acetone/ether mixture (1/1) and precipitated using 2.0 N HCl in ether. The resulting solid was filtered in vacuo and washed with ether. After drying under high vacuum the reaction yielded a total of 313 mg of compound D.

$^1$H NMR (d$_4$-MeOH) 400 MHz δ 7.45–7.38 (m, 2H), 7.06 (d, 1H, J=8.4 Hz), 6.99–6.99 (dd, 1H, J=7.2 Hz), 5.49 (d(br), 1H, J=50.8 Hz), 5.09 (m, 1H, J=9.2), 4.13–3.84 (m, 6H), 2.67–2.44 (m, 2H), 1.74 (s, 3H), 1.58 (s, 3H) ppm.

Example 26

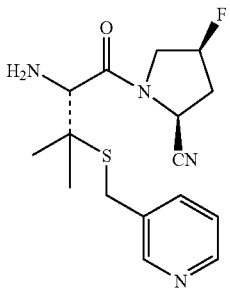

(2S,4S)-1-{(2R)-2-Amino-3-methyl-3-[(pyridin-3-yl methyl)thio]butanoyl}-4-fluoropyrrolidine-2-carbonitrile A. (2R)-2-[(Tert-butoxycarbonyl)amino]-3-methyl-3-[(pyridin-3-ylmethyl)thio]butanoic acid.

To a 1.0 N KOH solution (50 mL) containing (2R)-2-[(tert-butoxycarbonyl)amino]-3-mercapto-3-methylbutanoic acid (1 g, 0.00401 mole) was added 3-(bromomethyl) pyridine hydrobromide (1.1 g, 0.00441 mole) at RT. After 17.0 hours the reaction mixture was diluted with water and washed with diethyl ether. The organics were discarded and the aqueous layer was cooled to 0–5° C. The aqueous solution was made acidic (pH 4.0) using concentrated HCl and the product was extracted into EtOAc. The organics were dried over Na$_2$SO$_4$ and concentrated to dryness to yield a total of 403 mg (30%) of compound A as a pure oily solid.

$^1$H NMR (CDCl$_3$) 400 MHz δ 8.77 (s, 1H), 8.56 (d, 1H, J=5.6 Hz), 7.80 (d, 1H, J=8.0 Hz), 7.37 (dd, 1H, J=8.0 Hz), 5.47 (d(br), 1H, J=9.6 Hz), 4.53 (d(br), 1H, J=9.6 Hz), 3.95 (dd, 2H, J=69.6 Hz), 1.60–1.35 (m, 15H) ppm.

B. Tert-butyl (1R)-1-{[(2S,4S)-2-cyano-4-fluoropyrrolidin-1-yl]carbonyl}-2-methyl-2-[(pyridin-3-ylmethyl)thio]propylcarbamate.

To a DMF solution (20 mL) containing compound A (400 mg, 0.0012 mole) and N,N-diisopropylethylamine (456 mg, 0.0035 mole) was added HATU (670 mg, 0.0018 mole) at RT. After 30 minutes the reaction mixture was mixed with (2S, 4S)-4-fluoro-2-pyrrolidinecarbonitrile 4-methylbenzenesulfonate (370 mg, 0.0013 mole). After stirring overnight the reaction was quenched with NaHCO$_3$ and the organics extracted with EtOAc (2x). The organics were washed with sat. NaCl and dried over Na$_2$SO$_4$. Removal of the solvent in vacuo and purification via column chromatography (1/1 hexanes/EtOAc) yielded 314 mg (61%) of compound B.

$^1$H NMR (CDCl$_3$) 400 MHz δ 8.58 (s, 1H), 8.46 (d, 1H, J=4.8 Hz), 7.71 (d, 1H, J=8.0 Hz), 7.21 (dd, 1H, J=8.0 Hz), 5.45 (d(br), 1H, J=9.2 Hz), 5.43 (d(br), 1H, J=51.2 Hz), 5.02 (d, 1H, J=9.2 Hz), 4.41 (d, 1H, J=9.6 Hz), 4.37–3.79 (m, 4H), 2.70 (dd, 1H, J=15.6 Hz), 2.46–2.29 (m, 1H), 1.55–1.39 (m, 15H) ppm.

C. (2S,4S)-1-{(2R)-2-Amino-3-methyl-3-[(pyridin-3-ylmethyl)thio]butanoyl}-4-fluoropyrrolidine-2-carbonitrile hydrochloride.

To a CH$_2$Cl$_2$ solution (22 mL) containing compound B (314 mg, 0.720 mmol) was added TFA (3 mL). The reaction mixture was allowed to stir at RT for a period of 16.0 hours followed by neutralization with sat. NaHCO$_3$. The organics were separated, dried over Na$_2$SO$_4$ and concentrated to dryness to afford a crude solid. The resulting solid was purified using silica gel chromatography (99% CH$_2$Cl$_2$/1% MeOH with 2.0 M NH$_3$). The pure solid was dissolved into an acetone/ether mixture (1/1) and precipitated using 2.0 N HCl in ether. The resulting solid was filtered in vacuo and washed with ether. After drying under high vacuum the reaction yielded a total of 69 mg of compound C.

$^1$H NMR (CDCl$_3$) 400 MHz δ 8.57 (s, 1H), 8.46 (d, 1H, J=5.2 Hz), 7.71 (d, 1H, J=6.4 Hz), 7.23 (dd, 1H, J=8.0 Hz), 5.44 (d(br), 1H, J=51.2 Hz), 4.97 (d, 1H, J=9.6 Hz), 4.20–3.58 (m, 5H), 2.66 (dd, 1H, J=15.2 Hz), 2.39–2.22 (m, 1H), 1.78 (s(br), 2H), 1.48 (s, 3H), 1.39 (s, 3H) ppm.

Example 27

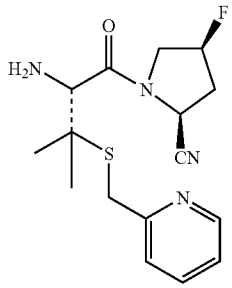

(2S,4S)-1-{(2R)-2-Amino-3-methyl-3-[(pyridin-2-ylmethyl)thio]butanoyl}-4-fluoropyrrolidine-2-carbonitrile hydrochloride A. (2R)-2-[(Tert-butoxycarbonyl)amino]-3-methyl-3-[(pyridin-2-ylmethyl)thio]butanoic acid.

To a 1.0 N KOH solution (50 mL) containing (2R)-2-[(tert-butoxycarbonyl)amino]-3-mercapto-3-methylbutanoic acid (1 g, 0.00401 mole) was added 2-(bromomethyl)pyridine hydrobromide (1.1 g, 0.00441 mole) at RT. After 17.0 hours the reaction mixture was diluted with water and washed with diethyl ether. The organics were discarded and the aqueous layer was cooled to 0–5° C. The aqueous solution was made acidic (pH 4.0) using concentrated HCl and the product was extracted into EtoAc. The organics were dried over $Na_2SO_4$ and concentrated to dryness to yield a total of 557 mg (41%) of compound A as a white solid.

$^1$H NMR (CDCl$_3$) 400 MHz δ 8.53 (d, 1H, J=4.8 Hz), 7.75 (dd, 1H, J=7.6 Hz), 7.34–7.30 (m, 2H), 5.73 (d(br), 1H, J=8.8 Hz), 4.47 (d, 1H, J=8.8 Hz), 4.41–4.01 (m, 2H) 1.55 (m, 15H) ppm.

B. Tert-butyl (1R)-1-{[(2S,4S)-2-cyano-4-fluoropyrrolidin-1-yl]carbonyl}-2-methyl-2-[(pyridin-2-ylmethyl)thio]propylcarbamate.

To a DMF solution (20 mL) containing compound A (557 mg, 0.0016 mole) and N,N-diisopropylethylamine (635 mg, 0.0049 mole) was added HATU (912 mg, 0.0024 mole) at RT. After 30 minutes the reaction mixture was mixed with (2S, 4S)-4-fluoro-2-pyrrolidinecarbonitrile 4-methylbenzenesulfonate (504 mg, 0.00176 mole). After stirring overnight the reaction was quenched with NaHCO$_3$ and the organics extracted with EtOAc (2×). The organics were washed with sat. NaCl and dried over Na$_2$SO$_4$. Removal of the solvent in vacuo and purification via column chromatography (1/1 hexanes/EtOAc) yielded 466 mg (65%) of compound B.

$^1$H NMR (d$_6$ Acetone) 400 MHz δ 8.46 (d, 1H, J=4.4 Hz), 7.71 (dd, 1H, J=7.6 Hz), 7.48 (d, 1H, J=8.0 Hz), 7.21 (dd, 1H, J=7.6 Hz), 6.25 (d(br), 1H, J=8.4 Hz), 5.60 (d(br), 1H, J=50.8 Hz), 5.05 (m, 1H), 4.61 (d, 1H J=8.8 Hz), 4.43–3.83 (m, 4H), 2.83–2.52 (m, 2H), 1.50–1.35 (m, 15H) ppm.

C. (2S,4S)-1-{(2R)-2-Amino-3-methyl-3-[(pyridin-2-yl methyl)thio]butanoyl}-4-fluoropyrrolidine-2-carbonitrile hydrochloride.

To a CH$_2$Cl$_2$ solution (45 mL) containing compound B (314 mg, 0.00107 mol) was added TFA (5 mL). The reaction mixture was allowed to stir at RT for a period of 16.0 hours followed by neutralization with sat NaHCO$_3$. The organics were separated, dried over Na$_2$SO$_4$ and concentrated to dryness to afford a crude solid. The resulting solid was purified using silica gel chromatography (99% CH$_2$Cl$_2$/1% MeOH with 2.0 M NH$_3$). The pure solid was dissolved into an acetone/ether mixture (1/1) and precipitated using 2.0 N HCl in ether. The resulting solid was filtered in vacuo and washed with ether. After drying under high vacuum the reaction yielded a total of 127 mg of compound C.

$^1$H NMR (D$_2$O) 400 MHz δ 8.54 (d, 1H, J=5.6 Hz), 8.34 (dd, 1H, J=8.0 Hz), 7.92 (d, 1H, J=8.4 Hz), 7.21 (dd, 1H, J=6.4 Hz), 5.44 (d(br), 1H, J=50.4 Hz), 5.02 (d, 1H, J=10 Hz), 4.60 (m, 5H), 2.62 (dd, 1H, J=15.6 Hz), 2.54–2.34 (m, 1H), 1.40 (s, 6H) ppm.

Example 28

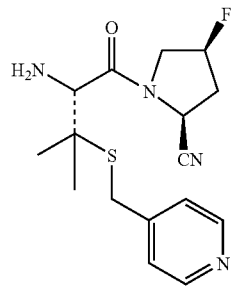

(2S,4S)-1-{(2R)-2-amino-3-methyl-3-[(pyridin-4-ylmethyl)thio]butanoyl}-4-fluoropyrrolidine-2-carbonitrile hydrochloride A. (2R)-2-[(tert-butoxycarbonyl)amino]-3-methyl-3-[(pyridin-4-ylmethyl)thio]butanoic acid.

To a 1.0 N KOH solution (50 mL) containing (2R)-2-[(tert-butoxycarbonyl)amino]-3-mercapto-3-methylbutanoic acid (1 g, 0.00401 mole) was added 4-(bromomethyl)pyridine hydrobromide (1.1 g, 0.00441 mole) at RT. After 17.0 hours the reaction mixture was diluted with water and washed with diethyl ether. The organics were discarded and the aqueous layer was cooled to 0–5° C. The aqueous solution was made acidic (pH 4.0) using concentrated HCl and the product was extracted into EtOAc. The organics were dried over Na$_2$SO$_4$ and concentrated to dryness to yield a total of 482 mg (35%) of compound A as a white solid.

$^1$H NMR (CDCl$_3$) 400 MHz δ 8.48 (d, 2H, J=6.0 Hz), 7.40 (d, 2H, J=5.6 Hz), 5.48 (d(br), 1H, J=9.2 Hz), 4.41 (d. 1H, J=9.2 Hz), 3.82 (s, 2H) 1.52–1.38 (m, 15H) ppm.

B. Tert-butyl (1R)-1-{[(2S,4S)-2-cyano-4-fluoropyrrolidin-1-yl]carbonyl}-2-methyl-2-[(pyridin-4-ylmethyl)thio]propylcarbamate.

To a DMF solution (20 mL) containing compound A (482 mg, 0.00142 mole) and N,N-diisopropylethylamine (549 mg, 0.0042 mole) was added HATU (810 mg, 0.00213 mole) at RT. After 30 minutes the reaction mixture was mixed with (2S, 4S)-4-fluoro-2-pyrrolidinecarbonitrile 4-methylbenzenesulfonate (447 mg, 0.00156 mole). After stirring overnight the reaction was quenched with NaHCO$_3$ and the organics extracted with EtOAc (2×). The organics were washed with sat NaCl and dried over Na$_2$SO$_4$. Removal of the solvent in vacuo and purification via column chromatography (1/1 hexanes/EtOAc) yielded 476 mg (77%) of compound B.

$^1$H NMR (CDCl$_3$) 400 MHz δ 8.51 (d, 2H, J=4.4 Hz), 7.31 (d, 2H, J=6.4 Hz), 5.43 (d(br), 1H, J=9.6 Hz), 5.43 (d(br), 1H, J=51.2 Hz), 5.01 (d, 1H, J=9.6 Hz), 4.39 (d, 1H, J=9.6 Hz), 4.35–3.96 (m, 2H), 3.80 (s, 2H), 2.70 (dd, 1H, J=15.4), 2.46–2.29 (m, 1H), 1.45–1.41 (m, 15H) ppm.

C. (2S,4S)-1-{(2R)-2-amino-3-methyl-3-[(pyridin-4-yl methyl)thio]butanoyl}-4-fluoropyrrolidine-2-carbonitrile hydrochloride.

To a CH$_2$Cl$_2$ solution (45 mL) containing compound B (476 mg, 0.00109 mol) was added TFA (5 mL). The reaction mixture was allowed to stir at RT for a period of 16.0 hours followed by neutralization with sat. NaHCO$_3$. The organics were separated, dried over Na$_2$SO$_4$ and concentrated to dryness to afford a crude solid. The resulting solid was purified using silica gel chromatography (99% CH₂Cl₂/1% MeOH with 2.0 M NH₃). The pure solid was dissolved into an acetone/ether mixture (1/1) and precipitated using 2.0 N HCl in ether. The resulting solid was filtered in vacuo and washed with ether. After drying under high vacuum the reaction yielded a total of 107 mg of compound C.

$^1$H NMR (d₄-MeOH) 400 MHz δ 8.81 (d, 2H, J=4.8 Hz), 8.08 (d, 2H, J=6.4 Hz), 5.51 (d(br), 1H, J=51.2 Hz), 5.10 (d, 1H, J=9.2 Hz), 4.35–3.96 (m, 4H), 2.65–2.43 (m, 2H), 1.62–1.42 (m, 6H) ppm.

Example 29

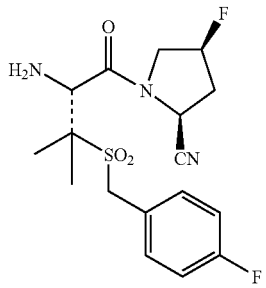

(2S,4S)-1-{(2R)-2-amino-3-[(4-fluorobenzyl)sulfonyl]-3-methylbutanoyl}-4-fluoropyrrolidine-2-carbonitrile hydrochloride A. (2R)-2-[(tert-butoxycarbonyl)amino]-3-[(4-fluorobenzyl)thio]-3-methylbutanoic acid. To a 1.0 N KOH solution (50 mL) containing (2R)-2-[(tert-butoxycarbonyl)amino]-3-mercapto-3-methylbutanoic acid (1.0 g, 0.00401 mole) was added 1-(bromomethyl)-4-fluorobenzene (834 mg, 0.00441 mole) at RT. After 17.0 hours the reaction mixture was diluted with water and washed with ether. The organics were discarded and the aqueous layer was cooled to 0–5° C. The aqueous solution was made acidic (pH 3.5) using concentrated HCl and the product was extracted into EtOAc. The organics were dried over MgSO₄ and concentrated to dryness to yield a total of 1.2 g (8601%) of compound A as an oil.

$^1$H NMR (CDCl₃) 400 MHz δ 7.29–7.26 (m, 2H), 6.99–6.94 (m, 2H), 5.40 (d(br), 1H, J=8.0 Hz), 4.40 (d(br), 1H, J=8.0 Hz), 3.80–3.74 (m, 2H) 1.50–1.40 (m, 15H) ppm.

B. Tert-butyl (1R)-1-{[(2S,4S)-2-cyano-4-fluoropyrrolidin-1-yl]carbonyl}-2-[(4-fluorobenzyl)thio]-2-methylpropylcarbamate.

To a DMF solution (25 mL) containing compound A (1.2 g, 0.0034 mole) and N,N-diisopropylethylamine (1.3 g, 0.0101 mole) was added HATU (1.9 g, 0.0051 mole) at RT. After 30 minutes the reaction mixture was mixed with (2S, 4S)-4-fluoro-2-pyrrolidinecarbonitrile 4-methylbenzenesulfonate (1.1 g, 0.0037 mole). After stirring overnight the reaction was quenched with NaHCO₃ and the organics extracted with EtOAc (2×). The organics were washed with sat NaCl and dried over Na₂SO₄. Removal of the solvent in vacuo and purification via column chromatography (1/1 hexanes/EtOAc) yielded 929 mg (61% yield) of compound B.

$^1$H NMR (CDCl₃) 400 MHz δ 7.33 (dd, 2H, J=8.4 Hz), 6.96 (dd, 2H, J=8.8 Hz), 5.42 (d(br), 1H, J=9.2 Hz), 5.43 (d(br), 1H, J=51.6 Hz), 5.02 (d, 1H, J=9.6 Hz), 4.38 (d, 1H, J=9.2 Hz), 4.34–3.97 (m, 2H), 3.82 (s, 2H), 2.69 (dd, 1H, J=15.4 Hz), 2.46–2.28 (m, 1H), 1.45–1.41 (m, 15H) ppm.

C. Tert-butyl (1R)-1-{[(2S,4S)-2-cyano-4-fluoropyrrolidin-1-yl]carbonyl}-2-[(4-fluorobenzyl)sulfonyl]-2-methylpropylcarbamate.

To a CH₂Cl₂ solution (100 mL) containing compound B (929 mg, 0.0019 mole) was added 3-chloroperoxybenzoic acid (57–86%) (3.3 g 0.0191 mole). The reaction mixture was allowed to stir at RT for a period of 16.0 hours followed by neutralization with 2.0 N KOH. The organics were dried over MgSO₄ and concentrated to dryness to afford 678 mg of compound C (97% yield). The resulting off white solid was used without further purification.

$^1$H NMR (CDCl₃) 400 MHz δ 7.40 (dd, 2H, J=8.8 Hz), 7.07 (dd, 2H, J=8.6 Hz), 5.52 (d(br), 1H, J=9.2 Hz), 5.43 (d(br), 1H, J=51.2 Hz), 5.03 (d, 1H, J=9.6 Hz), 4.97 (d, 1H, J=9.6 Hz), 4.36–3.74 (m, 4H), 2.70 (dd, 1H, J=15.2 Hz), 2.47–2.28 (m, 1H), 1.72–1.35 (m, 15H) ppm.

D. (2S,4S)-1-{(2R)-2-Amino-3-[(4-fluorobenzyl)sulfonyl]-3-methylbutanoyl}-4-fluoropyrrolidine-2-carbonitrile hydrochloride.

To a CH₂Cl₂ solution (45 mL) containing compound C (678 mg, 0.00140 mole) was added TFA (5 mL). The reaction mixture was allowed to stir at RT for a period of 16.0 hours followed by neutralization with sat NaHCO₃. The organics were separated, dried over MgSO₄ and concentrated to dryness to afford a crude solid. The resulting solid was purified using silica gel chromatography (99% CH₂Cl₂/1% MeOH with 2.0 M NH₃). The pure solid was dissolved into an acetone/ether mixture (1/1) and precipitated using 2.0 N HCl in ether. The resulting solid was filtered in vacuo and washed with ether. After drying under high vacuum the reaction yielded a total of 254 mg of compound D as a white solid.

$^1$H NMR (CDCl₃) 400 MHz δ 7.39 (dd, 2H, J=8.4 Hz), 7.08 (dd, 2H, J=8.6 Hz), 5.41 (d(br), 1H, J=50.8 Hz), 4.94 (d, 1H, J=9.6 Hz), 4.63 (d, 1H, J=13.2 Hz), 4.35–3.55 (m, 4H), 2.70 (dd, 1H, J=15.4 Hz), 2.43–2.26 (m, 1H), 1.80–1.39 (m, 8H) ppm.

Example 30

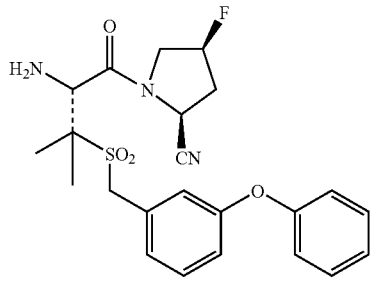

(2S,4S)-1-{(2R)-2-amino-3-methyl-3-[(3-phenoxybenzyl)sulfonyl]butanoyl}-4-fluoropyrrolidine-2-carbonitrile hydrochloride A. (2R)-2-[(Tert-butoxycarbonyl)amino]-3-methyl-3-[(3-phenoxybenzyl)thio]butanoic acid.

To a 1.0 N KOH solution (50 mL) containing (2R)-2-[(tert-butoxycarbonyl)amino]-3-mercapto-3-methylbutanoic acid (1 g, 0.00401 mole) was added 1-(chloromethyl)-3-phenoxybenzene (964 mg, 0.00441 mole) and 1,4-dioxane (15 mL) at RT. After 17.0 hours the reaction mixture was diluted with water and washed with diethyl ether. The organics were discarded and the aqueous layer was cooled to 0–5° C. The aqueous solution was made acidic (pH 3.5) using concentrated HCl and the product was extracted into ether. The organics were dried over MgSO₄ and concentrated to dryness to yield a total of 1.4 g (82%) of compound A as a white solid.

¹H NMR (CDCl₃) 400 MHz δ 7.34–6.98 (m, 8H), 6.85 (dd, 1H, J=8.0 Hz), 5.44 (m, 1H), 4.38 (m, 1H), 3.80 (m, 2H), 1.50–1.40 (m, 15H) ppm.

B. Tert-butyl (1R)-1-{[(2S,4S)-2-cyano-4-fluoropyrrolidin-1-yl]carbonyl}-2-methyl-2-[(3-phenoxybenzyl)thio]propylcarbamate.

To a DMF solution (20 mL) containing compound A (1.4 g, 0.0032 mole) and N,N-diisopropylethylamine (1.3 g, 0.0100 mole) was added HATU (1.8 g, 0.0048 mole) at RT. After 30 minutes the reaction mixture was mixed with (2S, 4S)-4-fluoro-2-pyrrolidinecarbonitrile 4-methylbenzenesulfonate (1.0 g, 0.0035 mole). After stirring overnight the reaction was quenched with NaHCO₃ and the organics extracted with EtOAc (2×). The organics were washed with sat. NaCl and dried over MgSO₄. Removal of the solvent in vacuo and purification via column chromatography (ill hexanes/EtOAc) yielded 1.1 g (65% o) of compound B.

¹H NMR (CDCl₃) 400 MHz δ 7.34–6.97 (m, 8H), 6.84 (dd, 1H, J=8.0 Hz), 5.44 (d(br), 1H, J=9.2 Hz), 5.39 (d(br), 1H, J=51.2 Hz), 5.01 (d, 1H, J=9.6 Hz), 4.36 (d, 1H, J=9.2 Hz), 4.29–3.90 (m, 2H), 3.80 (s, 2H), 2.66 (dd, 1H, J=15.4 Hz), 2.43–2.26 (m, 1H), 1.52–1.38 (m, 15H) ppm.

C. Tert-butyl (1R)-1-{[(2S,4S)-2-cyano-4-fluoropyrrolidin-1-yl]carbonyl}-2-methyl-2-[(3-phenoxybenzyl)sulfonyl]propylcarbamate.

To a CH₂Cl₂ solution (50 mL) containing compound B (600 mg, 0.0011 mol) was added 3-chloroperoxybenzoic acid (57–86% o) (2.0 g 0.011 mole). The reaction mixture was allowed to stir at RT for a period of 16.0 hours followed by neutralization with 2.0 N KOH. The organics were dried over MgSO₄ and concentrated to dryness to afford 594 mg of compound C (93% yield). The resulting off white solid was used without further purification.

¹H NMR (CDCl₃) 400 MHz δ 7.34–7.00 (m, 9H), 5.40 (d(br), 1H, J=51.2 Hz), 5.27 (d(br), 1H, J=8.8 Hz), 4.93 (d, 1H, J=9.6 Hz), 4.62 (d, 1H, J=13.2 Hz), 4.46–3.55 (m, 4H), 2.69 (dd, 1H, J=15.4 Hz), 2.42–2.25 (m, 1H), 1.62–1.43 (m, 15H) ppm.

D. (2S,4S)-1-{(2R)-2-amino-3-methyl-3-[(3-phenoxybenzyl)sulfonyl]butanoyl}-4-fluoropyrrolidine-2-carbonitrile hydrochloride.

To a CH₂Cl₂ solution (45 mL) containing compound C (678 mg, 0.00106 mole) was added TFA (5 mL). The reaction mixture was allowed to stir at RT for a period of 16.0 hours followed by neutralization with sat. NaHCO₃. The organics were separated, dried over MgSO₄ and concentrated to dryness to afford a crude solid. The resulting solid was purified using silica gel chromatography (99% CH₂Cl₂/1% MeOH with 2.0 M NH₃). The pure solid was dissolved into an acetone/ether mixture (1/1) and precipitated using 2.0 N HCl in ether. The resulting solid was filtered in vacuo and washed with ether. After drying under high vacuum the reaction yielded a total of 268 mg of compound D as a white solid.

¹H NMR (d₆-DMSO) 400 MHz δ 7.42–6.99 (m, 9H), 5.54 (d(br), 1H, J=51.2 Hz), 5.04 (d, 1H, J=9.2 Hz), 4.70 (m, 2H), 4.46 (m, 1H), 4.16–3.79 (m, 2H), 2.55–2.30 (m, 2H), 1.55 (s, 3H), 1.47 (s, 3H) ppm.

Example 31

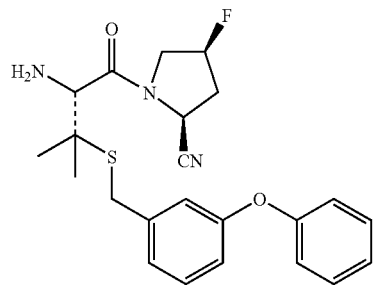

(2S,4S)-1-{(2R)-2-amino-3-methyl-3-[(3-phenoxybenzyl)thio]butanoyl}-4-fluoropyrrolidine-2-carbonitrile hydrochloride To a CH₂Cl₂ solution (45 mL) containing tert-butyl (1R)-1-{[(2S,4S)-2-cyano-4-fluoropyrrolidin-1-yl]carbonyl}-2-methyl-2-[(3-phenoxybenzyl)thio]propylcarbamate (500 mg, 0.0010 mol) was added TFA (5 mL). The reaction mixture was allowed to stir at RT for a period of 16.0 hours followed by neutralization with sat. NaHCO₃. The organics were separated, dried over MgSO₄ and concentrated to dryness to afford a crude solid. The resulting solid was purified using silica gel chromatography (99% CH₂Cl₂/1% MeOH with 2.0 M NH₃). The pure solid was dissolved into an acetone/ether mixture (1/1) and precipitated using 2.0 N HCl in ether. The resulting solid was filtered in vacuo and washed with ether. After drying under high vacuum the reaction yielded a total of 132 mg of the title compound.

¹H NMR (D₂O) 400 MHz δ 7.17–6.71 (m, 9H), 5.38 (d(br), 1H, J=50.4 Hz), 5.00 (d, 1H, J=9.6 Hz), 4.16–3.60 (m, 4H), 2.62–2.30 (m, 2H), 1.38–1.29 (s, 6H) ppm.

Example 32

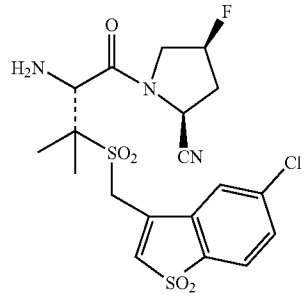

(2S,4S)-1-((2R)-2-Amino-3-{[(5-chloro-1,1-dioxido-1-benzothien-3-yl)methyl]sulfonyl}-3-methylbutanoyl)-4-fluoropyrrolidine-2-carbonitrile hydrochloride A. (2R)-2-[(tert-butoxycarbonyl)amino]-3-{[(5-chloro-1-benzothien-3-yl)methyl]thio}-3-methylbutanoic acid.

To a 1.0 N KOH solution (50 mL) containing (2R)-2-[(tert-butoxycarbonyl)amino]-3-mercapto-3-methylbutanoic acid (1 g, 0.00401 mole) was added 3-(bromomethyl)-5-chloro-1-benzothiophene (1.2 g, 0.00441 mole) and 1,4-dioxane (10 mL) at RT. After 17.0 hours the reaction mixture was diluted with water and washed with diethyl ether. The organics were discarded and the aqueous layer was cooled to 0–5° C. The aqueous solution was made acidic (pH 3.5) using concentrated HCl and the product was extracted into ether. The organics were dried over MgSO₄ and concentrated to dryness to yield a total of 1.0 g (59%) of compound A as a tan solid.

$^1$H NMR (CDCl₃) 400 MHz δ 7.84 (s, 1H), 7.72 (d, 1H, J=8.4 Hz), 7.39 (s, 1H), 7.30 (d, 1H, J=8.4 Hz), 5.44 (m, 1H), 4.45 (m, 1H, J=7.6 Hz), 4.07–4.00 (m, 2H), 1.55–1.40 (m, 15H) ppm.

B. Tert-butyl (1R)-2-{[(5-chloro-1-benzothien-3-yl)methyl]thio}-1-{[(2S,4S)-2-cyano-4-fluoropyrrolidin-1-yl]carbonyl}-2-methylpropylcarbamate.

To a DMF solution (20 mL) containing compound A (1.0 g, 0.0023 mole) and N,N-diisopropylethylamine (902 mg, 0.007 mole) was added HATU (1.3 g, 0.00345 mole) at RT. After 30 minutes the reaction mixture was mixed with (2S, 4S)-4-fluoro-2-pyrrolidinecarbonitrile 4-methylbenzenesulfonate (725 mg, 0.0025 mole). After stirring overnight the reaction was quenched with NaHCO₃ and the organics extracted with EtOAc (2×). The organics were washed with sat. NaCl and dried over MgSO₄. Removal of the solvent in vacuo and purification via column chromatography (1/1 hexanes/EtOAc) yielded 738 mg (60%) of compound B.

$^1$H NMR (CDCl₃) 400 MHz δ 7.91 (s, 1H), 7.72 (d, 1H, J=8.8 Hz), 7.47 (s, 1H), 7.30 (d, 1H, J=8.4 Hz), 5.49–5.35 (m, 2H), 5.04 (d, 1H, J=9.6 Hz), 4.41 (d, 1H, J=9.2 Hz), 4.35–3.98 (m, 4H), 2.69 (dd, 1H, J=15.2 Hz), 2.46–2.29 (m, 1H), 1.47–1.40 (m, 15H) ppm.

C. Tert-butyl (1R)-2-{[(5-chloro-1,1-dioxido-1-benzothien-3-yl)methyl]sulfonyl}-1-{[(2S,4S)-2-cyano-4-fluoropyrrolidin-1-yl]carbonyl}-2-methylpropylcarbamate.

To a CH₂Cl₂ solution (100 mL) containing compound B (738 mg, 0.0014 mole) was added 3-chloroperoxybenzoic acid (57–86%) (4.8 g 0.028 mole). The reaction mixture was allowed to stir at RT for a period of 16.0 hours followed by neutralization with 2.0 N KOH. The organics were dried over MgSO₄ and concentrated to dryness to afford 803 mg of compound C (97% yield). The resulting off white solid was used without further purification.

$^1$H NMR (CDCl₃) 400 MHz 8.05 (s, 1H), 7.96 (d, 1H, J=7.6 Hz), 7.48 (m, 3H), 5.45 (d(br), 1H J=10 Hz), 5.44 (d(br), 1H, J=50.8 Hz), 5.02 (d, 1H, J=10 Hz), 4.95 (d, 1H, J=9.6 Hz), 4.77–3.96 (m, 4H), 2.70 (dd, 1H, J=14.8 Hz), 2.46–2.30 (m, 1H), 1.70–1.37 (m, 15H) ppm.

D. (2S,4S)-1-((2R)-2-amino-3-{[(5-chloro-1,1-dioxido-1-benzothien-3-yl)methyl]sulfonyl}-3-methylbutanoyl)-4-fluoropyrrolidine-2-carbonitrile hydrochloride.

To a CH₂Cl₂ solution (45 mL) containing compound C (500 mg, 0.0010 mole) was added TFA (5 mL). The reaction mixture was allowed to stir at RT for a period of 16.0 hours followed by neutralization with sat. NaHCO₃. The organics were separated, dried over MgSO₄ and concentrated to dryness to afford a crude solid. The resulting solid was purified using silica gel chromatography (99% CH₂Cl₂/1% MeOH with 2.0 M NH₃). The pure solid was dissolved into an acetone/ether mixture (1/1) and precipitated using 2.0 N HCl in ether. The resulting solid was filtered in vacuo and washed with ether. After drying under high vacuum the reaction yielded a total of 132 mg of compound D.

$^1$H NMR (D₂O) 400 MHz δ 7.99 (s, 1H), 7.81–7.56 (m, 3H), 5.44 (d(br), 1H, J=50.4 Hz), 5.01 (d, 1H, J=9.6 Hz), 4.19–3.80 (m, 4H), 2.66–2.22 (m, 2H), 1.58 (s, 3H), 1.43 (s, 3H) ppm.

Example 33

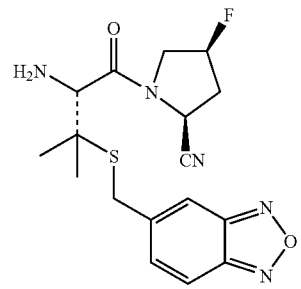

(2S,4S)-1-{(2R)-2-Amino-3-[(2,1,3-benzoxadiazol-5-yl methyl)thio]-3-methylbutanoyl}-4-fluoropyrrolidine-2-carbonitrile hydrochloride A. (2R)-3-[(2,1,3-Benzoxadiazol-5-ylmethyl)thio]-2-[(tert-butoxycarbonyl)amino]-3-methylbutanoic acid.

To a 1.0 N KOH solution (50 mL) containing (2R)-2-[(tert-butoxycarbonyl)amino]-3-mercapto-3-methylbutanoic acid (1 g, 0.00401 mole) was added 5-(bromomethyl)-2,1,3-benzoxadiazole (940 mg, 0.00441 mole) and 1,4-dioxane (5 mL) at RT. After 17.0 hours the reaction mixture was diluted with water and washed with diethyl ether. The organics were discarded and the aqueous layer was cooled to 0–5° C. The aqueous solution was made acidic (pH 4.0) using concentrated HCl and the product was extracted into EtOAc. The organics were dried over Na₂SO₄ and concentrated to dryness to yield a total of 622 mg (41%) of compound A as a brown solid.

$^1$H NMR (CDCl₃) 400 MHz δ 7.76 (d, 1H, J=9.2 Hz), 7.72 (s, 1H), 7.44 (d, 1H, J=9.2 Hz), 5.40 (d (br), 1H, J=8.0 Hz), 4.46 (d (br), 1H, J=8.4 Hz), 3.89 (s, 2H) 1.47–1.40 (m, 15H) ppm.

B. Tert-butyl (1R)-2-[(2,1,3-benzoxadiazol-5-yl methyl)thio]-1-{[(2S,4S)-2-cyano-4-fluoropyrrolidin-1-yl]carbonyl}-2-methylpropylcarbamate.

To a DMF solution (20 mL) containing compound A (622 mg, 0.00163 mole) and N,N-diisopropylethylamine (632 mg, 0.0049 mole) was added HATU (930 mg, 0.00244 mole) at RT. After 30 minutes the reaction mixture was mixed with (2S, 4S)-4-fluoro-2-pyrrolidinecarbonitrile 4-methylbenzenesulfonate (514 mg, 0.00180 mole). After stirring overnight the reaction was quenched with NaHCO₃ and the organics extracted with EtOAc (2×). The organics were washed with sat NaCl and dried over Na₂SO₄. Removal of the solvent in vacuo and purification via column chromatography (1/1 hexanes/EtOAc) yielded mg 444 mg (45% yield) of compound B.

$^1$H NMR (CDCl₃) 400 MHz δ 7.78 (s, 1H), 7.76 (d, 1H, J=9.2 Hz), 7.48 (d, 1H, J=9.2 Hz), 5.43 (d (br), 1H, J=9.6 Hz), 5.45 (d (br), 1H, J=50.8 Hz), 5.02 (d, 1H, J=9.6 Hz), 4.44 (d, 1H, J=9.6 Hz), 4.39–3.89 (m, 4H), 2.72 (dd, 1H, J=15.2), 2.48–2.32 (m, 1H), 1.60–1.40 (m, 15H) ppm.

C. (2S,4S)-1-{(2R)-2-Amino-3-[(2,1,3-benzoxadiazol-5-yl methyl)thio]-3-methylbutanoyl}-4-fluoropyrrolidine-2-carbonitrile hydrochloride.

To a CH₂Cl₂ solution (45 mL) containing compound B (444 mg, 0.770 mmol) was added TFA (5 mL). The reaction mixture was allowed to stir at RT for a period of 16.0 hours followed by neutralization with sat. NaHCO₃. The organics were separated, dried over Na₂SO₄ and concentrated to dryness to afford a crude solid. The resulting solid was purified using silica gel chromatography (99% CH₂Cl₂/1%

MeOH with 2.0M NH₃). The pure solid was dissolved into an acetone/ether mixture (1/1) and precipitated using 2.0 N HCl in ether. The resulting solid was filtered in vacuo and washed with ether. After drying under high vacuum the reaction yielded a total of 105 mg of compound C.

¹H NMR (d₆-DMSO) 400 MHz δ 8.02–7.99 (m, 2H), 7.63 (d, 1H, J=9.6 Hz), 5.55 (d (br), 1H, J=51.2 Hz), 5.07 (d, 1H, J=9.2 Hz), 4.22–3.98 (m, 5H), 2.58–2.32 (m, 2H), 1.48 (s, 3H), 1.40 (s, 3H) ppm.

Example 34

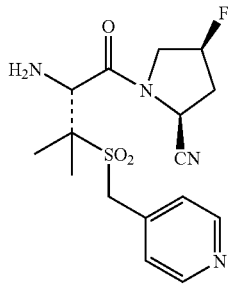

(2S,4S)-1-{(2R)-2-Amino-3-methyl-3-[(pyridin-4-yl methyl)sulfonyl]butanoyl}-4-fluoropyrrolidine-2-carbonitrile hydrochloride To a CH₂Cl₂ solution (90 mL) containing tert-butyl (1R)-1-{[(2S,4S)-2-cyano-4-fluoropyrrolidin-1-yl]carbonyl}-2-methyl-2-[(pyridin-4-yl methyl)thio]propylcarbamate (500 mg, 0.0011 mol) was added TFA (10 mL). The reaction mixture was allowed to stir at RT for a period of 16.0 hours followed by the addition of 3-chloroperoxybenzoic acid (2.0 g, 0.0114 moles). The reaction was stirred for a period of 4.0 hours followed by neutralization with 2.0 N NaOH. The organics were separated, dried over Na₂SO₄ and concentrated to dryness to afford a crude solid. The resulting solid was purified using silica gel chromatography (99% CH₂Cl₂/1% MeOH with 2.0 M NH₃). The pure solid was dissolved into an acetone/ether mixture (1/1) and precipitated using 2.0 N HCl in ether. The resulting solid was filtered in vacuo and washed with ether. After drying under high vacuum the reaction yielded a total of 22 mg of the title compound.

¹H NMR (d₄CDCl₃) 400 MHz δ 8.64 (d, 2H, J=5.6 Hz), 7.37 (d, 2H, J=5.6 Hz), 5.42 (d (br), 1H, J=51.2 Hz), 4.94 (d, 1H, J=9.6 Hz), 4.77 (d, 1H, J=13.2 Hz), 4.39–3.75 (m, 4H), 2.71 (dd, 1H, J=15.6 Hz), 2.43–2.29 (m, 1H), 2.06–1.86 (s (br), 2H), 1.62 (s, 3H), 1.46 (s, 3H) ppm.

Example 35

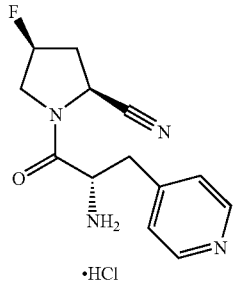

(2S,4S)-1-[(2S)-2-Amino-3-pyridin-4-ylpropanoyl]-4-fluoropyrrolidine-2-carbonitrile hydrochloride A. (2S,4S)-1-[(2S)-2-amino-3-pyridin-4-ylpropanoyl]-4-fluoropyrrolidine-2-carbonitrile hydrochloride To dry DMF (25 mL) was added (2S)-2-[(tert-butoxycarbonyl)amino]-3-pyridin-4-ylpropanoic acid (705 mg, 2.65 mmol), HATU (1.0 g, 2.65 mmol) and N,N-diisopropylethylamine (0.46 mL, 2.65 mmol). After stirring at RT for 30 min (2S, 4S)-4-fluoro-2-pyrrolidinecarbonitrile 4-methylbenzenesulfonate (581 mg, 1.99 mmol) and additional N,N-diisopropylethylamine (0.35 mL, 1.99 mmol) were added. This solution was allowed to stir at RT for 12 hours. Then was added saturated sodium bicarbonate (100 mL) and the mixture was extracted with ethyl acetate (2×100 mL) and the organics were washed with saturated NaCl (100 mL) and dried over MgSO₄ and concentrated to dryness to give the crude solid. The solid was purified by column chromatography (silica gel, hexanes/EtOAc 4:1) to provide a solid which was stirred in a dioxane solution containing HCl (4.0 M, 20 mL) for 2 hrs followed by the addition of diethyl ether (100 mL). The precipitated solid was collected by filtration and dried under high vacuum yielding 388 mg (1.3 mmol, 65% yield) of compound A as a white solid.

¹H NMR (d₆-DMSO) 400 MHz δ 8.92 (s(br), 3H), 8.84 (d, 2H, J=6.2 Hz), 7.96 (d, 2H, J=6.2 Hz), 5.45 (d, 1H, J=51 Hz), 5.00 (d, 1H, J=8.8 Hz), 4.47 (m(br), 1H), 4.05–3.78 (m, 2H), 3.41–3.36 (m, 2H), 2.42–2.25 (m, 2H) ppm.

Example 36

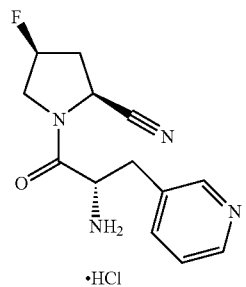

(2S,4S)-1-[(2S)-2-Amino-3-pyridin-3-ylpropanoyl]-4-fluoropyrrolidine-2-carbonitrile hydrochloride A. (2S,4S)-1-[(2S)-2-amino-3-pyridin-3-ylpropanoyl]-4-fluoropyrrolidine-2-carbonitrile hydrochloride To dry DMF (25 mL) was added (2S)-2-[(tert-butoxycarbonyl)amino]-3-pyridin-3-ylpropanoic acid (534 mg, 2.0 mmol), HATU (0.76 g, 2.0 mmol) and N,N-diisopropylethylamine (0.35 mL, 2.0 mmol). After stirring at RT for 30 min (2S, 4S)-4-fluoro-2-pyrrolidinecarbonitrile 4-methylbenzenesulfonate (438 mg, 1.5 mmol) and additional N,N-diisopropylethylamine (0.26 mL, 1.5 mmol) were added. This solution was allowed to stir at RT for a total of 12 hr and then saturated sodium bicarbonate (150 mL) was added. The mixture was extracted with ethyl acetate (3×100 mL) and the organics were washed with saturated NaCl (100 mL), dried over MgSO₄ and concentrated to dryness to give the crude solid. The solid was chromatographed (silica gel, hexanes/EtOAc 4:1) to provide a solid which was stirred in a dioxane-HCl (4.0 M, 25 mL) solution for 2 hrs followed by the addition of diethyl ether (200 mL). The precipitated solid was collected by filtration and dried under high vacuum yielding 266 mg (0.89 mmol, 59% yield) of compound A as a white solid.

$^1$H NMR (d$_6$-DMSO) 400 MHz δ 8.88 (s, 1H), 5.51 (d, 1H, J=51 Hz), 5.01 (d, 1H, J=8.8 Hz), 4.45–4.38 (m(br), 1H), 4.00–3.86 (m, 2H), 3.38–3.27 (m, 2H), 2.42–2.30 (m, 3H) ppm.

Example 37

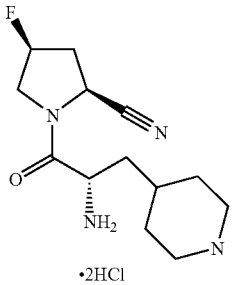

·2HCl (2S,4S)-1-[(2S)-2-Amino-3-piperidin-4-ylpropanoyl]-4-fluoropyrrolidine-2-carbonitrile dihydrochloride A. (2S)-2-[(tert-butoxycarbonyl)amino]-3-piperidin-4-ylpropanoic acid acetic acid salt.

To an acetic acid (glacial, 50 mL) solution of (2S)-2-[(tert-butoxycarbonyl)amino]-3-pyridin-4-ylpropanoic acid (0.69 g, 2.58 mmol) was added 100% Pd/C (50% w/w, 0.35 g) and hydrogenated at 60 psi under a hydrogen atmosphere. The solution was filtered through celite and concentrated to provide a white solid. Then dried under high vacuum yielding 822 mg (2.48 mmol, 96% yield) of compound A as the acetic acid salt.

$^1$H NMR (d$_6$-DMSO) 400 MHz δ 10.5 (s(br), 1H), 6.21–6.19 (m(br), 1H), 3.69–3.62 (m, 1H), 3.19–3.06 (m, 2H), 2.75–2.65 (m, 2H), 1.92 (s, 3H), 1.80–1.45 (m, 6H), 1.35 (s, 9H), 1.21–1.05 (m, 1H) ppm.

B. (2S)-2-[(Tert-butoxycarbonyl)amino]-3-[1-(tert-butoxycarbonyl)piperidin-4-yl]propanoic acid.

To a CH$_2$Cl$_2$ (150 mL) solution of (2S)-2-[(tert-butoxycarbonyl)amino]-3-piperidin-4-ylpropanoic acid acetic acid salt (1.0 g, 3.00 mmol) was added triethylamine (1.52 g, 15 mmol) and di-tert-butyl dicarbonate (786 mg, 3.6 mmol) and stirred for 12 hr. Then was added H$_2$O (50 mL) and CH$_2$Cl$_2$ (300 mL), acidified to pH 4 with 1.0 M HCl. Separation of the ethyl acetate layer followed by drying over MgSO$_4$ and filtration and removal of the solvent in vacuo yielded a clear oil. The oil was dried under high vacuum yielding 1.06 g (2.86 mmol, 95% yield) of compound B as a white solid.

$^1$H NMR (d$_6$-DMSO) 400 MHz δ 12.4 (s(br), 1H), 7.08 (d, 1H, J=8.3 Hz), 3.98–3.81 (m(br), 3H), 2.78–2.59 (m(br), 2H), 1.68–1.42 (m, 6H), 1.39 (s, 16H), 1.02–0.89 (m, 2H) ppm.

C. (2S,4S)-1-[(2S)-2-Amino-3-piperidin-4-ylpropanoyl]-4-fluoropyrrolidine-2-carbonitrile hydrochloride.

To dry DMF (25 mL) was added (2S)-2-[(tert-butoxycarbonyl)amino]-3-[1-(tert-butoxycarbonyl)piperidin-4-yl]propanoic acid (0.85 g, 2.28 mmol), HATU (0.87 g, 2.28 mmol) and N,N-diisopropylethylamine (0.40 mL, 2.28 mmol). After stirring at RT for 30 min (2S, 4S)-4-fluoro-2-pyrrolidinecarbonitrile 4-methylbenzenesulfonate (500 mg, 1.71 mmol) and additional N,N-diisopropylethylamine (0.30 mL, 1.71 mmol) were added. This solution was allowed to stir at RT for 12 hr and then saturated sodium bicarbonate (100 mL) was added. The mixture was extracted with ethyl acetate (2×100 mL) and the organics were washed with saturated NaCl (50 mL) followed by drying over MgSO$_4$. Evaporation in vacuo gave the crude solid which was chromatographed (silica gel, hexanes/EtOAc 4:1) to provide a solid which was stirred in a dioxane-HCl (4.0 M, 20 mL) solution for 2 hrs followed by the addition of diethyl ether (100 mL). The resulting precipitate was collected by filtration and dried under high vacuum yielding 432 mg (1.26 mmol, 74% yield) of compound C as a white solid.

$^1$H NMR (d$_6$-DMSO) 400 MHz δ 9.0–8.83 (s(br), 2H), 8.80–8.60 (s(br), 3H), 5.52 (d, 1H, J=51 Hz), 5.06 (d, 1H, J=8.8 Hz), 4.07–4.01 (m(br), 1H), 3.94–3.81 (m, 2H), 3.23–3.20 (m, 2H), 2.87 (s, 1H), 2.74–2.66 (m, 3H), 2.46–2.37 (m, 2H), 1.95–1.91 (m, 1H), 1.77–1.58 (m, 3H), 1.42–1.31 (m, 1H) ppm.

Example 38

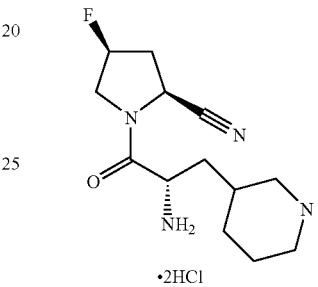

·2HCl (2S, 4S)-1-[(2S)-2-Amino-3-piperidin-3-ylpropanoyl]-4-fluoropyrrolidine-2-carbonitrile dihydrochloride A. (2S)-2-[(tert-butoxycarbonyl)amino]-3-piperidin-3-ylpropanoic acid.

To an acetic acid (glacial, 50 mL) solution of (2S)-2-[(tert-butoxycarbonyl)amino]-3-pyridin-3-ylpropanoic acid (0.8 g, 3.0 mmol) was added 10% Pd/C (50% w/w, 0.40 g) and hydrogenated at 60 psi under a hydrogen atmosphere. The solution was filtered through celite, concentrated and then dried under high vacuum yielding 946 mg (2.85 mmol, 95% yield) of compound A as the acetic acid salt.

$^1$H NMR (d$_6$-DMSO) 400 MHz δ 10.2 (s(br), 1H), 6.15–6.05 (m, 1H), 3.69–2.64 (m, 1H), 3.21–3.07 (m, 2H), 2.67–2.61 (m, 1H), 2.39–2.31 (m(br), 1H), 1.95 (s, 3H), 1.91–1.41 (m, 6H), 1.91 (s, 9H), 1.08–1.01 (m, 1H) ppm.

B. (2S)-2-[(Tert-butoxycarbonyl)amino]-3-[1-(tert-butoxycarbonyl)piperidin-3-yl]propanoic acid.

To a CH$_2$Cl$_2$ (150 mL) solution containing compound A (1.0 g, 3.00 mmol) was added triethylamine (1.52 g, 15 mmol) and di-tert-butyl dicarbonate (786 mg, 3.6 mmol) and stirred for 12 hr. The reaction was then quenched with H$_2$O (50 mL) and CH$_2$Cl$_2$ (300 mL) added. The organic layer was separated and the aqueous layer acidified to pH 4 with 1.0 M HCl followed by extraction with EtOAc. The combined organic layers were dried over MgSO$_4$ and the solvent removed in vacuo yielding a clear oil. The oil was dried under high vacuum yielding 1.07 g (2.87 mmol, 95% yield) of compound B as a white solid.

$^1$H NMR (d$_6$-DMSO) 400 MHz δ 12.15 (s(br), 1H), 7.17 (d, 1H, J=8.3 Hz), 3.95–3.87 (m(br), 3H), 2.61–2.45 (m(br), 2H), 1.73–1.40 (m, 6H), 1.35 (s, 16H), 1.2–0.89 (m, 2H) ppm.

C. (2S,4S)-1-[(2S)-2-Amino-3-piperidin-3-ylpropanoyl]-4-fluoropyrrolidine-2-carbonitrile dihydrochloride.

To dry DMF (25 mL) was added compound B (0.85 g, 2.28 mmol), HATU (0.87 g, 2.28 mmol) and N,N-diisopropylethylamine (0.40 mL, 2.28 mmol). After stirring at RT for 30 minutes (2S, 4S)-4-fluoro-2-pyrrolidinecarbonitrile 4-methylbenzenesulfonate (500 mg, 1.71 mmol) and additional N,N-diisopropylethylamine (0.30 mL, 1.71 mmol) were added. This solution was allowed to stir at RT for a total of 12 hours at which time saturated sodium bicarbonate (100 mL) was added. The mixture was extracted with ethyl acetate (2×100 mL) and the organics were washed with saturated NaCl (50 mL) and dried over MgSO$_4$. Removal of the solvent in vacuo gave the crude solid. The solid was chromatographed (silica gel, hexanes/EtOAc 4:1) to provide a solid which was stirred in a dioxane-HCl (4.0 M, 20 mL) solution for 2 hrs followed by the addition of diethyl ether (100 mL). The resulting precipitate was collected by filtration and dried under high vacuum yielding 419 mg (1.23 mmol, 72% yield) of compound C as a white solid.

$^1$H NMR (d$_6$-DMSO) 400 MHz δ 9.0–8.83 (s(br), 2H), 8.60–8.50 (s(br), 3H), 5.52 (d, 1H, J=51 Hz), 5.02 (d, 1H, J=8.8 Hz), 4.13–4.08 (m(br), 1H), 3.99–3.87 (m, 2H), 3.37–3.31 (m, 2H), 3.05–3.01 (m, 1H), 2.87 (m, 2H), 2.46–2.37 (m, 2H), 1.95–1.91 (m, 5H), 1.22–1.11 (m, 1H) ppm.

Example 39

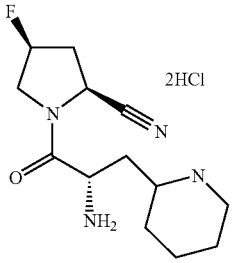

(2S,4S)-1-[(2S)-2-Amino-3-piperidin-2-ylpropanoyl]-4-fluoropyrrolidine-2-carbonitrile dihydrochloride A. (2S)-2-[(Tert-butoxycarbonyl)amino]-3-piperidin-2-yl propanoic acid To an acetic acid (glacial, 50 mL) solution of (2S)-2-[(tert-butoxycarbonyl)amino]-3-pyridin-2-ylpropanoic acid (1.6 g, 6.0 mmol) was added 100% Pd/C (50% w/w, 0.80 g) and hydrogenated at 60 psi under a hydrogen atmosphere. The solution was filtered through celite, concentrated and then dried under high vacuum yielding 951 mg (2.85 mmol, 95% yield) of compound A as the acetic acid salt.

$^1$H NMR (d$_6$-DMSO) 400 MHz δ 10.15 (s(br), 1H), 6.21–6.19 (m, 1H), 3.69–2.64 (m, 1H), 3.61–3.56 (m, 2H), 3.27–3.12 (m, 2H), 2.72–2.65 (m, 1H), 1.89 (s, 3H), 1.81–1.63 (m, 5H), 1.52–2.42 (m, 1H), 1.91 (s, 9H) ppm.

B. (2S)-2-[(Tert-butoxycarbonyl)amino]-3-[1-(tert-butoxycarbonyl)piperidin-2-yl]propanoic acid.

To a CH$_2$Cl$_2$ (150 mL) solution of compound A (1.5 g, 4.50 mmol) was added triethylamine (2.27 g, 23 mmol) and di-tert-butyl dicarbonate (1.18 g, 5.4 mmol). After stirring for 12 hr H$_2$O (50 mL) and CH$_2$Cl$_2$ (300 mL) were added followed by acidification to pH 3 with 1.0 M HCl. Separation of the organic layer followed by drying over MgSO$_4$ and removal of the solvent in vacuo yielded a clear oil. The oil was dried under high vacuum yielding 1.68 g (4.45 mmol, 95% yield) of compound B as a white solid.

$^1$H NMR (d$_6$-DMSO) 400 MHz δ 12.2 (s(br), 1H), 7.15 (d, 1H, J=8.3 Hz), 4.25–3.99 (m(br), 3H), 3.89–3.78 (m(br), 2H), 2.68–2.58 (m, 1H) 1.79–1.40 (m, 5H), 1.35 (s, 16H), 1.2–1.14 (m, 2H) ppm.

C. (2S,4S)-1-[(2S)-2-Amino-3-piperidin-2-ylpropanoyl]-4-fluoropyrrolidine-2-carbonitrile dihydrochloride.

To dry DMF (25 mL) was added compound B (850 mg, 2.28 mmol), HATU (869 mg, 2.28 mmol) and N,N-diisopropylethylamine (0.40 mL, 2.28 mmol). After stirring at RT for 30 min (2S, 4S)-4-fluoro-2-pyrrolidinecarbonitrile 4-methylbenzenesulfonate (500 mg, 1.71 mmol) and additional N,N-diisopropylethylamine (0.30 mL, 1.71 mmol) were added. This solution was allowed to stir at RT for 12 hr and then saturated sodium bicarbonate (110 mL) was added. The mixture was extracted with ethyl acetate (2×100 mL) and the organics were washed with saturated NaCl (50 mL) and dried over MgSO$_4$. Removal of the solvent in vacuo gave a crude solid. The solid was chromatographed (silica gel, hexanes/EtOAc 4:1) to provide a solid which was stirred in a dioxane-HCl (4.0 M, 20 mL) solution for 2 hrs followed by the addition of diethyl ether (100 mL). The resulting precipitate was collected by filtration and dried under high vacuum yielding 365 mg (1.07 mmol, 63% yield) of compound C as a white solid.

$^1$H NMR (d$_6$-DMSO) 400 MHz 69.32–9.10 (s(br), 2H), 8.79–8.53 (s(br), 3H), 5.51 (d, 1H, J=51 Hz), 5.04 (d, 1H, J=8.8 Hz), 4.25–4.21 (m(br), 1H), 4.19–3.88 (m, 2H), 3.58–3.46 (m, 1H), 3.42–3.32 (m, 2H), 2.85 (s, 1H), 2.71–2.63 (m, 2H), 2.27–2.14 (m, 1H), 2.05–1.97 (m, 1H), 1.81–1.40 (m, 5H) ppm.

Example 40

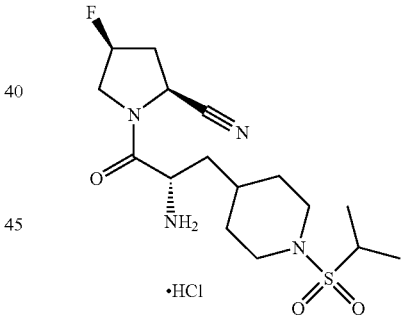

(2S,4S)-1-{(2S)-2-Amino-3-[1-(isopropylsulfonyl)piperidin-4-yl]propanoyl}-4-fluoropyrrolidine-2-carbonitrilehydrochloride A. (2S)-2-[(Tert-butoxycarbonyl)amino]-3-[1-(isopropylsulfonyl)piperidin-4-yl propanoic acid.

To an CH$_3$CN (150 mL) solution of compound A from example 12 (1.0 g, 3.00 mmol) was added triethylamine (1.52 g, 15 mmol) and isopropylsulfonyl chloride (513 mg, 3.6 mmol). After stirring for 6 hrs the acetonitrile was removed in vacuo and H$_2$O (50 mL) and ethyl acetate (300 mL) were added. Separation of the ethyl acetate layer followed by drying over MgSO$_4$ and removal of the solvent in vacuo yielded a solid which was washed with ether and dried under high vacuum yielding 860 mg (2.26 mmol, 75% yield) of compound A as a white solid.

¹H NMR (d₆-DMSO) 400 MHz δ 12.4 (s(br), 1H), 7.15 (d, 1H, J=8.3 Hz), 4.37–4.29 (m, 1H), 3.99–3.95 (m(br), 1H), 3.85–3.80 (m, 1H), 3.62–3.58 (m, 1H), 2.97–2.92 (m, 1H), 2.42–2.37 (m, 1H), 1.91–1.89 (m, 1H) 1.87–1.46 (m, 7H), 1.37 (s, 9H), 1.19–0.89 (d, 4H) ppm.

B. (2S,4S)-1-{(2S)-2-Amino-3-[1-(isopropylsulfonyl)piperidin-4-yl]propanoyl}-4-fluoropyrrolidine-2-carbonitrile-hydrochloride.

To dry DMF (25 mL) was added compound A (1.75 g, 4.62 mmol), HATU (1.76 g, 4.62 mmol) and N,N-diisopropylethylamine (0.80 mL, 4.62 mmol). After stirring at RT for 30 minutes (2S, 4S)-4-fluoro-2-pyrrolidinecarbonitrile 4-methylbenzenesulfonate (1.0 g, 3.47 mmol) and additional N,N-diisopropylethylamine (0.60 mL, 3.47 mmol) were added. This solution was allowed to stir at RT for 12 hr and then saturated sodium bicarbonate (110 mL) was added. The mixture was extracted with ethyl acetate (2×100 mL) and the organics were washed with saturated NaCl (50 mL) and dried over MgSO₄. Removal of the solvent in vacuo gave a crude solid. The solid was chromatographed (silica gel, hexanes/EtOAc 4:1) to provide a solid which was stirred in a dioxane-HCl (4.0 M, 20 mL) solution for 2 hrs followed by the addition of diethyl ether (100 mL). The precipitate was collected by filtration and dried under high vacuum yielding 969 mg (2.35 mmol, 68% yield) of compound B as a white solid.

¹H NMR (d₆-DMSO) 400 MHz δ 8.51–8.44 (s(br), 3H), 5.15 (d, 1H, J=51 Hz), 5.06 (d, 1H, J=8.8 Hz), 4.04–4.01 (s(br), 1H), 3.96–3.84 (m, 2H), 3.72–3.61 (m, 2H), 3.51–3.37 (m(br), 2H), 3.35–3.27 (m, 1H), 2.79–2.76 (m, 2H), 1.82–1.69 (m, 5H), 1.17 (m, 8H) ppm.

Hz), 4.27–4.21 (m, 1H), 3.98–3.95 (m, 1H), 3.58–3.52 (m, 1H), 2.98–2.91 (m, 1H), 2.42 (s, 3H), 2.21–2.20 (m, 1H), 1.81–1.50 (m, 6H), 1.39 (s, 9H), 1.21–1.08 (m, 1H) ppm.

B. (2S,4S)-1-{(2S)-2-Amino-3-[1-(4-methylphenylsulfonyl)piperidin-4-yl]propanoyl}-4-fluoropyrrolidine-2-carbonitrile hydrochloride.

To dry DMF (25 mL) was added compound A (2.13 g, 5.0 mmol), HATU (1.90 g, 5.00 mmol) and N,N-diisopropylethylamine (0.87 mL, 5.0 mmol). After stirring at RT for 30 minutes (2S, 4S)-4-fluoro-2-pyrrolidinecarbonitrile 4-methylbenzenesulfonate (1.1 g, 3.75 mmol) and additional N,N-diisopropylethylamine (0.65 mL, 3.75 mmol) were added. This solution was allowed to stir at RT for 12 hr and then saturated sodium bicarbonate (110 mL) was added. The mixture was extracted with ethyl acetate (2×100 mL) and the organics were washed with saturated NaCl (50 mL) and dried over MgSO₄. Removal of the solvent in vacuo gave a crude solid that was chromatographed (silica gel, hexanes/EtOAc 4:1) to provide a solid which was stirred in a dioxane-HCl (4.0 M, 20 mL) solution for 2 hrs followed by the addition of diethyl ether (100 mL). The resulting precipitate was collected by filtration and dried under high vacuum yielding 1.10 g (2.4 mmol, 64% yield) of compound B as a white solid.

¹H NMR (d₆-DMSO) 400 MHz δ 8.21–8.05 (s(br), 3H), 7.60 (d, 2H, J=7.9 Hz), 7.43 (d, 2H, J=7.9 Hz), 3.91–3.88 (m, 2H), 3.07–2.99 (m, 1H), 2.43 (s, 3H), 2.09–2.03 (m, 1H), 1.94–1.29 (m, 8H), 1.12–1.02 (m, 1H) ppm.

Example 41

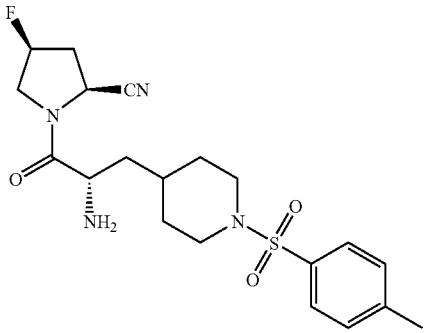

(2S,4S)-1-{(2S)-2-Amino-3-[1-(4-methylphenylsulfonyl)piperidin-4-yl]propanoyl}-4-fluoropyrrolidine-2-carbonitrile hydrochloride A. (2S)-2-[(Tert-butoxycarbonyl)amino]-3-[1-(4-methylphenylsulfonyl)piperidin-4-yl]propanoic acid.

To a CH₃CN (150 mL) solution of compound A from example 12 (1.0 g, 3.00 mmol) was added triethylamine (1.52 g, 15 mmol) and toluenesulfonyl chloride (686 mg, 3.6 mmol). After stirring for 6 hrs the acetonitrile was removed in vacuo and H₂O (50 mL) and ethyl acetate (300 mL) were added. Separation of the ethyl acetate layer followed by drying over MgSO₄ and removal of the solvent in vacuo yielded a solid which was washed with ether and dried under high vacuum yielding 1.09 g (2.56 mmol, 85% yield) of compound A as a white solid.

¹H NMR (d₆-DMSO) 400 MHz δ 12.4 (s(br), 1H), 7.61 (d, 2H, J=8.2 Hz), 7.42 (d, 2H, J=8.2 Hz), 7.13 (d, 1H, J=8.3

Example 42

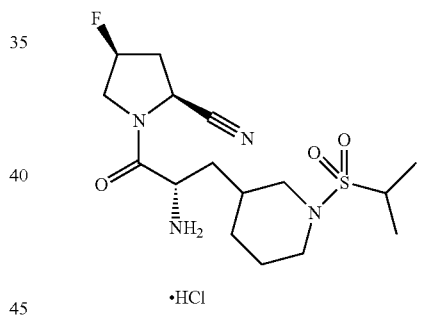

·HCl (2S,4S)-1-{(2S)-2-Amino-3-[1-(isopropylsulfonyl)piperidin-3-yl]propanoyl}-fluoropyrrolidine-2-carbonitrile hydrochloride A. (2S)-2-[(tert-butoxycarbonyl)amino]-3-[1-(isopropylsulfonyl)piperidin-3-yl]propanoic acid.

To a CH₃CN (150 mL) solution compound A from example 13 (1.0 g, 3.00 mmol) was added triethylamine (1.52 g, 15 mmol) and isopropylsulfonyl chloride (513 mg, 3.6 mmol). After stirring for 6 hr the acetonitrile was removed in vacuo and then added H₂O (50 mL) and ethyl acetate (300 mL) were added. Separation of the ethyl acetate layer followed by drying over MgSO₄ and removal of the solvent in vacuo yielded a solid which was washed with ether and dried under high vacuum yielding 926 mg (2.43 mmol, 81% yield) of compound A as a white solid.

¹H NMR (d₆-DMSO) 400 MHz δ 12.2 (s(br), 1H), 7.18 (d, 1H, J=8.3 Hz), 3.94–3.89 (m, 1H), 3.55–3.49 (m(br), 2H), 3.35–3.30 (m, 2H), 2.89–2.85 (m, 1H), 2.62–2.57 (m, 1H), 1.91–1.42 (m, 5H), 1.39 (s, 9H), 1.19 (d, 6H) ppm.

B. (2S,4S)-1-{(2S)-2-Amino-3-[1-(isopropylsulfonyl)piperidin-3-yl]propanoyl}-4-fluoropyrrolidine-2-carbonitrile hydrochloride.

To dry DMF (25 mL) was added compound A (1.75 g, 4.62 mmol), HATU (1.76 g, 4.62 mmol) and N,N-diisopropylethylamine (0.80 mL, 4.62 mmol). After stirring at RT for 30 minutes (2S, 4S)-4-fluoro-2-pyrrolidinecarbonitrile 4-methylbenzenesulfonate (1.0 g, 3.47 mmol) and additional N,N-diisopropylethylamine (0.60 mL, 3.47 mmol) were added. This solution was allowed to stir at RT for 12 hr and then saturated sodium bicarbonate (110 mL) was added. The mixture was extracted with ethyl acetate (2×100 mL) and the organics were washed with saturated NaCl (50 mL) and dried over MgSO$_4$. Removal of the solvent in vacuo gave a crude solid. This solid was chromatographed (silica gel, hexanes/EtOAc 4:1) to provide a solid which was stirred in a dioxane-HCl (4.0 M, 20 mL) solution for 2 hrs followed by the addition of diethyl ether (100 mL). The resulting precipitate was collected by filtration and dried under high vacuum yielding 1.01 g (2.46 mmol, 71% yield) of compound B as a white solid.

$^1$H NMR (d$_6$-DMSO) 400 MHz 8.42–8.39 (s(br), 3H), 5.51 (d, 1H, J=51 Hz), 5.06 (d, 1H, J=8.8 Hz), 4.07–4.01 (s(br), 1H), 3.98–3.84 (m, 2H), 3.52–3.49 (m, 1H), 3.41–3.27 (m(br), 4H), 3.09–3.02 (m, 1H), 2.98–2.80 (m, 1H), 2.65–2.61 (m, 1H), 1.77–1.63 (m, 6H), 1.18 (m, 8H) ppm.

Example 43

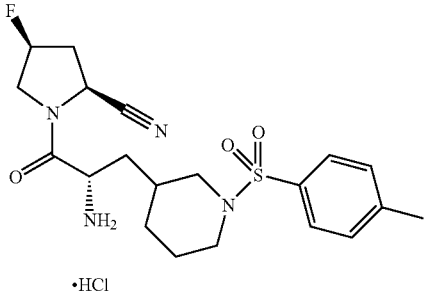

·HCl (2S,4S)-1-{(2S)-2-Amino-3-[1-(4-methylphenylsulfonyl)piperidin-3-yl]propanoyl}-4-fluoropyrrolidine-2-carbonitrile hydrochloride A. (2S)-2-[(Tert-butoxycarbonyl)amino]-3-[1-(4-methylphenylsulfonyl)piperidin-3-yl]propanoic acid To an CH$_3$CN (150 mL) solution of compound A from example 13 (1.0 g, 3.00 mmol) was added triethylamine (1.52 g, 15 mmol) and toluene sulfonyl chloride (686 mg, 3.6 mmol). After stirring for 6 hrs the acetonitrile was removed in vacuo and then H$_2$O (50 mL) and ethyl acetate (300 mL) were added. Separation of the ethyl acetate layer followed by drying over MgSO$_4$ and removal of the solvent in vacuo yielded a solid which was washed with ether and dried under high vacuum yielding 946 mg (2.22 mmol, 74% yield) of compound A as a white solid.

$^1$H NMR (d$_6$-DMSO) 400 MHz δ 12.4 (s(br), 1H), 7.61 (d, 2H, J=8.2 Hz), 7.41 (d, 2H, J=8.2 Hz), 7.15 (d, 1H, J=8.3 Hz), 3.98–3.91 (m, 1H), 3.45–3.41 (m, 2H), 2.42 (s, 3H), 2.21–2.20 (m, 1H), 2.05–1.95 (m, 1H), 1.87–1.45 (m, 6H), 1.42 (s, 9H), 1.21–1.08 (m, 1H) ppm.

B. (2S,4S)-1-{(2S)-2-Amino-3-[1-(4-methylphenylsulfonyl)piperidin-3-yl]propanoyl}-4-fluoropyrrolidine-2-carbonitrile hydrochloride.

To a dry DMF (25 mL) was added compound A (2.13 g, 5.0 mmol), HATU (1.90 g, 5.00 mmol) and N,N-diisopropylethylamine (0.87 mL, 5.0 mmol). After stirring at RT for 30 minutes (2S, 4S)-4-fluoro-2-pyrrolidinecarbonitrile 4-methylbenzenesulfonate (1.1 g. 3.75 mmol) and additional N,N-diisopropylethylamine (0.65 mL, 3.75 mmol) were added. This solution was allowed to stir at RT for a total of 12 hr and then saturated sodium bicarbonate (110 mL) was added. The mixture was extracted with ethyl acetate (2×100 mL) and the organics were washed with saturated NaCl (50 mL) and dried over MgSO$_4$ and concentrated to dryness to give a crude solid. The solid was chromatographed (silica gel, hexanes/EtOAc 4:1) to provide a solid which was stirred in a dioxane-HCl (4.0 M, 20 mL) solution for 2 hrs followed by the addition of diethyl ether (100 mL). The resulting precipitate was collected by filtration and dried under high vacuum yielding 1.17 g (2.55 mmol, 51% yield) of compound B as a white solid.

$^1$H NMR (d$_6$-DMSO) 400 MHz δ 8.50–8.43 (s(br), 3H), 7.61 (d, 2H, J=7.9 Hz), 7.43 (d, 2H, J=7.9 Hz), 5.51 (d, 1H, J=51 Hz), 5.07 (d, 1H, J=8.8 Hz), 4.07–4.01 (brm, 1H), 3.91–3.83 (m, 1H), 3.48–3.40 (m, 2H), 3.17–3.05 (m, 2H), 2.57–2.51 (m, 1H), 2.38 (s, 3H), 1.84–1.23 (m, 8H), 1.07–1.05 (m, 1H) ppm.

Example 44

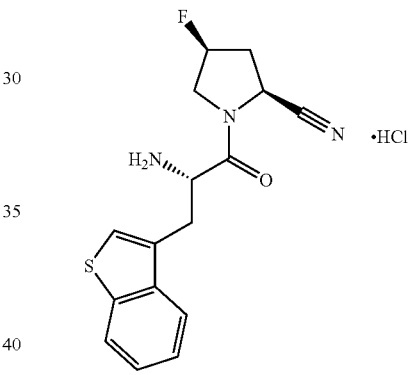

(2S,4S)-1-[(2S)-2-Amino-3-(1-benzothien-3-yl)propanoyl]-4-fluoropyrrolidine-2-carbonitrile hydrochloride A. (2S,4S)-1-[(2S)-2-Amino-3-(1-benzothien-3-yl)propanoyl]-4-fluoropyrrolidine-2-carbonitrile hydrochloride.

To dry DMF (25 mL) was added (2S)-3-(1-benzothien-3-yl)-2-[(tert-butoxycarbonyl)amino]propanoic acid (1.92 g, 6.0 mmol), HATU (2.28 g, 6.0 mmol) and N,N-diisopropylethylamine (1.05 mL, 6.0 mmol). After stirring at RT for 30 min (2S, 4S)-4-fluoro-2-pyrrolidinecarbonitrile 4-methylbenzenesulfonate (1.31 g, 4.5 mmol) and additional N,N-diisopropylethylamine (0.78 mL, 4.5 mmol) were added. This solution was allowed to stir at RT for 12 hr and then saturated sodium bicarbonate (110 mL) was added. The mixture was extracted with ethyl acetate (2×100 mL) and the organics were washed with saturated NaCl (50 mL), dried over MgSO$_4$ and concentrated to dryness to give a crude solid. The solid was chromatographed (silica gel, hexanes/EtOAc 4:1) to provide a solid which was stirred in a dioxane-HCl (4.0 M, 20 mL) solution for 2 hrs followed by the addition of diethyl ether (100 mL). The precipitate was collected by filtration and dried under high vacuum yielding 1.0 g (2.84 mmol, 63% yield) of compound A as a white solid.

$^1$H NMR (d$_6$-DMSO) 400 MHz δ 8.70–8.61 (s(br), 3H), 8.05–8.00 (m, 2H), 7.45–7.36 (m, 3H), 5.21 (d, 1H, J=51 Hz), 5.01 (d, 1H, J=8.8 Hz), 4.23–4.20 (m, 1H), 3.71 (ddd, 1H, J=41.1, 12.3, 3.2 Hz), 3.55–3.51 (m, 1H), 3.30–3.24 (m, 1H), 2.73 (q, 1H, J=12.1 Hz), 2.39–2.14 (m, 2H) ppm.

Example 45

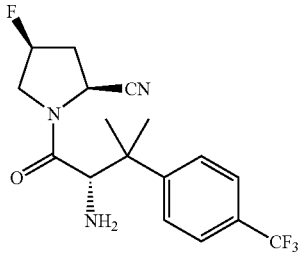

(2S,4S)-1-{(2S)-2-Amino-3-methyl-3-[4-(trifluoromethyl)phenyl]butanoyl}-4-fluoropyrrolidine-2-carbonitrile hydrochloride A. 2-Methyl-2-[4-(trifluoromethyl)phenyl]propanal.

To a toluene solution (90 mL) containing 2-methyl-2-[4-(trifluoromethyl)phenyl]propanenitrile (see: *J. Am. Chem. Soc.* 2000, 122, 712, Caron, S. et al. for the preparation of this compound) (5.54 g, 26.0 mmol) cooled to −78° C. was added 26.0 mL of a 1.5 M toluene solution of DIBAL (39.0 mmol). The resulting solution stirred at −78° C. for 2.5 hr at which time it was quenched with an aqueous THF solution (105 mL/20 mL) containing sodium acetate (6.6 g) and acetic acid (6.6 mL). After 5 min the cold bath was removed and stirring continued for 20 min at RT when celite and Et$_2$O were added. Upon stirring an additional 30 min, the heterogeneous solution was filtered through a bed of celite. The celite was rinsed thoroughly with Et$_2$O and then the aqueous layer separated. The organics were washed with H$_2$O, dried (MgSO$_4$) and the solvent removed in vacuo. The residual oil was purified via column chromatography (5% EtOAc/hexanes) yielding 4.22 g (19.5 mmol, 75% yield) of compound A as a clear oil.

$^1$H NMR (CDCl$_3$) 400 MHz δ 9.52 (s, 1H), 7.63 (d, 2H, J=8.2 Hz), 7.39 (d, 2H, J=8.2 Hz), 1.49 (s, 3H) ppm.

B. 2-Amino-3-methyl-3-[4-(trifluoromethyl)phenyl]butanenitrile.

To a MeOH solution (10 mL) containing compound A (1.87 g, 8.66 mmol) was added 1.2 mL of 30% NH$_4$OH, H$_2$O (6 mL) and potassium cyanide (592 mg, 9.09 mmol). To this solution was added ammonium chloride (510 mg, 9.53 mmol) at RT. After 1 hr the solution was heated to 70° C. for 6 hr. Upon cooling, the reaction was diluted with EtOAc and then washed with sat NaHCO$_3$ and H$_2$O. After drying over MgSO$_4$ the solvent was removed in vacuo and the residue purified via column chromatography (EtOAc/hexanes (3:2)) yielding 1.52 g (6.27 mmol, 72% yield) of compound B.

$^1$H NMR (CDCl$_3$) 400 MHz δ 7.63 (d, 2H, J=8.4 Hz), 7.55 (d, 2H, J=8.5 Hz), 3.80 (t, 1H, J=7.9 Hz), 1.56 (s, 3H), 1.53 (s, 3H), 1.40 (d(br), 2H, J=6.9 Hz) ppm.

C. 2-Amino-3-methyl-3-[4-(trifluoromethyl)phenyl]butanoic acid hydrochloride.

To a flask containing compound B (2.96 g, 12.2 mmol) was added 10 mL of acetic acid followed by 60 mL of concentrated HCl. The solution was then heated to reflux overnight and upon cooling the bulk of the solvent was removed in vacuo. The resulting white solid was triterated with an Et$_2$O/hexanes (2:1) solution and collected via vacuum filtration. After pumping on under high vacuum 3.13 g (10.5 mmol, 86% yield) of compound C was obtained as a white solid.

$^1$H NMR (d$_4$-MeOH) 400 MHz δ 7.69–7.68 (m, 4H), 4.33 (s, 1H), 1.57 (s, 3H), 1.53 (s, 3H) ppm.

D. 2-[(Tert-butoxycarbonyl)amino]-3-methyl-3-[4-(trifluoromethyl)phenyl]butanoic acid.

To a dioxane (30 mL)/H$_2$O (7 mL) solution containing compound C (3.05 g, 10.2 mmol) was added 12.8 mL of a 2.0 M NaOH solution (25.6 mmol) followed by di-t-butyl dicarbonate (3.13 g, 14.4 mmol) at RT. The solution stirred overnight at which time it was poured into sat. NaHCO$_3$ and washed with Et$_2$O. The Et$_2$O layer was washed with sat NaHCO$_3$ and then the aqueous layers combined. After acidification with 1.0 M HCl the organics were extracted with EtOAc (2×). After drying over MgSO$_4$ the solvent was removed in vacuo yielding 3.58 g (9.92 mmol, 97% yield) of compound D as a white solid.

$^1$H NMR (CDCl$_3$) 400 MHz δ 7.57 (d, 2H, J=8.2 Hz), 7.49 (d, 2H, J=8.3 Hz), 4.99 (d(br), 1H, J=9.2 Hz), 4.63 (d(br), 1H, J=9.3 Hz), 1.45 (s, 3H), 1.44 (s, 3H), 1.36 (s, 9H) ppm.

E. Tert-butyl (1S)-1-{[(2S,4S)-2-cyano-4-fluoropyrrolidin-1-yl]carbonyl}-2-methyl-2-{4-(trifluoromethyl)phenyl]propylcarbamate.

To a DMF solution (45 mL) containing compound D (2.0 g, 5.54 mmol) was added N,N-diisopropylethylamine (788 mg, 6.09 mmol) followed by HATU (2.21 g, 5.82 mmol) at RT. The resulting solution stirred for 30 min at which time a DMF solution (27 mL) containing (2S,4S)-4-fluoro-2-pyrrolidinecarbonitrile 4-methylbenzenesulfonate (1.66 g, 5.82 mmol) and N,N-diisopropylethylamine (752 mg, 5.82 mmol) was added. After stirring overnight the solution was diluted with EtOAc and washed with H$_2$O (3×), sat NaHCO$_3$ and 1.0 M HCl. After drying over MgSO$_4$ the solvent was removed in vacuo and the residual dark oil purified via column chromatography (hexanes/EtOAc/CH$_2$Cl$_2$ (5:4:1)). A low R$_f$ material (610 mg, 1.37 mmol) was obtained which was a single stereoisomer by $^1$H NMR and LC plus 335 mg of a high R$_f$ material which contained desired product, but was contaiminated with another compound. The low R$_f$ material turned out to be the (S)-diastereomer after in vitro testing. Low R$_f$ diastereomer:

$^1$H NMR (CDCl$_3$) 400 MHz δ 7.65–7.60 (m, 2H), 7.59–7.55 (m, 2H), 5.29 (d, 1H, J=9.9 Hz), 5.06 (dt, 1H, J=51.1, 3.3 Hz), 4.85 (d, 1H, J=9.4 Hz), 4.34 (d, 1H, J=9.9 Hz), 3.55 (ddd, 1H, J=3.4, 12.1, 36.2 Hz), 2.70 (dd, 1H, J=12.3, 17.8 Hz), 2.48 (t, 1H, J=15.4 Hz), 2.15 (m, 1H), 1.53 (s, 3H), 1.51 (s, 3H), 1.40 (s, 9H) ppm.

F. (2S,4S)-1-{(2S)-2-Amino-3-methyl-3-[4-(trifluoromethyl)phenyl]butanoyl}-4-fluoropyrrolidine-2-carbonitrile hydrochloride.

To a CH$_2$Cl$_2$ solution (10 mL) containing compound E (643 mg, 1.44 mmol, low R$_f$ isomer) was added TFA (1.65 g, 14.4 mmol) at RT. After 1 hr an additional 5 eq of TFA was added and after a total of 2 hr the solvent was removed in vacuo and the residual oil dissolved in 5 mL of dioxane. To this solution was added 10 mL of a 4.0 M dioxane solution of HCl. The solvent was removed in vacuo followed by the addition of CH$_2$Cl$_2$ and Et$_2$O. This process was repeated 3× until a consistent solid formed. The solid was collected via vacuum filtration yielding 406 mg (1.03 mmol, 72% yield) of compound F.

$^1$H NMR (d$_4$-MeOH) 400 MHz δ 7.74–7.66 (m, 4H), 5.13 (d(br), 1H, J=51.3 Hz), 4.97 (d, 1H, J=9.3 Hz), 4.25 (s, 1H), 3.52 (m, 1H), 2.74 (dd, 1H, J=22.0, 11.9 Hz), 2.47–2.22 (m, 2H), 1.67 (s, 3H), 1.60 (s, 3H) ppm.

Example 46

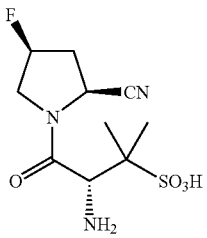

(3R)-3-Amino-4-[(2S,4S)-2-cyano-4-fluoropyrrolidin-1-yl]-2-methyl-4-oxobutane-2-sulfonic acid A. (4R)-2,2,5,5-Tetramethyl-1,3-thiazolidine-4-carboxylic acid.

To a suspension of L-penicillamine (0.300 g, 2.01 mmol) in methanol (2 mL) was added acetone (4 mL, 54.5 mmol). The solution become clear and was stirred for ca. 3 hours after which it became cloudy again. The solution was concentrated to afford 0.377 g of compound A as a white solid (99% yield).

$^1$H-NMR (d$_6$-DMSO) 400 MHz δ 3.74 (s, 1H), 2.48 (m, 2H), 1.54 (m, 6H), 1.43 (s, 3H), 1.18 (s, 3H) ppm.

B. (2S,4S)-4-Fluoro-1-{[(4R)-2,2,5,5-tetramethyl-1,3-thiazolidin-4-yl]carbonyl}pyrrolidine-2-carbonitrile.

A solution of compound A (0.256 g, 1.35 mmol), (2S, 4S)-4-fluoropyrrolidine-2-carbonitrile tosylate (0.387 g, 1.35 mmol), 1-hydroxybenzotriazole hydrate (0.182 g, 1.35 mmol) and N,N'-dicyclohexylcarbodiimide (0.279 g, 1.35 mmol) and N,N'-diisopropylethylamine (0.280 mL, 1.63 mmol) in tetrahydrofuran (13 mL) was stirred for ca. 48 hours and then concentrated. The residue was taken up with ethyl acetate and filtered. The filtrate was washed with aqueous NaHCO$_3$ and brine. The organic layer was dried over MgSO$_4$ and concentrated. The crude mixture was chromatographed on silica gel (5% MeOH/95% CHCl$_3$) to afford 0.171 g of compound B as a white solid (44% yield).

$^1$H-NMR (d$_6$-DMSO) 400 MHz δ 5.48 (d, J=50 Hz, 1H), 5.02 (m, 1H), 4.05–3.85 (m, 3H), 3.48 (m, 1H), 2.42 (m, 1H), 1.54 (m, 5H), 1.47 (s, 3H), 1.22 (s, 3H) ppm.

C. (2S,4S)-1-[(2R)-2-Amino-3-mercapto-3-methylbutanoyl]-4-fluoropyrrolidine-2-carbonitrile hydrochloride.

To a solution of compound B (0.143 g, 0.501-mmol) in 5% v:v water/methanol (20 mL) was added 1.0 N HCl (0.550 mL, 0.550 mmol). The solution was mixed at ca. 500 mbar at ca. 35° C. for ca. 1 hour. The solution was concentrated, taken up with tetrahydrofuran, dried over MgSO$_4$ and concentrated again to afford 0.163 g of compound C as an off-white solid (100% yield).

$^1$H-NMR (d$_6$-DMSO) 400 MHz δ 8.61 (s, 1H), 5.54 (d, J=52 Hz, 1H), 5.05 (d, J=9 Hz, 1H), 4.28–3.89 (m, 4H), 2.47 (m, DMSO overlap, 1H), 1.74 (m, 3H), 1.43 (m, 6H), 1.33 (s, 3H) ppm.

D. Tert-butyl-(1R)-1-{[(2S,4S)-2-cyano-4-fluoropyrrolidin-1-yl]carbonyl}-2-mercapto-2-methylpropylcarbamate.

To a solution of compound C (0.141 g, 0.501 mmol) and N,N-diisopropylethylamine (0.090 mL, 0.526 mmol) in dichloromethane (3 mL) was added di-(tert-butyl)-dicarbonate (0.120 g, 0.551 mmol) followed by additional N,N-diisopropylethylamine (0.100 mL, 0.584 mmol). The solution was stirred for ca. 2 hours and then concentrated. The crude mixture was chromatographed on silica gel (2% MeOH/98% CHCl$_3$) to afford 0.088 g of compound D as an oil which crystallized into a white solid (51% yield).

$^1$H-NMR (d$_6$-DMSO) 400 MHz δ 6.99 (d, J=9 Hz, 1H), 5.53 (d, J=51 Hz, 1H), 4.97 (d, J=7 Hz, 1H), 4.37–3.74 (m, 3H), 2.95 (s, 1H), 2.40 (m, 1H), 1.35 (m, 15H) ppm.

E. (3R)-3-Amino-4[(2S,4S)-2-cyano-4-fluoropyrrolidin-1-yl]-2-methyl-4-oxobutane-2-sulfonic acid.

To a solution of compound D (4.412 g, 12.8 mmol) in methanol (18 mL) was added 30% aqueous hydrogen peroxide (5.9 mL). The solution was stirred for ca. 30 hours, concentrated, lyophilized and dried over P$_2$O$_5$ at ca 40° C. for at least 12 hours. The crude mixture was taken up with a 20% methanol/80% chloroform/acetic acid solution and a solid precipitated. The suspension was filtered to afford 0.607 g of compound E as a pink solid (16% yield).

$^1$H-NMR (d$_6$-DMSO) 400 MHz δ 8.12 (s, 3H), 5.50 (d, J=50 Hz, 1H), 5.07 (d, J=9 Hz, 1H), 4.27–3.30 (m, 6H), 2.30 (m, DMSO overlap, 1H), 1.26 (s, 3H), 1.15 (s, 3H) ppm.

BIOLOGICAL DATA

Materials:

H-Ala-Pro-pNA•HCl was purchased from BACHEM Bioscience Inc. (product no. L-1115). A 500 mM stock solution was prepared with dimethylsulfoxide and stored at −20° C. Gly-Pro-AMC was purchased from Enzyme System Products (product no. AMC-39) and stored at −20° C. as a 10 mM stock solution in dimethylsulfoxide. Test compounds were dissolved to 10 mM in dimethylsulfoxide and this was used as a stock solution for DPP-IV titration assays. Athens Research and Technology, Inc prepared the purified human DPP-IV. The material was isolated from human prostasomes using the method of DeMeester et al., J. Immunol. Methods 189, 99–105. (1996).

DPP-IV Assay:

Two-fold serial dilutions of test compounds in 100% dimethylsulfoxide were performed in 96-well polystyrene flat bottom plates (Costar, #9017). The average enzymatic activity from wells containing dimethylsulfoxide but lacking test compound was used as a control value for calculating percent inhibition. DPP-IV (20 ng/mL) was mixed in microtiter plates with test compounds, substrate and assay buffer to yield 100 μM H-Ala-Pro-pNA•HCl in 25 mM Tris, pH 7.5, 10 mM KCl, 140 mM NaCl. The intact peptide contains a p-nitrophenylanilide which, when hydrolyzed by DPP-IV, releases the absorbant p-nitrophenylaniline. The absorbency was monitored in 20 minutes intervals at a wavelength of 387 nm using a Molecular Devices SpectraMax 250 absorbency plate reader. The enzymatic activity was determined by estimating the best linear fit to the data. Values for enzymatic activity were taken directly from the linear fit determined by the software on the plate reader.

Data Analysis: The enzymatic activity was determined by estimating the best linear fit to the data. Data reduction was performed using the Microsoft Excel RoboSage.

Determination of IC$_{50}$ values: The enzymatic activity was plotted against the concentration of test compound, including [I]=0, and the IC$_{50}$ determined from a fit of equation 2 to the data.

$$\text{RATE} = V_{max}/(1+([I]/\text{IC}_{50})) \qquad (2)$$

$V_{max}$ was the best fit estimate of the maximal enzymatic activity.

Determination of $K_i$ values: $K_i$ values were calculated from IC$_{50}$ values using equation 3 assuming a competitive model.

$$K_i = IC_{50} * \left[1 - \frac{S}{(S+K_m)}\right] \qquad (3)$$

The apparent pKi values were >5.0 for each of the examples.

DPP-II Assay:

The intermediate plate contained 5.3 µL of test compound in 2-fold serial dilutions across the plate. A volume of 209 µL of buffer (100 mM sodium acetate pH 5.5) containing substrate (H-Lys-Ala-pNA.2HCl; product no. L-2085; BACHEM Bioscience Inc.:) was added to each well of the intermediate plate, then mixed. The reaction was initiated with the transfer of 180 µL of the substrate/test compound solution to the assay plate containing 20 µL of enzyme. Final concentrations in the assay were 100 nM enzyme and 1000 µM substrate in 100 mM NaOAc, pH 5.5, 2.5% DMSO in a final volume of 200 µL The absorbance was monitored every 20 minutes for 5 hours at 387 nm using a Molecular Devices SpectraMax 250 absorbance plate reader.

Data Analysis: The enzymatic activity was determined by estimating the best linear fit to the data. Data reduction was performed using the Microsoft Excel RoboSage.

Determination of IC$_{50}$ values: The enzymatic activity was plotted against the concentration of test compound, including [I]=0, and the IC$_{50}$ determined from a fit of equation 2 to the data.

$$\text{RATE} = V_{max}/(1+([I]/\text{IC}_{50})) \qquad (2)$$

$V_{max}$ was the best fit estimate of the maximal enzymatic activity.

Determination of $K_i$ values: $K_i$ values were calculated from IC$_{50}$ values using equation 3 assuming a competitive model.

$$K_i = IC_{50} * \left[1 - \frac{S}{(S+K_m)}\right] \qquad (3)$$

Certain compounds of the present invention showed activity for DPP-II, for example pKi values >6.0, while others demonstrated selectivity for DPP-IV, discussed hereinabove.

In Vivo Studies:

Age and weight matched male CD1 mice were housed individually at 72° F. and 50% relative humidity with a 12 h light/dark cycle. Animals were dosed by oral gavage with 10 ml/kg vehicle (0.5% methylcellulose (HPMC) with 0.1% Tween 80) or 1 mg/kg test compound in vehicle. The animals were anesthetized with isofluorane for blood collection at the specified times (0–6 hours). Plasma DPP-IV activity was measured using the fluorogenic substrate Gly-Pro-AMC (50 µM) according to the manufacturers specification (Enzyme System Products, Livermore Calif.). The substrate was mixed with 50 mM Tris, pH 7.8 and 20% plasma. The samples were incubated for 20 min at 30° C. and fluorescence measured using a cytofluor spectrofluoremeter with the filters set at 360 nm excitation and 460 nm emission.

COMPARATIVE EXAMPLES

The compounds of the present invention demonstrate a number of preferred characterisitcs. Not to be limtied thereby, but the preferred characteristics of the compounds of the present invention are believed due to the unexpected benefits gained through manipulation of the substitution patterns of the compounds of Formula (I). The results of comparative testing illustrate several surprising and unexpected benefits. More specifically, the comparative tests indicate that the compounds of the present invention demonstrate: (i) increased potency, as characterized by DPP-IV inhibition activity measured from plasma; (ii) increased selectivity; (iii) increased duration of action; and/or (iv) an increased safety profile.

COMPARISON EXAMPLES

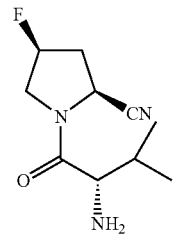

Comparison Example 1

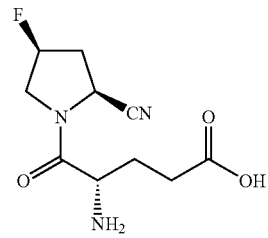

Comparison Example 2

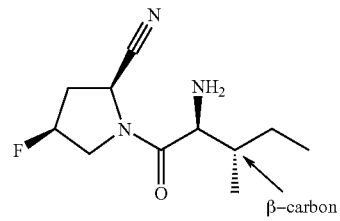

Comparison Example 3

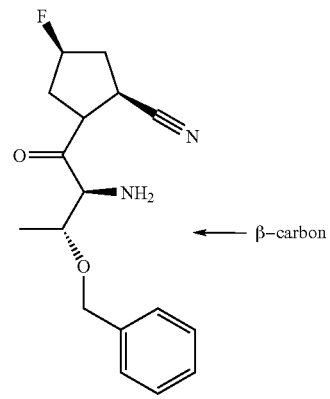

Comparison Example 4

-continued

Comparison Example 5

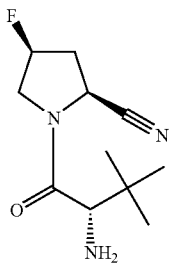

Comparison Example 6

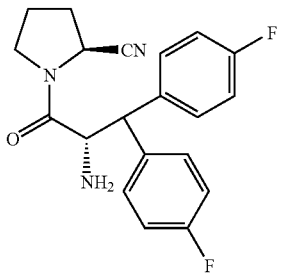

Comparator I—Potency/Duration

Surprisingly, with regard to inhibtion of dipeptidyl peptidases, in particular with DPP-IV, compounds that demonstrate high affinity for the enzyme (i.e. potent) do not necessarily possess the duration of action desired for therapeutic effectievness. Duration of action, as used herein, includes the ability of the compound to maintain effectiveness, preferably therapeutic effectiveness, over a sustained period of time. A compound demonstrating the preferred level of duration of action provides therapeutic effectiveness with once-daily dosing. A once-a-day dosage regimen, as is appreciated in the pharmaceutical arts, may be advantageous over multiple daily dosing regimens for reasons such as patient compliance and convenience. Thus, preferred compounds should not only be sufficiently potent but should also demonstrate desired levels of duration of action.

Unfortunately, as is appreciated by those skilled in the art, there is no necessary correlation between potency and duration of action. In other words, although a compound demonstrates high affinity for the DPP-IV enzyme, the compound does not necessarily have appropriate duration properties to be considered for preferential once-daily dosing. The following illustrates this lack of correlation between potency and duration of action. The following data illustates the invention but should not be interpreted to limit the invention.

Age and weight matched male CD rats were housed individually at 72° F. and 50% relative humidity with a 12 h light/dark cycle. Animals were dosed by oral gavage with vehicle (10 mM acetic acid) or 1 mg/kg test compound in vehicle. After 6 hrs administration of compound, the rats were anesthetized with isofluorane for cardiac blood collection. DPP-IV activity in serum was measured using the fluorogenic substrate Gly-Pro-AMC (50 mM) according to the manufacturers specification (Enzyme System Products, Livermore Calif.). The substrate was mixed with 50 mM Tris, pH 7.8, in plasma (20% final v/v) and the samples were incubated for 5–20 min at 30° C. DPP-IV activity was determined by measuring fluorescence using a cytofluor spectrofluoremeter with the filters set at 360 nm excitation and 460 nm emission. Averages and standard deviations from each group (n=3) were calculated using students t-test and compared to vehicle treated rats to determine percent inhibition as shown in Table 1.

TABLE I

| | $IC_{50}$ (nM) Human DPP-IV | Percent DPP-IV inhibition At 6 hrs In Rats |
|---|---|---|
| Comparison Example 1 | 1.3 | 32 ± 3 |
| Comparison Example 2 | 3 | 32 ± 3 |
| Comparison Example 4 | 5.6 | 2.8 ± 0.1 |
| Comparison Example 5 | 3 | 71 ± 13 |
| Example 2 | 22 | 68 ± 4 |
| Example 9 | 72 | 64 ± 12 |

As shown, Comparison Examples 1, 2, and 4 are very potent, each having $IC_{50}$ values of <5.6 nM. The compounds illustrative of the present invention, Examples 2 and 9 demonstrate adequate potency, namely $IC_{50}$ values of 22 and 72 respectively. When the Comparison Examples 1, 2, and 4 were tested for duration of action, however, they each demonstrated a poor level of duration. The compounds of the present invention, although less potent, present a duration of action preferred for overall therapeutic profile.

Comparison Example 5 is included to further demonstrate the unpredictability between potency and duration of action. More specifically, Comparison Example 5 illustrates one compound having both high binding affinity and duration of action. Thus, the relationship of potency to duration of action can not be characterized strictly as either a parallel or an inverse relationship. Rather the relationship is not predictable.

This lack of correlation between potency and duration of action presents a lack of predictability among inhibitors of dipeptidyl peptidases, specifically DPP-IV. This unpredictability has not heretofore been recognized. As shown above, binding data, alone, may or may not be enough to ascertain the therapeutic utility of such compounds. The compounds of the present invention demonstrate desired levels of both potency and duration of action in addition to the other properties herein discussed.

Comparator II-β-substitution and Cyclization

As described herein, the compounds of the present invention have at least two identical β-substitutions, namely, $R^1$ and $R^2$ are the same. As referenced herein the compounds of the present invention are di-β-substituted, as illustrated with Examples 1 and 10, respectively:

(Example 1)

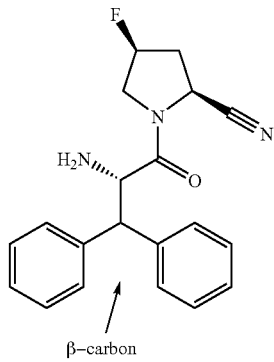

β—carbon

-continued (Example 10)

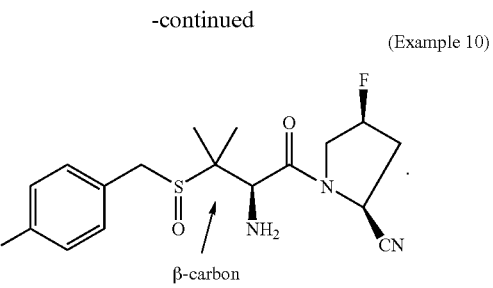

β-carbon

Thus, using Example 10 as an example, one preferred embodiment is described when $R^1$ and $R^2$ are each alkyl, more preferably $C_1$–$C_6$ alkyl, more preferably, methyl. Another preferred embodiment is illustrated by Example 1, namely, when $R^1$ and $R^2$ are each aryl, more preferably phenyl, and, as illustrated in Example 2, more preferably phenyl substituted with halogen, preferably fluorine. Generally, di-β-substituted compounds, such as those of the present invention, do not tend to cyclize with the nitruile warhead to form the cyclic amidine, and, therefore, are stable.

On the other hand, mono-β-substituted compounds, for example, Comparison Examples 3 and 4 illustrated hereinabove, where the β carbon does not carry two identical substituents tend to cyclize and, therefore, demonstrate relatively short stability half-lives, as measured by $t_{1/2}$.

In addition, generally compounds with the gem-substitution pattern on the β-carbon demonstrate increased selectivity as well.

Stability Studies for DPP IV Compounds

Typically 0.2–0.5 mg of compound is dissolved in 1 mL of Phosphate Buffered Saline (PBS) in a HPLC sample vial and placed in an autosampler thermostatically controlled at 37° C. An initial time point HPLC chromatogram is obtained followed by successive HPLC chromatograms at time points of 24, 48, 72, etc hours.

HPLC Method:
Column: Phenomenex Luna C18(2), 3μ, 100×4.6 mm, thermostated at 40° C.
Mobile Phase A: 95:5:0.2% Water:Acetonitrile: Trifluoroacetic acid
Mobile Phase B: 5:95:0.2% Water:Acetonitrile: Trifluoroacetic acid
Flow rate: 1 mL/minute
Gradient: 0–100% B in 15 minutes
UV Detection wavelength: 215 nm The area under the drug substance peak is compared to the initial area for each chromatogram and plotted as percent remaining from initial time ($t_0$).

Comparison of the cyclization/degradation reaction half-lives ($t_{1/2}$) of compounds show increased stability for the di-β-substituted compounds, such as Examples 2 and 9. Increased $t_{1/2}$ is related directly to increased stability of the compound.

TABLE 2

| Compound | $t_{1/2}$ at 37° C. |
| --- | --- |
| Example 9 | 1733 hrs |
| Example 2 | 266 hrs |
| Comparison Example 4 | 33.5 hrs |

TABLE 2-continued

| Compound | $t_{1/2}$ at 37° C. |
| --- | --- |
| Comparison Example 3 | 23 hrs (calc.)* 47 hrs at 23° C. |

*Note:
For Comparison Example 3 the autosampler was not thermostatically controlled as described hereinabove, rather the autosampler was left at ambient room temperature. Typically an increase in 10° C. increases the reaction rate two-fold, thereby decreasing the $t_{1/2}$ by two-fold. As will be appreciated by those skilled in the art, a reasonably calculated $t_{1/2}$ for Comparison Example 3 would be one half (or less) of the measured value at room temperature (23° C.).

Thus, in addition to potency and duration of action, the compounds of the present invention demonstrate desired stability as well.

Comparator III—Safety Profile

The dog is a common non-rodent species routinely used to satisfy regulatory requirements. The beagle was chosen to examine the safety of the compounds of the present invention because of the knowledge of this strain's general pathology and response to a wide variety of drugs. Dogs (Marshall Farms Inc., North Rose, N.Y., USA) from 9 to 12 months (5 to 12 kg) were dosed by oral gavage at 10 mL/kg/day with vehicle (10 mM acetic acid, pH 3.3) or test compound in vehicle. Each dose was followed by a flush of approximately 10 mL of water, once daily with 24–48 hours between each subsequent dose. If limiting gastrointestinal toxicity was not observed, the dose was increased 3-fold no sooner than approximately 24 hours after the preceding dose. Limiting GI toxicity includes diarrhea, loose or mucoid feces, blood in stool, and/or sloughing of the gut epithelium. Clinical observations were made at least three times daily during treatment (once prior to dosing, approximately one hour post dose, and once in conjunction with pm viability). DPP-IV activity in serum was measured using the fluorogenic substrate Gly-Pro-AMC (50 mM) according to the manufacturers specification (Enzyme System Products, Livermore Calif.). The substrate was mixed with 50 mM Tris, pH 7.8, in serum (20% final v/v) and the samples were incubated for 5–20 min at 30° C. DPP-IV activity was determined by measuring fluorescence using a cytofluor spectrofluoremeter with the filters set at 360 nm excitation and 460 nm emission.

The compound illustrated above as Comparison Example 5 contains a relatively small P2 portion as determined by molecular weight. Thus, Comparison Example 5 and compounds of the present invention, which are herein described as having large P2 portions, namely Examples 2 and 9 for illustration, were each tested in the described dose escalation studies.

Based on dose escalation studies in dogs, 0.3 mg/kg of Comparison Example 5 caused loose/mucoid feces with traces of blood whereas 1 mg/kg of a compound of the present invention, Example 9 caused no adverse affects. Upon escalation to 3 mg/kg, however, Example 9 caused loose/mucoid feces with traces of blood.

In contrast, 12 hours after oral dosing 0.2 mg/kg of Comparison Example 5, Comparison Example 5 inhibited DPP4 by 2%. Surprisingly, 0.2 mg/kg of Example 9 inhibited DPP4 by 76% indicating that Example 9 significantly inhibits DPP4 activity in serum.

Likewise with other compounds of the present invention, 10 mg/kg of Example 2 had no adverse affects on gastrointestinal toxicity and 0.5 mg/kg of Example 2 inhibited DPP4 by 45% 12 hours after oral dosing.

Based upon dose escalation studies in dogs, compounds of the present invention, as illustrated by Examples 2 and 9, that have a larger molecular weight P2 portion are preferred.

Comparator IV—Fluorinated v. Non-fluorinated

When compounds of the present invention were tested in vivo at time periods ranging from 0 to 10 hours, the flurorinated compounds of the present invention demonstrated a significant increase in DPP-IV inhibition over their non-fluorinated counterparts. Thus, the compounds of the present invention provide an unexpected potency that was not heretofore appreciated. For example, Example 2 and its non-fluorinated version, Comparison Example 6, were compared to determine the benefit of the 4-fluoro substituent. Surprisingly, the 4-fluoro substituent prolongs the duration of the enzyme inhibitor complex dramatically as well as providing a significant increase in potency. These beneficial properties have not heretofore been appreciated.

TABLE 3

| | $IC_{50}$ (nM) Human DPP-IV | % DPP-IV Inhibition @ 6 Hrs. In Rats |
|---|---|---|
| Example 2 | 22 | 68 ± 4 |
| Comparison Example 6 | 151 | 15 ± 1 |

All research complied with the principles of laboratory animal care (NIH publication No. 85-23, revised 1985) and GlaxoSmithKline policy on animal use.

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. A compound:

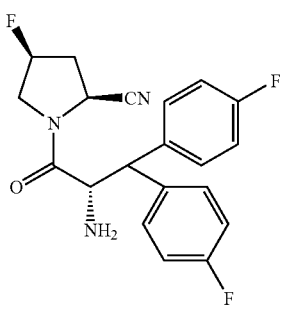

or a salt, solvate, or pharmaceutically functional derivative thereof.

2. A compound (2S,4S)-1-[(2S)-2-Amino-3,3-bis(4-fluorophenyl)propanoyl]-4-fluoropyrrolidine-2-carbonitrile hydrochloride.

3. A pharmaceutical formulation comprising a compound of claim 1.

4. The pharmaceutical formulation of claim 3 further comprising a pharmaceutically acceptable carrier.

5. A method for the treatment of diabetes, obesity, hyperlipidemia, psoriasis, intestinal distress, constipation, encephalomyelitis, glomerulonepritis, lipodystrophy, anxiety, depression, insomnia, schizophrenia, epilepsy, spasm, chronic pain, HIV infection, allergies, inflammation, arthritis, transplant rejection, high blood pressure and, congestive heart failure, tumors, comprising administering a compound of claim 1.

6. The method of claim 5 wherein the compound of claim 1 is administered for the treatment of diabetes.

7. A pharmaceutical formulation comprising a compound of claim 1 and one or more additional anti-diabetic agent selected from insulin, acarbose, emiglitate, miglitol, voglibose, metformin, buformin, phenformin, sulphonylureas, pioglitiazone, and rosiglitizone.

8. The pharmaceutical formulation of claim 7 wherein the one or more additional anti-diabetic agent selected from insulin, metformin, pioglitiazone, rosiglitizone, or combinations thereof.

9. The pharmaceutical formulation of claim 8 wherein the additional anti-diabetic agent selected from insulin, metformin, rosiglitizone, or combinations thereof.

10. A pharmaceutical formulation comprising a compound of claim 1 and metformin.

11. A pharmaceutical formulation comprising a compound of claim 1 and rosiglitizone.

12. A pharmaceutical formulation comprising a compound of claim 1, and rosiglitizone.

13. A method for the treatment of diabetes comprising administering a compound of claim 1 in combination with one or more additional anti-diabetic agent selected from insulin, acarbose, emiglitate, miglitol, voglibose, metformin, buformin, phenformin, sulphonylureas, pioglitiazone, and rosiglitizone.

14. The method of claim 13 wherein the additional anti-diabetic agent is insulin, metformin, rosiglitizone, or combinations thereof.

15. The method of claim 14 wherein the additional anti-diabetic agent is metformin, rosiglitizone, or combinations thereof.

16. A method for the treatment of diabetes comprising administering a compound of claim 1 and metformin.

17. A method for the treatment of diabetes comprising administering a compound of claim 1 and rosiglitizone.

18. A method for the treatment of diabetes comprising administering a compound of claim 1 metformin, and rosiglitizone.

* * * * *

UNITED STATES PATENT AND TRADEMARK OFFICE
CERTIFICATE OF CORRECTION

PATENT NO. : 7,132,443 B2
APPLICATION NO. : 10/481293
DATED : November 7, 2006
INVENTOR(S) : Haffner et al.

It is certified that error appears in the above-identified patent and that said Letters Patent is hereby corrected as shown below:

In the Claims:

Claim 5 (Column 94, Lines 9-16) should read as follows:
-- 5. A method for the treatment of diabetes, obesity, hyperlipidemia, psoriasis, intestinal distress, constipation, encephalomyelitis, glomerulonepritis, lipodystrophy, anxiety, depression, insomnia, schizophrenia, epilepsy, spasm, chronic pain, HIV infection, allergies, inflammation, arthritis, transplant rejection, high blood pressure, and congestive heart failure, comprising administering a compound of claim 1. --

Claim 8 (Column 94, Lines 24-27) should read as follows:
-- 8. The pharmaceutical formulation of claim 7 wherein the one or more additional anti-diabetic agent is selected from insulin, metformin, pioglitiazone, rosiglitizone, or combinations thereof. --

Claim 9 (Column 94, Lines 28-30) should read as follows:
-- 9. The pharmaceutical formulation of claim 8 wherein the additional anti-diabetic agent is selected from insulin, metformin, rosiglitizone, or combinations thereof. --

Claim 12 (Column 94, Lines 35-36) should read as follows:
-- 12. A pharmaceutical formulation comprising a compound of claim 1, metformin, and rosiglitizone. --

Claim 13 (Column 94, Lines 37-42) should read as follows:
-- 13. A method for the treatment of diabetes comprising administering a compound of claim 1 in combination with one or more additional anti-diabetic agents selected from insulin, acarbose, emiglitate, miglitol, voglibose, metformin, buformin, phenformin, sulphonylureas, pioglitiazone, and rosiglitizone. --

UNITED STATES PATENT AND TRADEMARK OFFICE
CERTIFICATE OF CORRECTION

PATENT NO. : 7,132,443 B2
APPLICATION NO. : 10/481293
DATED : November 7, 2006
INVENTOR(S) : Haffner et al.

It is certified that error appears in the above-identified patent and that said Letters Patent is hereby corrected as shown below:

Claim 18 (Column 94, Lines 53-55) should read as follows:
-- 18. A method for the treatment of diabetes comprising administering a compound of claim 1, metformin, and rosiglitizone. --

Signed and Sealed this

Ninth Day of June, 2009

JOHN DOLL
*Acting Director of the United States Patent and Trademark Office*